(12) United States Patent
Reed et al.

(10) Patent No.: US 11,532,381 B2
(45) Date of Patent: Dec. 20, 2022

(54) DISTINGUISHING PROTEIN AGGREGATION MECHANISMS

(71) Applicants: ADVANCED POLYMER MONITORING TECHNOLOGIES, INC., New Orleans, LA (US); THE ADMINISTRATORS OF THE TULANE EDUCATION FUND, New Orleans, LA (US)

(72) Inventors: Wayne Frederick Reed, New Orleans, LA (US); Daniel J. Rees, New Orleans, LA (US)

(73) Assignees: ADVANCED POLYMER MONITORING TECHNOLOGIES, INC., New Orleans, LA (US); THE ADMINISTRATORS OF THE TULANE EDUCATION FUND, New Orleans, LA (US)

(*) Notice: Subject to any disclaimer, the term of this patent is extended or adjusted under 35 U.S.C. 154(b) by 1195 days.

(21) Appl. No.: 16/070,117

(22) PCT Filed: Jan. 12, 2017

(86) PCT No.: PCT/US2017/013209
§ 371 (c)(1),
(2) Date: Jul. 13, 2018

(87) PCT Pub. No.: WO2017/123773
PCT Pub. Date: Jul. 20, 2017

(65) Prior Publication Data
US 2019/0025178 A1  Jan. 24, 2019

Related U.S. Application Data

(60) Provisional application No. 62/278,257, filed on Jan. 13, 2016.

(51) Int. Cl.
*G16C 20/20* (2019.01)
*G01N 15/00* (2006.01)

(52) U.S. Cl.
CPC ..... *G16C 20/20* (2019.02); *G01N 2015/0038* (2013.01); *G01N 2015/0053* (2013.01); *G01N 2015/0092* (2013.01)

(58) Field of Classification Search
None
See application file for complete search history.

(56) References Cited

U.S. PATENT DOCUMENTS

2007/0038127 A1  2/2007  Goldstein et al.
2008/0247991 A1  10/2008  Trout et al.
(Continued)

OTHER PUBLICATIONS

Turolla et al., "Nanoparticle scattering characterization and mechanistic modelling of UV—TiO2 photocatalytic reactors using computational fluid dynamics", Water Research, vol. 88, Jan. 1, 2016, pp. 117-126 [online] Retrieved from the Internet <URL: http://www.sciencedirect.com/science/article/pii/S0043135415302529> on Mar. 1, 2017.

(Continued)

*Primary Examiner* — Roy Y Yi
(74) *Attorney, Agent, or Firm* — Polsinelli PC

(57) ABSTRACT

Method, device, and system for identifying a model-based time dependent light scattering signature that includes receiving an experimental time dependent light scattering signature comprising experimental data descriptive of an average molecular weight of protein components in a solution over time. The method further includes identifying an Ansatz for evaluating the experimental time dependent light scattering signature, the Ansatz being an initial model-based time dependent light scattering signature, the initial model-based time dependent light scattering signature identifying at least one key variable. The method also includes adjusting (Continued)

the at least one key variable in the initial model-based time dependent light scattering signature until a final model-based time dependent light scattering signature is identified. In some instances, the final model-based time dependent light scattering signature identifies at least one protein aggregation mechanism.

20 Claims, 46 Drawing Sheets

(56) References Cited

U.S. PATENT DOCUMENTS

| | | |
|---|---|---|
| 2009/0306311 A1 | 12/2009 | Reed |
| 2013/0130294 A1* | 5/2013 | Han .................. G06Q 30/0207 435/23 |
| 2015/0056710 A1 | 2/2015 | Reed et al. |

OTHER PUBLICATIONS

PCT Search Report and Written Opinion dated Apr. 7, 2017 in corresponding PCT Application No. PCT/US2017/013209 filed Jan. 12, 2017, 10 pages.

* cited by examiner

DISTINGUISHING PROTEIN AGGREGATION MECHANISMS

CROSS-REFERENCE TO RELATED APPLICATIONS

This application is a National Stage of International Application No. PCT/US2017/013209, entitled "Distinguishing Protein Aggregation Mechanisms," filed on Jan. 12, 2017, which claims the benefit of U.S. Provisional Application No. 62/278,257, entitled "Device and Methods for Distinguishing Protein Aggregation Mechanisms," filed on Jan. 13, 2016, each of which are incorporated by reference in their entirety, for all purposes, herein.

STATEMENT OF GOVERNMENT SUPPORT

The present disclosure was made in-part with government support under EPS-1430280 awarded by the U.S. National Science Foundation and with the support of the Louisiana Board of Regents. The Government has certain rights in the present disclosure.

FIELD OF TECHNOLOGY

The present disclosure is directed to determining biological polymer aggregation mechanisms. The present disclosure is further directed to devices and methods for distinguishing protein aggregation mechanisms and other biological polymers based on time dependent light scattering signatures.

BACKGROUND

The aggregation process of proteins and other biological polymers in solution is complex and depends on many factors. Different mechanisms and kinetics are implicated both for different types of proteins and also for a given protein under different formulation and stressor conditions, such as pH, ionic strength, excipients or stabilizers present, concentration, temperature, agitation, electromagnetic and sonic radiation, and exposure to different materials. A complex series of coupled differential rate and mass balance equations control protein aggregation processes. These involve many kinetic constants that can be affected by the formulation and stressor conditions.

The formation of aggregates in solutions of therapeutic proteins, such as monoclonal antibodies, protein based vaccines, and others, is a widespread and well recognized problem in the pharmaceutical and biotechnology industries. Aggregates can lead to biologic unavailability of a drug, and worse, can provoke immune responses that can cause inflammatory responses and/or cause a buildup of immunity towards the drug, rendering it ineffective. See, for example, M. E. M. Cromwell et al., "Protein aggregation and bioprocessing", Aaps Journal 8 (2006) E572-E579; H. C. Mahler et al., "Protein Aggregation: Pathways, Induction Factors and Analysis", Journal of Pharmaceutical Sciences 98 (2009) 2909-2934; E. Y. Chi et al., "Physical stability of proteins in aqueous solution: Mechanism and driving forces in nonnative protein aggregation." Pharmaceutical Research 20 (2003) 1325-1336; and C. J. Roberts, "Kinetics of irreversible protein aggregation: Analysis of extended Lumry-Eyring models and implications for predicting protein shelf life", Journal of Physical Chemistry B 107 (2003) 1194-1207. Other classes of biological molecules, such as polynucleic acids (DNA, RNA, etc.), polysaccharides, and lipids, are also subject to aggregation and hence the current invention can be applied to them.

The formation of aggregates is a kinetic process, where there is a very specific time dependence to how the aggregates evolve in any given protein containing solution. Nonetheless, most contemporary research on aggregation is performed on an intermittent basis and relatively little attention has been paid to continuous monitoring of the aggregation process in time. One of the most widespread methods for investigating aggregation is Gel Permeation Chromatography (GPC) also sometimes termed Size Exclusion Chromatography (SEC) when the separation of particles in a chromatography column is based on their hydrodynamic volume. A typical GPC measurement takes tens of minutes to perform and hence a continuous record in time for aggregation cannot be obtained. Rather, investigators generally form a schedule for GPC runs, typically involving intervals of hours, days, and even months, between which runs the samples are stored in a particular environment, e.g. at a certain temperature, under agitation, etc. Other discrete sampling methods for characterizing aggregation include fluorescence, differential scanning calorimetry (DSC), dynamic light scattering, two dimensional infra-red absorption, isothermal titration calorimetry, optical and electrical occlusion methods, videomicroscopy, and others. Besides their lack of providing measurements continuous in time these methods frequently are for only one sample at a time, especially GPC, making these an inefficient means of characterizing very large numbers of samples. In pharmaceutical and biotechnology applications, development of protein based drugs generally requires the testing of hundreds or thousands of candidates, formulations, and conditions to arrive at a successful pharmaceutical product.

BRIEF DESCRIPTION OF THE DRAWINGS

Embodiments of the present application are described, by way of example only, with reference to the attached Figures, wherein.

Figure 1:
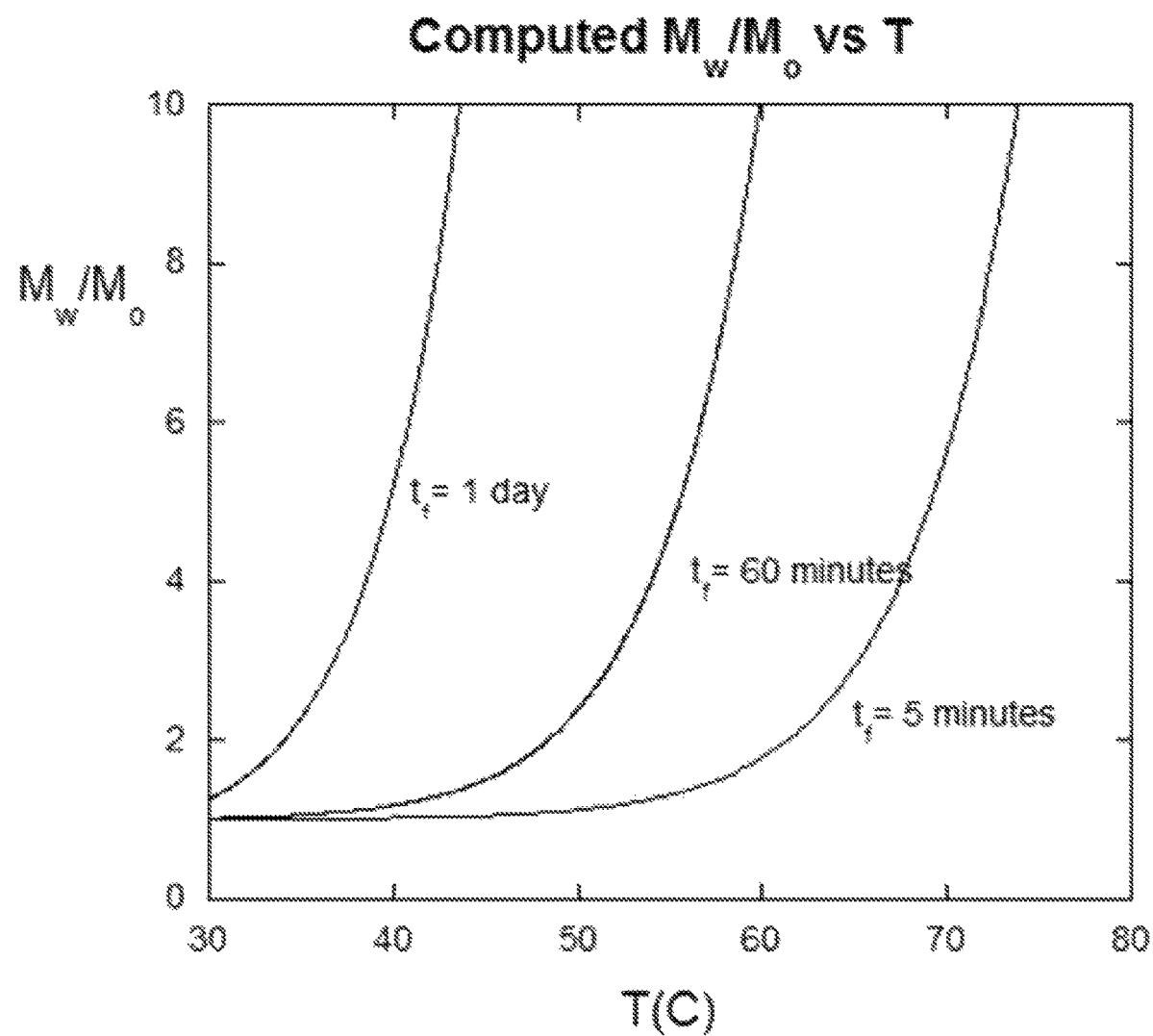
FIG. 1 is an illustration depicting computed $M_w(t)/M_0$ for AR[T(t)] for α-Chymotrypsinogen under a specific pH and ionic strength formulation, according to an example embodiment of the present disclosure.

It should be understood that the various aspects are not limited to the arrangements and instrumentality shown in the drawings.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented. The term "coupled" is defined as connected, whether directly or indirectly through intervening components, and is not necessarily limited to physical connections. The term "communicatively coupled" is defined as connected, either directly or indirectly through intervening components, and the connections are not necessarily limited to physical connections, but are connections that accommodate the transfer of data between the so-described components. The connections can be such that the objects are permanently connected or releasably connected. The term "outside" refers to a region that is beyond the outermost confines of a physical object. The term "axially" means substantially along a direction of the axis of the object. If not specified, the term axially is such that it refers to the longer axis of the object. The terms "comprising," "including" and "having" are used interchangeably in this disclosure. The terms "comprising," "including" and "having" mean to include, but are not necessarily limited to, the things so described.

The term "continuous," with respect to a "continuous measurement" or a sample's ability to be "continuously" measured, refers to a measurement in which no cycle of operations is required between successive measurements, and one in which there is no requirement of a time interval lapse to obtain a successive measurement. For example, the total light scattering from a sample, that may be measured in accordance with the techniques and methods of the present disclosure, can be measured as frequently as desired without any intervening operations. The same is true of measurements such as circular dichroism, circular birefringence, fluorescence, and the pressure drop due to the flow of a viscous liquid across a length of capillary. Important examples of measurements in molecular science that do not meet this definition are dynamic light scattering (DLS) and separation techniques such as HPLC (high pressure liquid chromatography), gel permeation chromatography, gel permeation chromatography (GPC), also referred to as size exclusion chromatography (SEC), and field flow fractionation (FFF). Dynamic light scattering cannot be used for continuous measurements because it must integrate an incoming intensity signal over a finite period of time and then the integral must be reset to zero to make the succeeding measurement. Similarly, GPC (SEC) cannot operate continuously since a new sample must be injected into the system for each measurement, where each measurement involves a time consuming physical separation process generating a chromatogram or set of chromatograms for a given sample. The term "continuous," as used herein, does not require an unbroken record of measurements, instead, measurements can be made as often or as seldom as desired as long as no intervening operations are required or performed. For example, during performance of the presently disclosed methods and techniques, a "continuous system" could make measurements thousands of times per second, or just a few times per second, or with seconds or minutes intervening between measurements.

As used herein, the term "Ansatz," refers to the initial values of one or more key variables used for a first computation of the model-based time dependent light scattering signature (MTS) using the generalized mechanistic model. As used herein, the term "key variables" refers to the values of the rate constants that appear in the generalized mechanistic model, such as $\alpha$, $k_{i,j}$, $k_{n,i}$, appearing in equations 7-10, or in other appropriate equations.

The present disclosure provides a means of determining under what range of conditions a certain mechanism controls aggregation, and under what different ranges of conditions other mechanisms control aggregation, by monitoring $M_w(t)$ and/or $M_{w,agg}(t)$ in realtime via time resolved total intensity light scattering. Additionally, continuous monitoring of intrinsic tryptophan and tyrosine fluorescence as unfolding and aggregation occur provides additional means for distinguishing protein aggregation mechanisms. Establishment of formulation, processing, and storage conditions for protein solutions is accelerated by delineating over which ranges of conditions different mechanisms control protein aggregation. The current technology also allows optimization of stability.

In some embodiments, the current device and methods requires continuous measurement of a property, such as the intensity of scattered light, the absorption of light, circular dichroism (CD) or circular birefringence (CB), fluorescence emission by intrinsic fluorophores (e.g. tryptophan, tyrosine for proteins), or other methods.

The Importance of Time Dependence in Protein Aggregation

The failure to recognize the importance of the time dependence of aggregation can be seen, for example, in the often used representation of light scattering (and other quantities, such as fluorescence) versus temperature rather than versus time. This has led to the spurious notion in the scientific literature of an 'aggregation temperature', '$T_{ag}$'. In fact, protein aggregation can occur over a range of temperatures, so that there is no unique '$T_{ag}$'. Reports on '$T_{ag}$' show light scattering intensity spiking up sharply at a given temperature, which leads to the declaration that '$T_{ag}$' is that specific temperature. In fact, while the instrument is ramping up temperature, the protein solution is in the process of aggregation, so that the rate of temperature change, not the temperature itself, is what determines where the misnomered '$T_{ag}$' will be found.

The absolute intensity of light scattering, together with the protein concentration, yield the weight average molecular weight of all scatterers in the solution, including native protein and aggregates at each instant of time t, $M_w(t)$. The dimensionless quantity $M_w(t)/M_0$ is a convenient means of quantifying time dependent aggregation. $M_0$ is the initial $M_w(0)$ of the scatterers, which corresponds to the molecular weight of the native protein if no aggregates are initially present. The aggregation rate (AR) has been conveniently defined as a dimensionless unit by the slope of the initial linear portion of $M_w(t)/M_0$ versus time, that is $$\text{Aggregation Rate} = AR(s^{-1}) \equiv \frac{d(M_w(t)/M_0)}{dt}\bigg|_{t=0} \quad (1)$$

AR hence represents the fractional increase in aggregate mass per second (See "Simultaneous Multiple Sample Light Scattering (SMSLS) for continuous monitoring of protein aggregation", Michael F. Drenski, Mark L. Brader, and Wayne F. Reed, Chapter 6 in Technologies for Therapeutic Monoclonal Antibody Characterization, Volume 3. Eds. John Schiehl, Oleg Borisov, American Chemical Society, Wash D.C., 2015). AR is exponentially temperature dependent, and normally follows an Arrhenius trend given by $$AR(T) = a\exp\left(\frac{-\Delta E}{k_B T}\right) \quad (2)$$

where a is a constant, $\Delta E$ is the protein activation energy for partial unfolding, $k_B$ is Boltzmann's constant (1.38e-23 J/K) and T is temperature in Kelvin. Hence, $M_w(t)/M_0$ depends on how temperature changes in time T(t), that is $$\frac{M_w(t)}{M_o} = 1 + \int_0^{t_f} AR[T(t)]dt \quad (3)$$

where the integral runs from t=0, when the protein solution begins its heat stress and runs until the heat stress, or monitoring, stops at $t_f$. In the case of AR following an Arrhenius trend $$AR[T(t)] = a\exp\left(\frac{-\Delta E}{k_B T(t)}\right) \quad (4a)$$

FIG. 1 shows computed $M_w(t)/M_0$ for AR[T(t)] for α-Chymotrypsinogen under a specific pH and ionic strength formulation for an experimentally found Arrhenius relationship $$AR[T(t)] = 1.87 \times 10^{24}\exp\left(\frac{-19,800}{k_B T(t)}\right) \quad (4b)$$

and a linear temperature ramp of the form $$T(t) = T_0 + \tau t \quad (5)$$

where the initial temperature was $T_0$=300K and τ is the ramp rate (K/s) and is related to $t_f$ by $$\tau = \frac{T_f - T_o}{t_f} \quad (6)$$

where the final temperature was $T_f$=360K. It is seen that the abrupt rise in $M_w/M_0$, which would be the same trend also for raw intensity of light scattering versus T, depends very strongly on the ramp times, as illustrated for ramp times of 5 minutes, 60 minutes, and 1 day.

Figure 2:
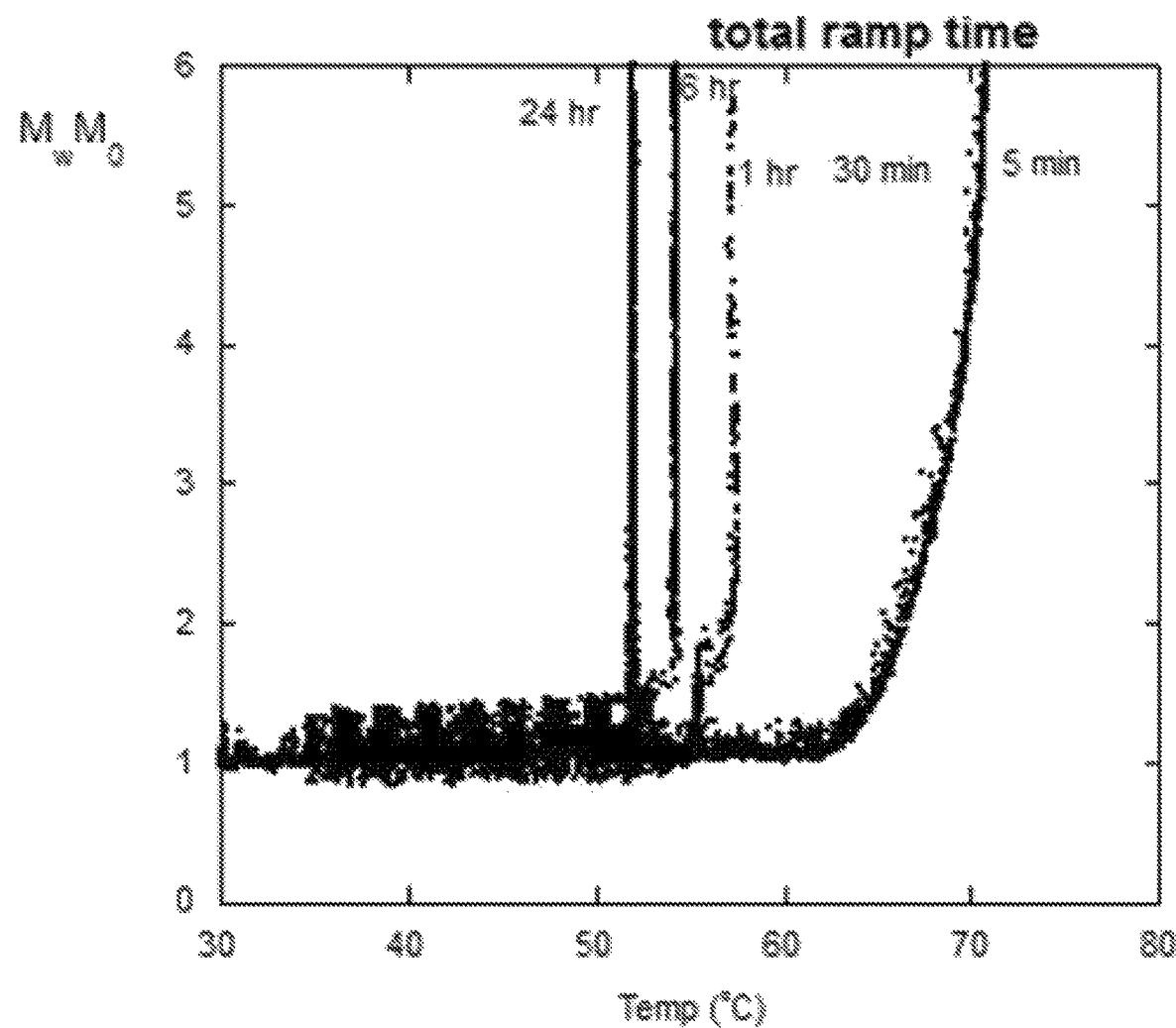
FIG. 2 is an illustration depicting experimental data for α-Chymotrypsinogen, obtained from an APMT Argen unit, where the temperature was ramped over the periods shown from $T_0=300K$ to $T_f=360K$, according to an example embodiment of the present disclosure.

FIG. 2 shows experimental data for α-Chymotrypsinogen, obtained from an APMT Argen unit, where the temperature was ramped over the periods shown from $T_0$=300K to $T_f$=360K. The temperature ramp increased monotonically to $T_f$ but was not linear, hence the data should resemble, but not be identical to, FIG. 1 since a linear temperature ramp in time was used in creating FIG. 1. As can be appreciated, different values of '$T_{ag}$' will be identified according to the temperature ramp period—ranging from '$T_{ag}$'~52 C to '$T_{ag}$'~70 C—thus showing the spurious nature of '$T_{ag}$' as a merely technical quantity related to the instrument's rate of temperature change, and not a fundamental quantity unambiguously related to a single temperature.

Despite the common use of '$T_{ag}$' there have been earlier reports of monitoring the time dependence of protein aggregation using continuous light scattering intensity measurements. See, for example, E. M. Lyutova et al., "Effects of arginine on kinetics of protein aggregation studied by dynamic laser light scattering and tubidimetry techniques", Biotechnology Progress, 23 (2007) 1411-1416; H. Wu et al., "Kinetics of cold-set diffusion-limited aggregations of denatured whey protein isolate colloids", Biomacromolecules, 6 (2005) 3189-3197; Y. Panyukov et al., "The study of amorphous aggregation of tobacco mosaic virus coat protein by dynamic light scattering", Biophysical Chemistry, 127 (2007) 9-18; F. Sokolowski et al., "Formation of critical oligomers is a key event during conformational transition of recombinant Syrian hamster prion protein", Journal of Biological Chemistry, 278 (2003) 40481-40492; M. F. Drenski, W. F. Reed, "Simultaneous Multiple Sample Light Scattering for Characterization of Polymer Solutions", J. App. Polym. Sci., 9 (2004) 2724-2732; and M. F. Drenski et al. "Monitoring Protein Aggregation Kinetics with Simultaneous Multiple Sample Light Scattering (SMSLS)" Analytical Biochemistry, 437 (2013) 185-197, DOI: 10.1016/j.ab.2013.02.014. Widespread adoption of the method in the biotechnology and pharmaceutical communities has yet to occur, and no literature using time dependent forms of scattering from aggregating protein solutions to discern similarities and differences in mechanisms are available.

An advantage of the presently disclosed technology is that it expands beyond the use of the early linear regime of $M_w(t)$ or $M_w(t)/M_0$ to determine AR, and confronts the full non-linear time dependent light scattering aggregation signature and finds a mechanistic model and associated parameters that describe the full non-linear signature.

Kinetic Models for Aggregation

There is considerable evidence that a given protein can aggregate via different kinetic pathways depending upon formulation conditions and the type of stress it receives. For example, the pathway for protein aggregation can be different when comparing stressors such as temperature and stirring. There are further questions as to whether pathways can vary within the range of a given stressor such as, for example, different pathways for different temperatures or for different stir rates, and the specific relationship among these pathways and stressors for different formulation conditions.

There is considerable literature on models for protein aggregation. See, for example, A. M. Morris, M. A. Watzky, and R. G. Finke in "Protein aggregation kinetics, mechanisms, and curve-fitting; A review of the literature". Biochimica et Biophysica Acta, 1794, 2009, 375-397.

The time dependent static light scattering signature (ETS) of an aggregating protein solution represents the time dependent weight average molecular weight produced by the underlying governing kinetic and mass balance equations. A complete set of kinetic equations for irreversible protein aggregation can be formulated as follows: Let N(t) be the number concentration of native proteins at time t (number of native proteins per unit volume), and let $P_1(t)$ be the number concentration of 'activated' proteins; i.e. native proteins that are damaged by unfolding or other means and are hence susceptible to aggregation. In the case of thermal or mechanically induced unfolding the loss rate of N(t) is a first order process, where the loss rate of N(t) is the rate at which $P_1(t)$ is produced.

$$\frac{dN}{dt} = -\alpha N \tag{7}$$

(In the case of purely colloidal instability of native proteins, i.e. in the case where native proteins can aggregate without damage, then $P_1(t)=N(t)$ and equation 7 is no longer relevant)

Let $P_i(t)$ be the number concentration of aggregates containing i proteins, whether damaged or native. Then, from mass balance $P_1(t)$ can be written as $$\frac{dP_1}{dt} = \alpha N - 2k_{1,1}P_1^2 - P_1 \sum_{j=2}^{N_{max}} k_{1,j}P_j - k_{N,1}NP_1 \tag{8}$$

The factor of '2' occurs in the $P_1^2$ term because two $P_1$ objects are lost when they stick together to form a single $P_2$ object. The $k_{1,j}$ in the summation term express the probability of $P_1$ irreversibly sticking to $P_h$ in a collision. The $k_{N,1}$ term admits the possibility that an undamaged protein could stick to $P_1$ in a collision. $N_{max}$ is the largest number of proteins in an aggregate. For self-limited dimerization $N_{max}=2$, whereas for unlimited colloidal growth $N_{max}$ tends towards infinity.

The expression for $P_i$ for i>2 is expressed as $$\frac{dP_i}{dt} = -2k_{i,i}P_i^2 - P_i \sum_{\substack{j=1 \\ j \neq i}}^{N_{max}} k_{i,j}P_j + \sum_{j=1}^{Int(i/2)} k_{j,i-j}P_jP_{i-j} - k_{N,i}NP_i \tag{9}$$

It is assumed in equations 8 and 9 that aggregates grow chiefly by two body collisions; i.e. the solutions are dilute enough that two body collisions dominate. In the case where three body collisions become important terms of the form $k_{i,j,k}P_iP_jP_k$ need to be added.

In the case where native proteins cannot aggregate then $k_{N,i}=0$ for all i. On the other hand, if native proteins can aggregate and if they aggregate with different probabilities according to the composition of an aggregate in terms of how many damaged proteins j are in it and how many native proteins m are in it, then such a compound aggregate can be designated as $P_{j,m}$ and the corresponding constants as $k_{N,j,m}$ for addition of native monomers and as $k_{k,p,j,m}$ for an aggregate $P_{k,p}$ sticking to an aggregate $P_{j,m}$ upon collision. In these cases the $k_{N,i,m}$ and $k_{k,p,j,m}$ can depend on the sequence in which damaged and native proteins were added to an aggregate. In this case the constants are no longer a fixed matrix of values, but rather a dynamically determined array whose values depend on the history of the aggregation. The aggregation is a non-Markovian process in this case since the set of all k constants at a given time depend on the path by which the current state of the system was reached. A parallel to this in polymer science is an ideal random coil polymer with no excluded volume, which is Markovian, versus the case of excluded volume, where the spatial placement of a monomer j after j-1 monomers have been placed in the chain depends on the spatial placement of all previous j-1 monomers. This latter process is non-Markovian and has generated large amounts of literature seeking solutions. See, for example, Hiromi Yamakawa "Modern Theory of Polymer Solutions", 1971, Harper & Row, London. The possibility of adapting the current present technology to the non-Markovian case exists but is not pursued here.

For the Markovian case, i.e. where the matrix $k_{k,p,j,m}$ is definable and not history dependent, then equation 9 can be extended to $$\frac{dP_{k,p}}{dt} = -2k_{k,p,k,p}P_{k,p,k,p}^2 - P_{k,p} \sum_{\substack{m=1 \\ m,j \neq k,p}} \sum_{j=1} k_{p,k,j,m}P_{j,m} + \tag{10}$$

$$\sum_{m=1}^{Int(N_{max}/2)} \sum_{j=1}^{Int(N_{max}/2)} k_{j,k-j,m,p-m}P_{j,k}P_{k-j,p-m} - k_{N,k,p}NP_{k,p}$$

For the purposes of illustration of the present technology, the following will stay restricted to the case of equations 7-9. For any specific irreversible mechanism described by equation 7-9 the key variables $k_{i,j}$ and $k_{N,i}$ form a set. The set can describe mechanisms such as self-limiting aggregation which ends at a certain number of proteins per aggregate, 'chain growth' addition of native monomers and or $P_1$, unlimited growth which is neutral (all $k_{i,j}$ of same or similar values), cooperative ($k_{i,j}$ increasing as i and j increase), or anti-cooperative ($k_{i,j}$ decreasing as i and j increase).

Whereas the above formulation has been made for irreversible aggregation, this is not limiting, since it is straightforward to include equilibrium conditions between different state of aggregation, such as an equilibrium between native and activated monomeric states, and equilibria between native and activated monomers and oligomers, such as dimers and tetramers, and equilibria between oligomers. Such equilibria are represented by standard notation such as, not limiting, $$N \underset{k_b}{\overset{k_f}{\rightleftarrows}} P_1,$$

for which the equilibrium constant $K_{eq}=P_1/N$ gives the ratio of moles of monomer in the activated monomeric state to native monomer.

Time Dependent Light Scattering Signatures (TLS) Associated with Solutions to Equations 7-9

Given a set of $k_{i,j}$ for a specific mechanism the continuous detection means, such as total intensity light scattering, fluorescence, CD, CB, etc. will produce a specific time-dependent signature. Here, the TLS from continuous monitoring of total intensity light scattering from aggregating proteins is considered. When the TLS is experimentally measured it is termed the ETS, short for experimental time dependent light scattering signature. When a TLS is computed with equations 7-9 with specific key variable values then the resulting signature is termed the MTS, short for model based time dependent light scattering signature.

The total excess light scattering from a solution containing scattering molecules is frequently expressed in terms of the absolute Rayleigh scattering ratio $I_R$. This involves measuring the scattering from the solution, subtracting the pure solvent baseline (this subtraction can be ignored if the solution scattering is much greater than that of the solvent). $I_R$ can be determined by relating the measured scattering intensity to the scattering intensity from a well known standard, such as toluene. Calibration can also be achieved using molecular weight standards. A thorough description of solvent based calibration is given, for example in F. H. Florenzano, R. Strelitzki, W. F. Reed, "Absolute, Online Monitoring of Polymerization Reactions", Macromolecules, 31, 7226-7238, 1998.

Once $I_R(q)$ is determined for one or more scattering angles $\theta$ where $q=(4\pi n/\lambda)\sin(\theta/2)$ the well known Zimm equation can be used to determine the weight average molecular weight $M_w(t)$ of the scatterers and the radius of gyration at each instant of time that a light scattering measurement is made. See, for example, Florenzano et al. cited above.

$M_w(t)$ is related to the number concentrations $P_i(t)$ and $N(t)$ in the usual manner $$M_w(t) = M_0 \frac{N(t) + \sum_i i^2 P_i(t)}{N(t) + \sum_i i P_i(t)} = M_0 \frac{N(t) + \sum_i i^2 P_i(t)}{N(0)} \quad (11)$$

where $M_0$ is the molar mass of the native protein and $N(0)$ is the initial number concentration of native protein. Conservation of mass gives $N(0)$ equal to the mass concentration of all aggregates plus remaining native protein, when no dilution or concentration of the solution occurs. If a change in concentration of the solution occurs then the total initial mass of native protein equals the sum of all aggregates and remaining native protein at any time later. The total mass of native proteins is $M_0 N(0) V(0)$, where $V(0)$ is the initial volume of the solution. This average involves both the native proteins and the aggregates. The weight average molar mass of the aggregates alone, $M_{w,ag}$, is given by $$M_w(t) = M_0 \frac{\sum_i i^2 P_i(t)}{\sum_i i P_i(t)} = M_0 \frac{\sum_i i^2 P_i(t)}{N(0) - N(t)} \quad (12)$$

where the concentration of aggregate in the denominator $N(0)-N(t)$ cannot be determined by light scattering alone, and is typically determined by discrete GPC injections. However, angular dependent light scattering can distinguish between a large population of small scatterers and a small population of large scatterers, each of which can yield the same $M_w(t)$ in the following way: Native proteins are generally Rayleigh scatterers, i.e. they have diameters much smaller than the incident light used for scattering experiments and so scatter light equally at all angles in the scattering plane. Hence, in the case of a large population of small scatterers (e.g. dimers, trimers, tetramers, etc.) there will be no angular dependence in the scattered light, whereas a small population of large scatterers (composed of hundreds, thousands, or more proteins in an aggregate) will yield a measurable angular dependence.

Figure 3:
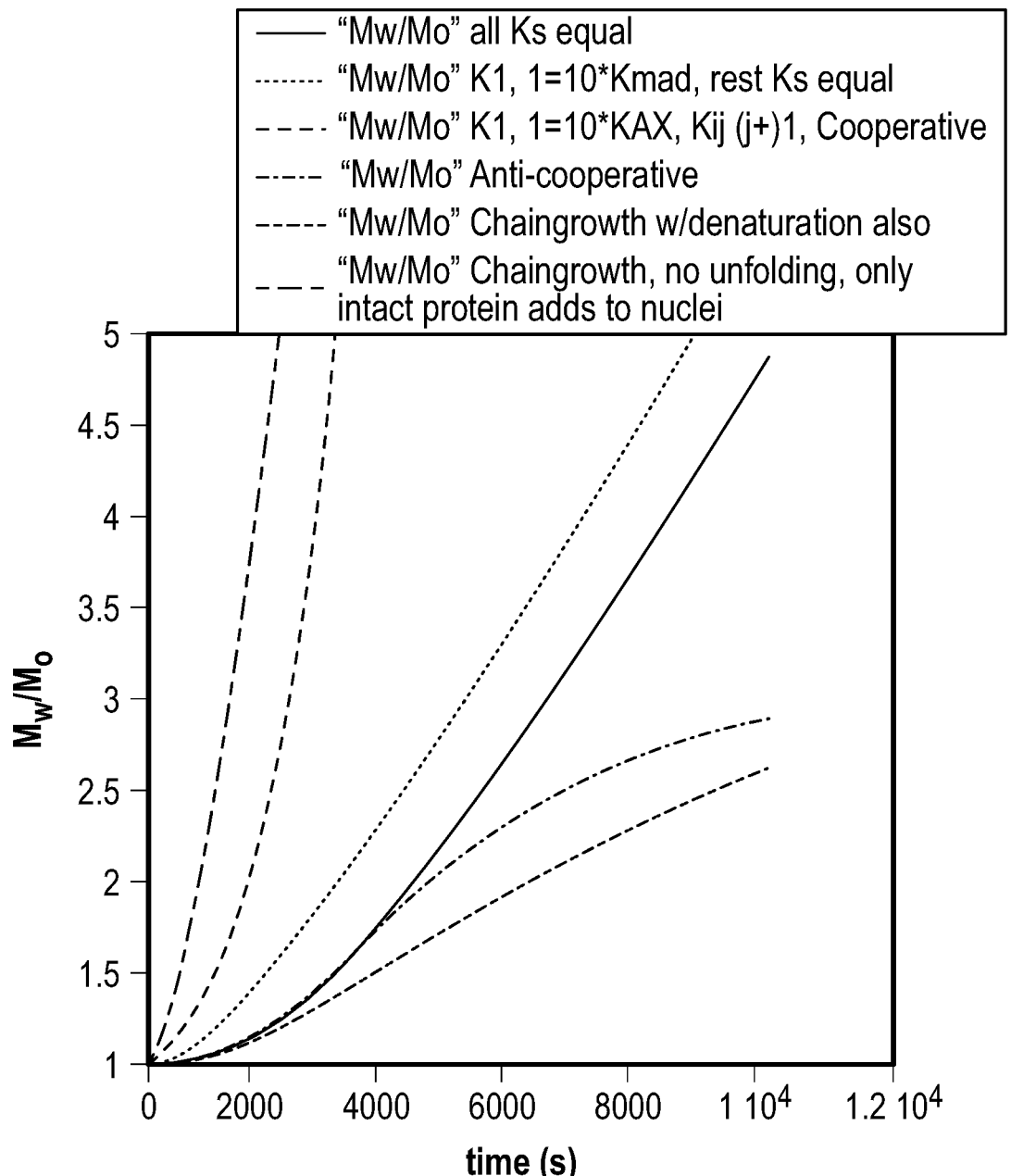
FIG. 3 is an illustration depicting a variety of time dependent light scattering signatures (TLS) under different mechanistic scenarios, according to an example embodiment of the present disclosure.

FIG. 3 shows a variety of TLS under different mechanistic scenarios, such as those mentioned above. While these are all monotonically increasing some show inflection points and all show different degrees of steepness and details of shape.

Figure 4:
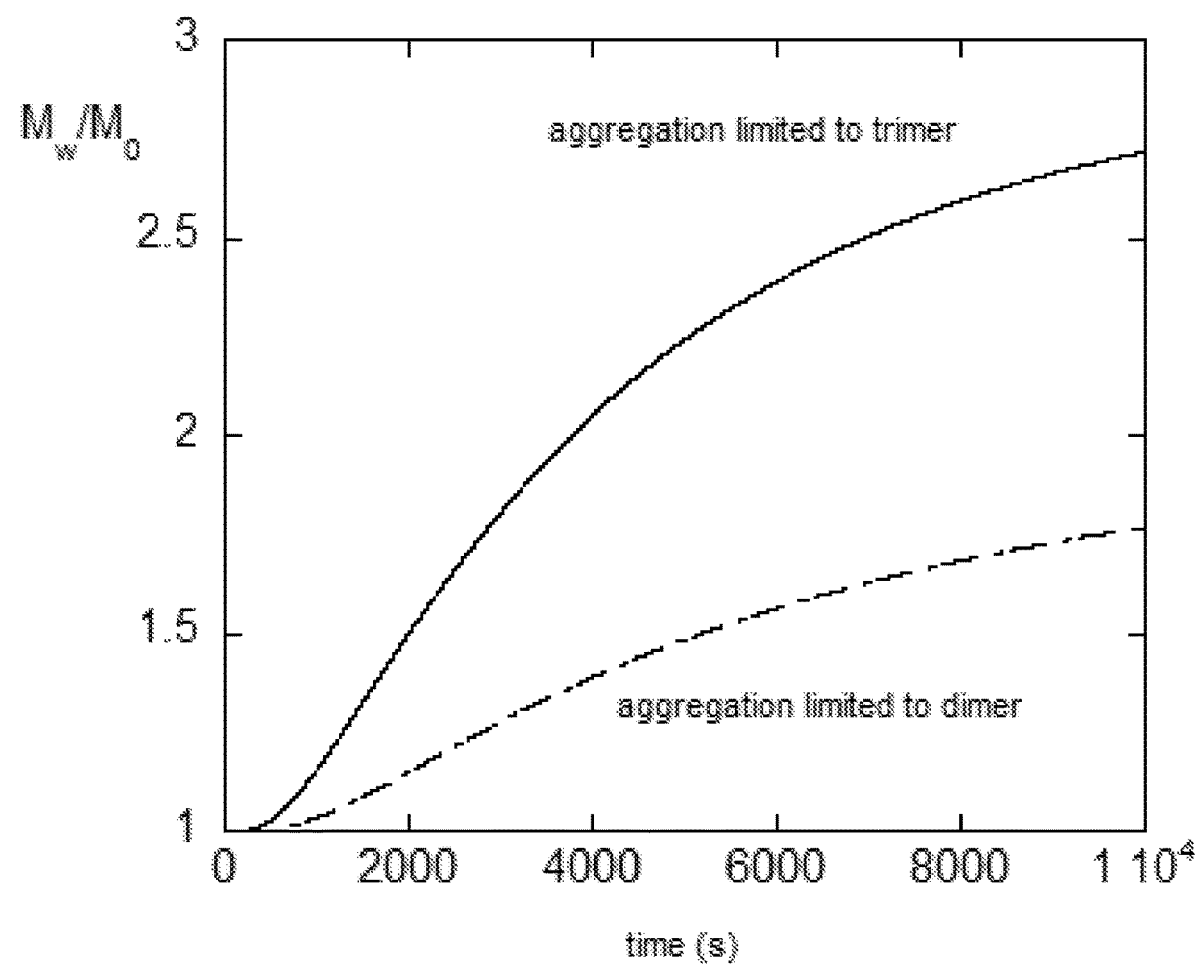
FIG. 4 is an illustration depicting additional TLS cases where aggregation is self-limiting to dimers in one case and trimers in the second case, according to an example embodiment of the present disclosure.

FIG. 4 shows some additional TLS cases where aggregation is self-limiting to dimers in one case and trimers in the second case.

Identifying Protein Aggregation Mechanisms from Time Dependent Light Scattering Signatures The present disclosure provides for identification of protein aggregation mechanisms from ETS, experimental time dependent light scattering signatures. In some embodiments light scattering intensity data from a macromolecular solution changing in time are gathered continuously in time in order to produce an experimental time dependent light scattering signature (ETS).[1] A generalized mechanistic model (GMM) comprising a system of mass balance and kinetic equations, such as, but not limited to, Equations 7-9, containing key variables is then used to generate a model-based time dependent light scattering signature (MTS) based on the set of key variables. The key variables of the GMM are varied until the MTS matches the ETS. The values of the key variables used in the match then specify the mechanism by which protein aggregation is occurring. One of the main uses of the present technology is to optimize the formulation conditions for biological molecules such as proteins used in biologic drugs.

The present technology can be used during realtime acquisition of ETS and optimized key variable sets for MTS can be generated in realtime, elucidating how features of the mechanism evolve in time. The present technology can also be used retrospectively on ETS, after an ETS is gathered, for determining the key variables in matching MTS.

For example, a certain formulation variable such as ionic strength (IS) may lead to cooperative aggregation, whereas another IS may lead to anti-cooperative aggregation. The differences are reflected in the set of key variables in the MTS found for each ETS. As used herein, the term "key variables" refers to the values of the rate constants that appear in the generalized mechanistic model, such as $\alpha$, $k_{i,j}$, $k_{n,i}$, appearing in equations 7-10, or in other appropriate equations. Anti-cooperative aggregation gives higher formulation stability than cooperative aggregation so the latter IS would be favored in developing a formulation. The same type of ETS/MTS procedure could be used with different proteins—e.g. different mutagenic strains—under identical formulation conditions to determine which protein is more robust.

In some embodiments, it is also possible to identify similarity of mechanism of protein aggregation by superposing two ETS from two separate aggregation process with a single parameter transformation of the time axis between them. If two ETS can be superposed onto each other with the single parameter transformation for a given time interval then the mechanism represented by the single parameter transformation is the same for both ETS. Deviations from superposability between ETM and the single parameter transformation reveal differences in mechanism and can be used to 'steer' the formulation to the optimum conditions by making appropriate changes in formulation conditions.

Figure 5:
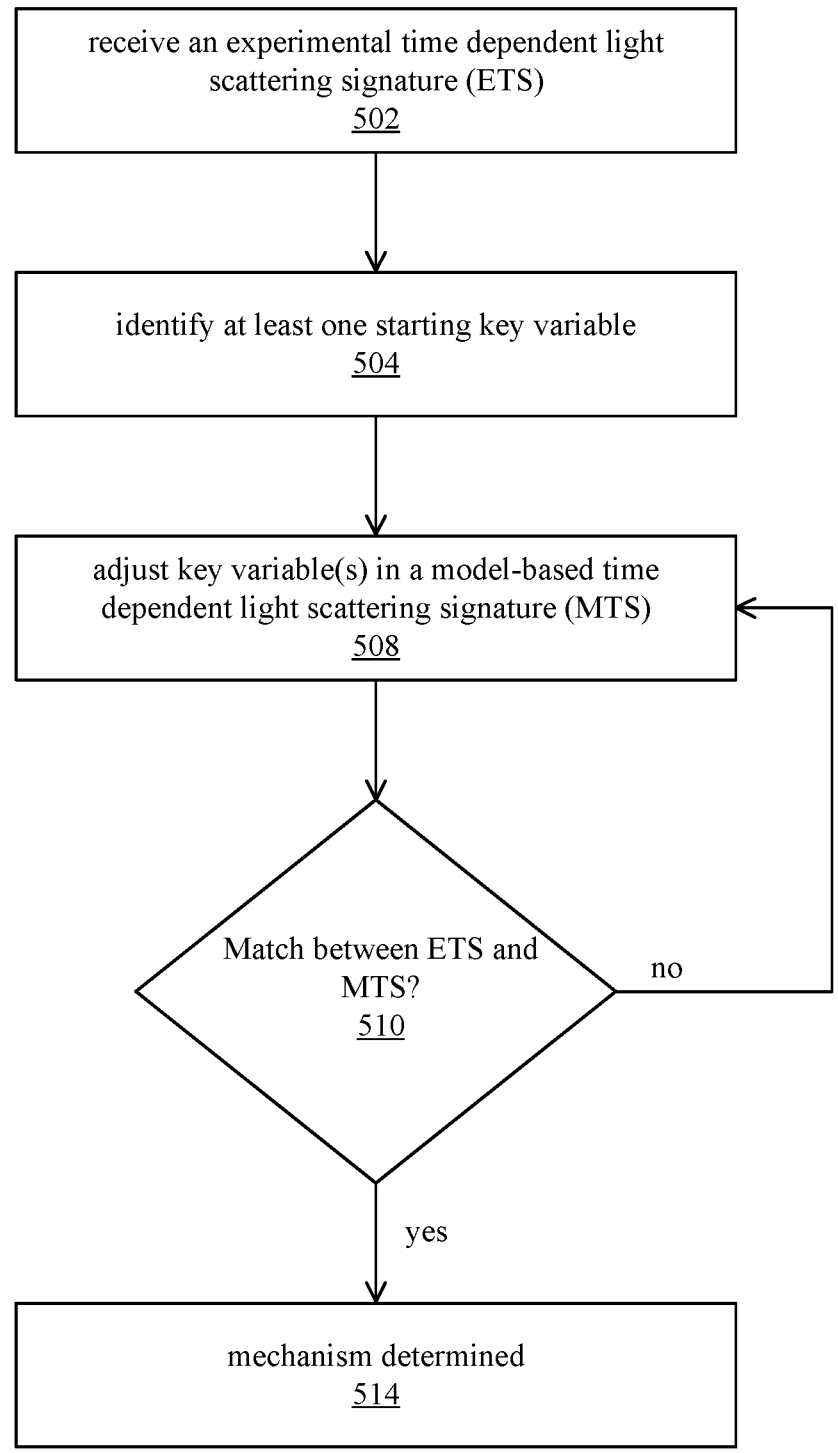
FIG. 5 is an illustration depicting a method for determining a mechanism of protein aggregation for a sample solution characterized by an experimental time dependent light scattering signature, according to an example embodiment of the present disclosure.
Figure 6:
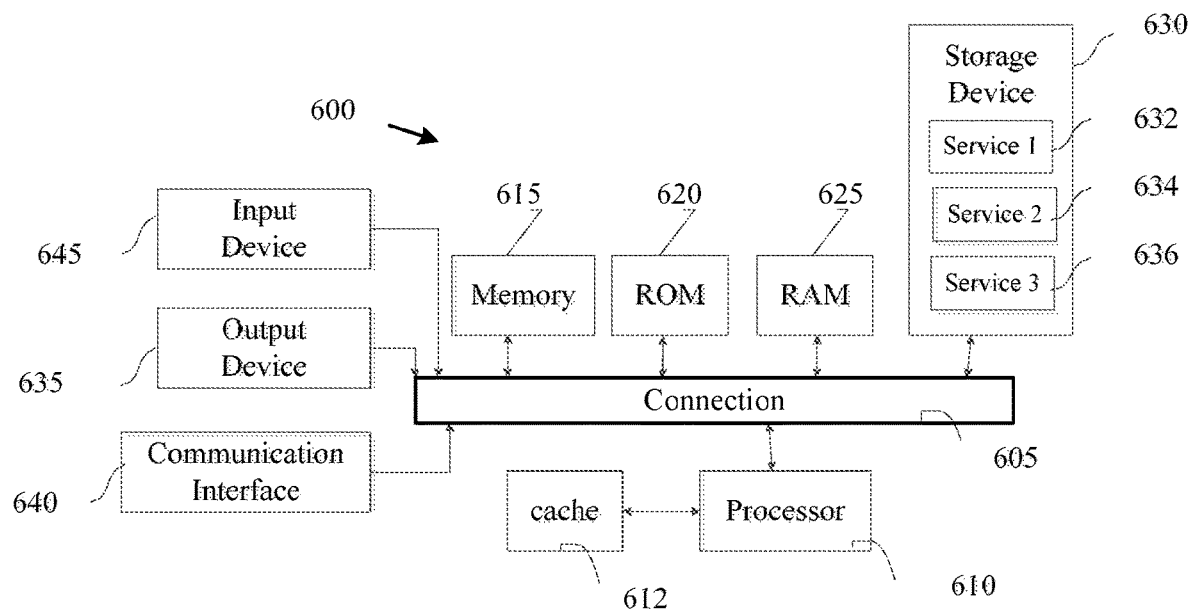
FIG. 6 is a diagram of a computing system capable of performing the presently disclosed techniques and methods, according to an example embodiment of the present disclosure.

FIG. 5 illustrates an example method embodiment for determining a mechanism of protein aggregation for a sample solution characterized by an experimental time dependent light scattering signature according to the present technology. In some embodiments, the example method shown is performed using a computing system such as illustrated in FIG. 6, performed by SMSLS device illustrated in FIG. 7, or a combination of systems.

As illustrated in FIG. 5, and addressed herein, the computing system can receive (502) an experimental time dependent light scattering signature (ETS). The ETS is made up of experimental data descriptive of an average molecular weight of protein components in a solution over time. In some embodiments, the ETS is comprised of continuous measurements of the sample over time.

As addressed above, mechanisms explaining aggregation of proteins in a sample solution can be complex. In theory there can be an infinite number of aggregation mechanisms interacting together. In reality the number of proteins in an aggregate is likely to be between 1-100. In other words, in equation 9 i and j are most commonly between 1-100, where j is the number of proteins in the aggregate whose number concentration is $P_j$ and i is the number of proteins in the aggregate whose number concentration is $P_i$. This still leaves a large number of possible combinations of aggregation mechanisms to be considered. In some cases, where a small population of large aggregates dominate the aggregation process i and j can be much greater than 100.

In order to accommodate such complexity, in some embodiments, a database of example model signatures based off a generalized mechanism model (GMM) can exist; the database of protein aggregation mechanisms that have been modeled and characterized. Such a database of example model signatures can be useful to identify (504) an Ansatz for evaluating the experimental time dependent light scattering signature. In embodiments wherein model signatures exist, one of the model signatures with specified key variables can be selected to be the Ansatz.

A database of example model signatures is not required by the present technology. In embodiments wherein there is not an example model signatures, the computing system can identify (504) an Ansatz based on equations 7-9 (which define the generalized mechanistic model for protein aggregation in the present technology) using known curve fitting techniques.

There are many ways of establishing an Ansatz known in the art. However, several approaches are described herein.

The value of α in equation 7 is the Aggregation Rate (AR) defined in equation 1 and so can be determined experimentally from the early portion of the ETS. A strategy for finding the set of $k_{i,j}$ values involves first scrutinizing the ETS, whether by a human or machine code, or machine learning code, and determining the 'class' that the ETS falls in. One example of a class is chain growth; i.e. adding only native monomers and/or denatured monomers to aggregates, for which $k_{i,j}$ are finite but $k_{i,j}=0$ for i>1. For instance, examples of the chain growth mechanistic class are shown in FIG. 3, along with a variety of other time dependent light scattering signatures under different mechanistic scenarios, such as self-limiting growth, cooperative growth, and anti-cooperative growth. Self-limiting growth can be ascertained by the ETS asymptotically approaching a finite value. FIG. 4 shows examples of ETS where aggregation is limited in one case to dimers and another where it is limited to trimers. If the highest aggregate that can form is $N_{max}$ then $k_{i,j}=0$ for all $i+j>N_{max}$. As depicted in FIG. 3, if the ETS is concave upwards (positive second time derivative) then the ETS is a candidate for cooperative growth. In such cases, $k_{i,j}$ increases with increasing i,j. On the other hand, if the ETS is concave downwards it is a candidate for anti-cooperative growth. In the case of anti-cooperative growth, $k_{i,j}$ decreases with increasing i and j.

The way in which $k_{i,j}$ change with i and j is model dependent. For example, if one considers the probability for 'sticking' upon diffusion controlled collisions in the Smoluchowski model, this is proportional to $(D_i+D_j)(R_i+R_j)$, where $D_i$ and $D_j$ are the diffusion coefficients of objects i and j, respectively, and $R_i$ and $R_j$ are their effective radii. The D's and R's depend on the morphology of the aggregates. As an example, if the aggregates are globular and resemble spheres, then, by the Stokes-Einstein equation $R=k_B T/6\pi\eta D$, where $k_B$ is Boltzmann's constant and η is the solution viscosity so that $$k_{i,j} \propto 2 + \left(\frac{i}{j}\right)^{1/3} + \left(\frac{j}{i}\right)^{1/3} \qquad (13)$$

However, effective radii need not literally be the physical radius of a colliding object, just as in nuclear physics the effective cross-section for colliding objects can be less or more than the actual physical cross sections. For protein aggregates unfolding or 'sticky' sites can accumulate on the surface or get buried in the aggregate's interior. In the former case the probability of sticking would increase as the density of sticky sites on an aggregate increases, leading to cooperative growth. Conversely, in the second case sticky sites could get sequestered away from the surface leading to anti-cooperative growth. The exponent of '⅓' is not limiting since other morphologies lead to different exponents. For example, an ideal random coil has an exponent of ½, whereas other structures can have different fractal dimensions. A protein aggregate is expected to lie between ⅓ and ½. Feder, Jossang, and Rosenqvist in Physical Review Letters, 1984, 53, 1403-1406, reported an exponent of 0.391 for antibody aggregates they studied.

As the classes of ETS become more sharply defined the types of Ansatz will likewise become more defined. Machine learning will accelerate the process of defining and differentiating Ansatze.

Identifying (504) the Ansatz provides a starting key variable set. The Ansatz is based on equations 7-9 (which define the generalized mechanistic model for irreversible protein aggregation in the present technology). The Ansatz being an initial value of one or more key variables used for a first computation of the MTS using the GMM.

After identifying (504) the key variable (or key variable set), the computing system can adjust the at least one key variable (or key variable set) in the initial GMM until a final MTS is identified. In some embodiments the computing system can adjust the key variable(s) at the direction of an operator. In some embodiments the computing system can adjust the key variables) using a curve fitting algorithm.

The computing system can iteratively compare (508) the ETS and MTS using statistical analysis to determine when the MTS and the ETS sufficiently match (510). There are a number of means for finding the set of $k_{i,j}$ that will lead to the best match between ETS and MTS. A convenient parameter for goodness of fit, is 'chi-squared' over N time points for an aggregation process:

$$\chi^2 = \frac{1}{N}\sum_{j=1}^{N}[ETS(t_j) - MTS(t_j)]^2 \qquad (14)$$

A 'brute force' approach to optimization is to perform a grid search, by taking the Ansatz values of all $k_{i,j}$ and forming a search grid, where each $k_{i,j}$ varies within a certain amount of its Ansatz value and then is subdivided into intervals, not necessarily equally spaced. For example, not limiting, say the Ansatz value of $k_{3,6}=1$. Then one might set up limits, not limiting, from $k_{3,6}=0.1$ to 10 and space them logarithmically, using a total of 11 values. This is shown table 1.

TABLE 1

| log(k3, 6) | k3, 6 |
|---|---|
| −1 | 0.100 |
| −0.8 | 0.158 |
| −0.6 | 0.251 |
| −0.4 | 0.398 |
| −0.2 | 0.631 |
| 0 | 1.000 |
| 0.2 | 1.585 |
| 0.4 | 2.512 |
| 0.6 | 3.981 |
| 0.8 | 6.310 |
| 1 | 10.000 |

All the other values of $k_{i,j}$ are given limits and intervals of their own, which need not be the same among them, and a search grid is thence formed. The search is made by fixing the grid values of all but one $k_{i,j}$ then finding at which point the best value of 'chi-squared' or other goodness of fit criterion occurs. The procedure is then repeated for all the other $k_{i,j}$ one at a time, until a coarse optimization is achieved. The new $k_{i,j}$ values are then given limits and intervals and a finer search performed. Further iterations of finer searches can subsequently be performed, for example, until a target value of 'chi-squared' or other goodness of fit criterion or criteria is (are) reached. If i and j get large the grid search could become time consuming on an ordinary desktop computer, which might require either using a more powerful computer, or constraining the number of $k_{i,j}$ used. Normally, when ETS are gathered $M_w/M_0$ is followed up until somewhere in the range of 2 to 50 (not limiting). Depending on the mechanism it may be possible to significantly lower the number of $k_{i,j}$ used. Another issue is that in a multivariable space there are normally many minima, so that extra care must be made to assure that the minimum found is the absolute minimum and not just a local minimum. One way to do this is by using significantly different Ansatz sets of $k_{i,j}$ for multiple analyses of a given ETS. The issue may also arise that more than one minimum yields the same 'chi-squared' or other goodness of fit criterion or criteria within the experimental error of the system. In such a case it could be necessary to assign 'diagnostic probabilities'; i.e. there would be a certain probability of the ETS belonging to more than one mechanistic set of $k_{i,j}$.

Another means of finding the optimal set of $k_{i,j}$ for a given Ansatz is a so-called gradient search. In this procedure, for which many different embodiments exist, the difference in 'chi-squared' of other goodness of fit criterion or criteria is measured when one of the $k_{i,j}$ is incremented upwards or downwards while holding the others constant. The direction (up or down from the current value of $k_{i,j}$) which improves the fit criterion(a) is then chosen the next time an iteration on that particular $k_{i,j}$ is made. The $k_{i,j}$ and direction yielding the improved value can be stored and the procedure then applied to the other $k_{i,j}$ until a first iteration has found the downhill gradient for each $k_{i,j}$ and then the procedure can be repeated, again sweeping through all $k_{i,j}$ in the previously found direction. The amount the $k_{i,j}$ is stepped in the downward gradient direction can be varied from iteration to iteration. Avoiding local minima can be achieved by using an extended gradient search; e.g. 'climbing' out of the local minimum and seeking other gradients to go down in the space of $k_{i,j}$. Use of different Ansatz for an ETS can also help avoid local minima. Many search algorithms exist in the literature. See, for example, 'Data Reduction and Error Analysis for the Physical Sciences', $3^{rd}$ Ed., P. B. Bevington & D. K. Robinson, McGraw Hill, 2003.

When the ETS and the MTS sufficiently match (510) the adjusting of the key variables can cease and the MTS can be considered a final MTS for the ETS. When the ETS and the MTS do not sufficiently match (510) the computing system can continue to iteratively adjust (508) the key variable(s).

When the final MTS that sufficiently matches the experimental time dependent light scattering signature has been identified, the final MTS identifies at least one protein aggregation mechanism (514) that explains the protein aggregation mechanism observed in the ETS.

In some embodiments the method illustrated in FIG. 5 can be used both offline (i.e. after the aggregation data are collected) or online, during data collection.

FIG. 6 shows an example of computing system 600 in which the components of the system are in communication with each other using connection 605. Connection 605 can be a physical connection via a bus, or a direct connection into processor 610, such as in a chipset architecture. Connection 605 can also be a virtual connection, networked connection, or logical connection.

In some embodiments computing system 600 is a distributed system in which the functions described in this disclosure can be distributed within a datacenter, multiple datacenters, a peer network, etc. In some embodiments, one or more of the described system components represents many such components each performing some or all of the function for which the component is described. In some embodiments, the components can be physical or virtual devices.

Example system 600 includes at least one processing unit (CPU or processor) 610 and connection 605 that couples various system components including system memory 615, such as read only memory (ROM) and random access memory (RAM) to processor 610. Computing system 600 can include a cache of high-speed memory connected directly with, in close proximity to, or integrated as part of processor 610.

Processor 610 can include any general purpose processor and a hardware service or software service, such as services 632, 634, and 636 stored in storage device 630, configured to control processor 610 as well as a special-purpose processor where software instructions are incorporated into the actual processor design. Processor 610 may essentially be a completely self-contained computing system, containing multiple cores or processors, a bus, memory controller, cache, etc. A multi-core processor may be symmetric or asymmetric.

To enable user interaction, computing system 600 includes an input device 645, which can represent any number of input mechanisms, such as a microphone for speech, a touch-sensitive screen for gesture or graphical input, keyboard, mouse, motion input, speech, etc. Computing system 600 can also include output device 635, which can be one or more of a number of output mechanisms known to those of skill in the art. In some instances, multimodal systems can enable a user to provide multiple types of input/output to communicate with computing system 600. Computing system 600 can include communications interface 640, which can generally govern and manage the user input and system output. There is no restriction on operating on any particular hardware arrangement and therefore the basic features here may easily be substituted for improved hardware or firmware arrangements as they are developed.

Storage device 630 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read only memory (ROM), and/or some combination of these devices.

The storage device 630 can include software services, servers, services, etc., that when the code that defines such software is executed by the processor 610, it causes the system to perform a function. In some embodiments, a hardware service that performs a particular function can include the software component stored in a computer-readable medium in connection with the necessary hardware components, such as processor 610, connection 605, output device 635, etc., to carry out the function.

For clarity of explanation, in some instances the present technology may be presented as including individual functional blocks including functional blocks comprising devices, device components, steps or routines in a method embodied in software, or combinations of hardware and software.

Any of the steps, operations, functions, or processes described herein may be performed or implemented by a combination of hardware and software services or services, alone or in combination with other devices. In some embodiments, a service can be software that resides in memory of a client device and/or one or more servers of a content management system and perform one or more functions when a processor executes the software associated with the service. In some embodiments, a service is a program, or a collection of programs that carry out a specific function. In some embodiments, a service can be considered a server. The memory can be a non-transitory computer-readable medium.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, solid state memory devices, flash memory, USB devices provided with non-volatile memory, networked storage devices, and so on.

Devices implementing methods according to these disclosures can comprise hardware, firmware and/or software, and can take any of a variety of form factors. Typical examples of such form factors include servers, laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

Figure 7:
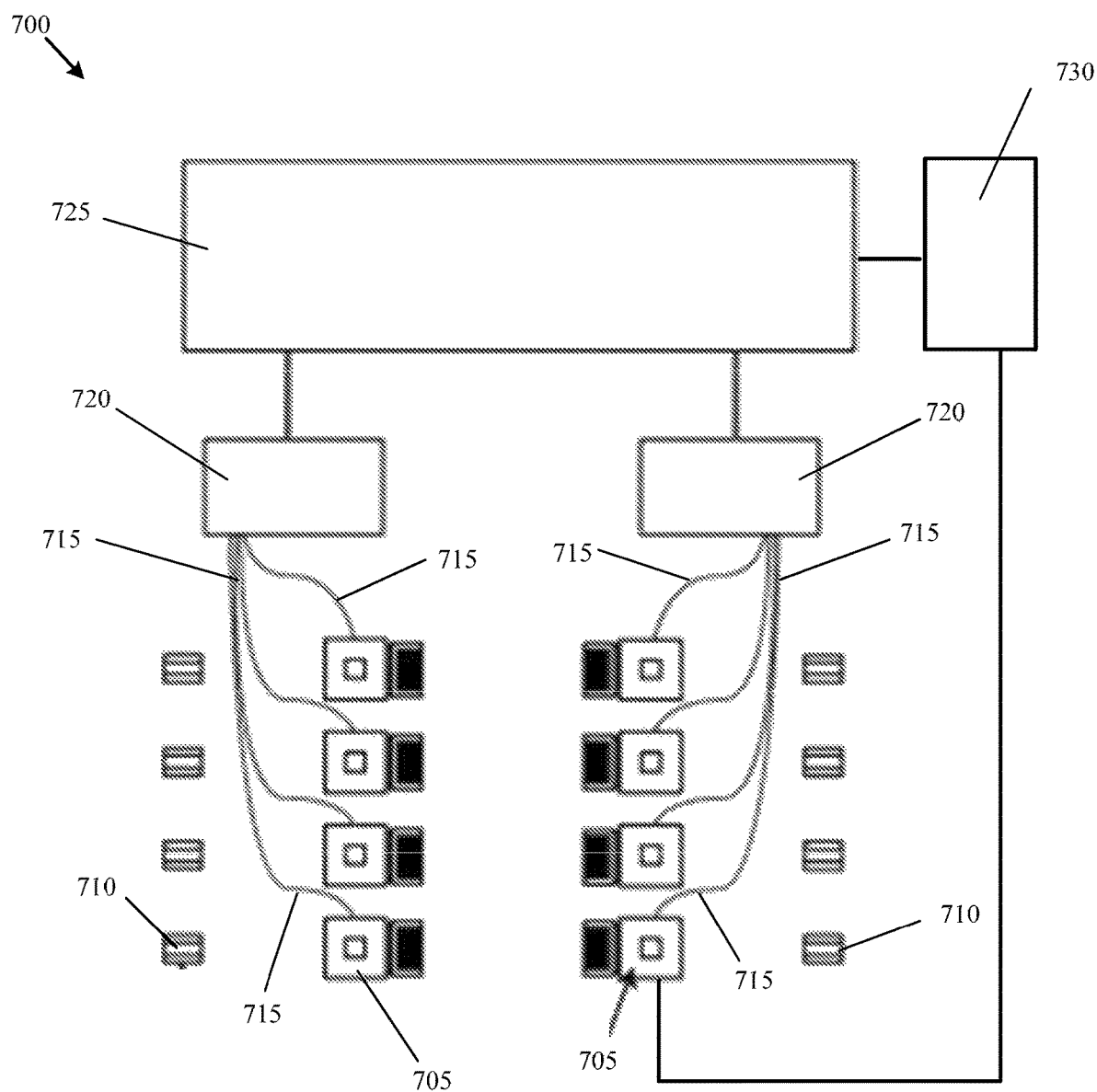
FIG. 7 is a diagram of a SMSLS device and system capable of performing the presently disclosed techniques and methods, according to an example embodiment of the present disclosure.
Figure 8:
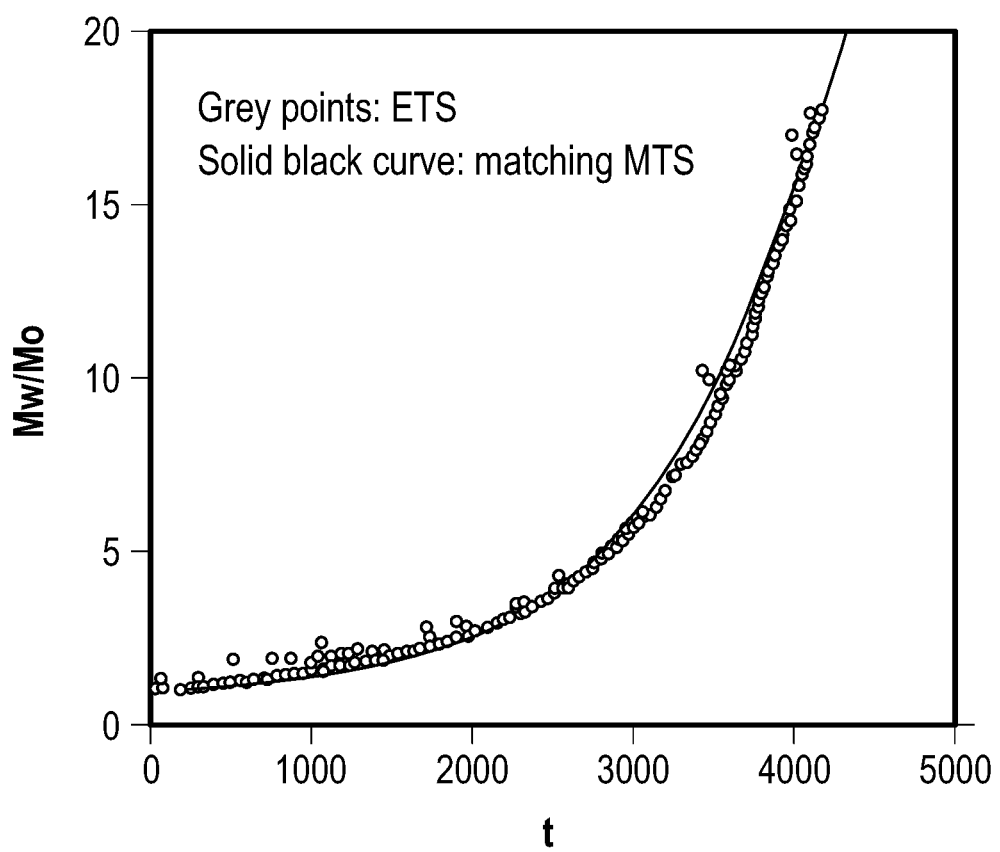
FIG. 8 is an illustration depicting real data ETS and corresponding MTS from the numerical solutions of equations 7-9 with specific sets of $k_{i,j}$, according to an example embodiment of the present disclosure.
Figure 9:
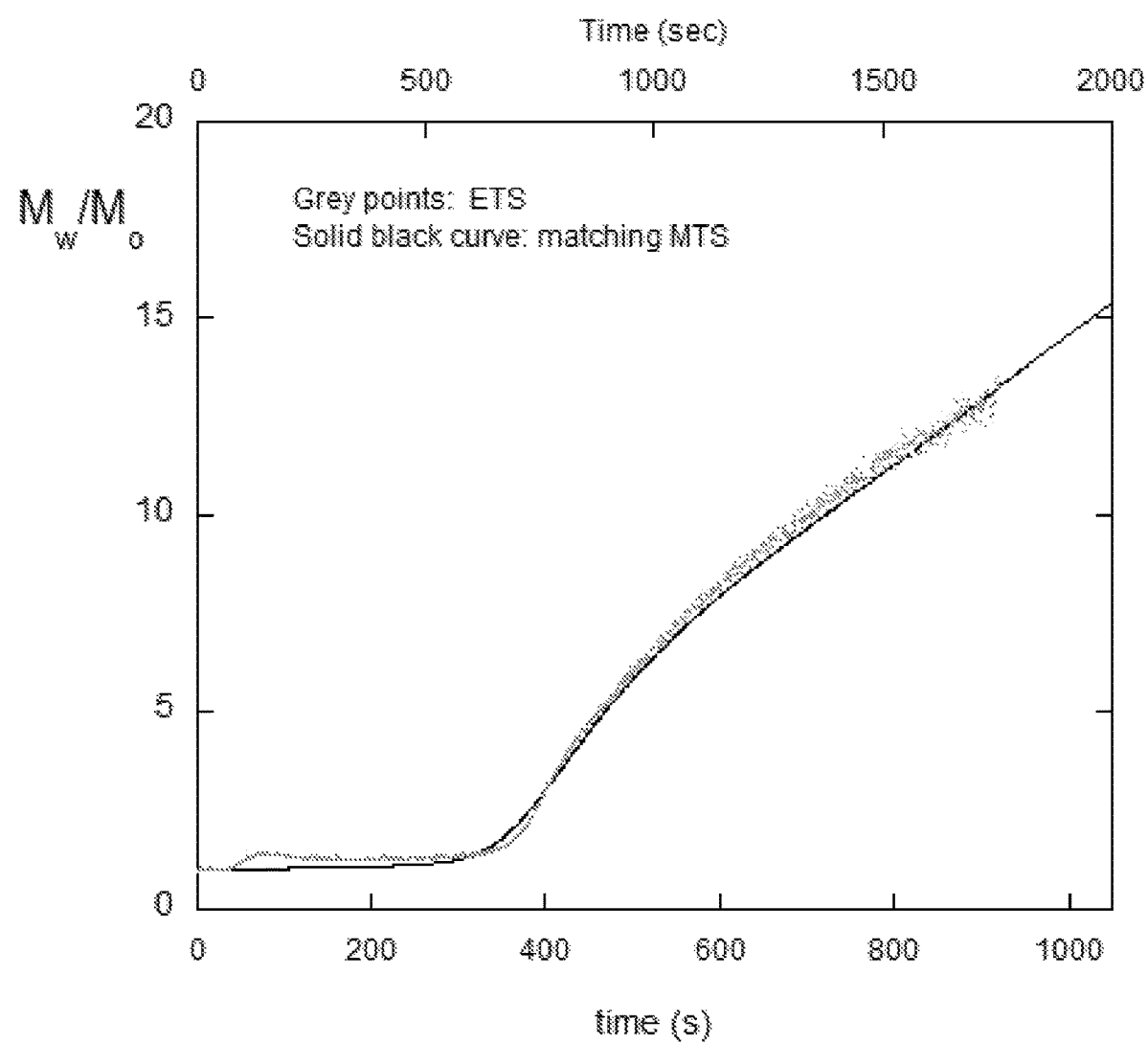
FIG. 9 is an illustration depicting real data ETS and corresponding MTS from the numerical solutions of equations 7-9 with specific sets of $k_{i,j}$, according to an example embodiment of the present disclosure.
Figure 10:
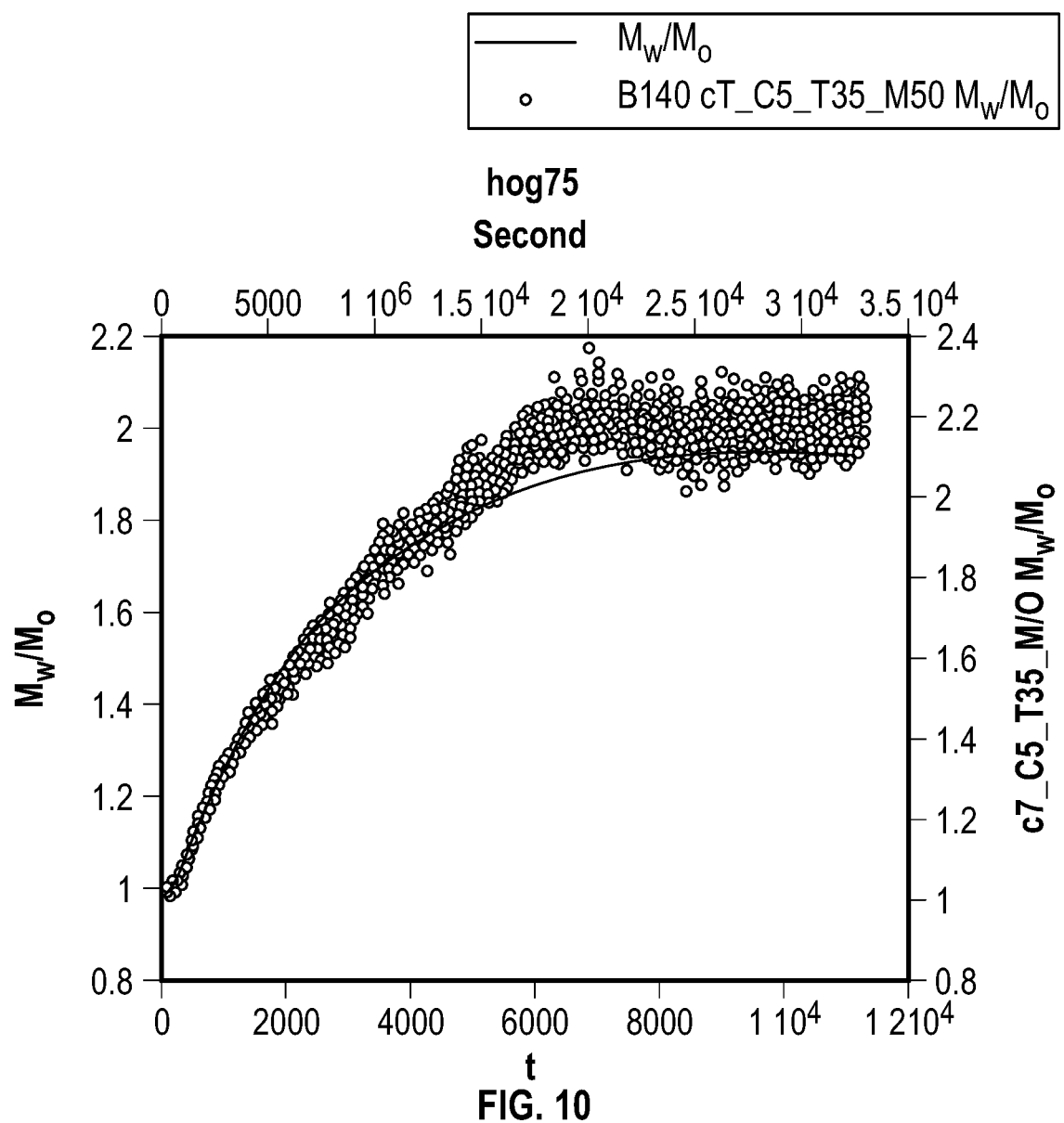
FIG. 10 is an illustration depicting real data ETS and corresponding MTS from the numerical solutions of equations 7-9 with specific sets of $k_{i,j}$, according to an example embodiment of the present disclosure.
Figure 11:
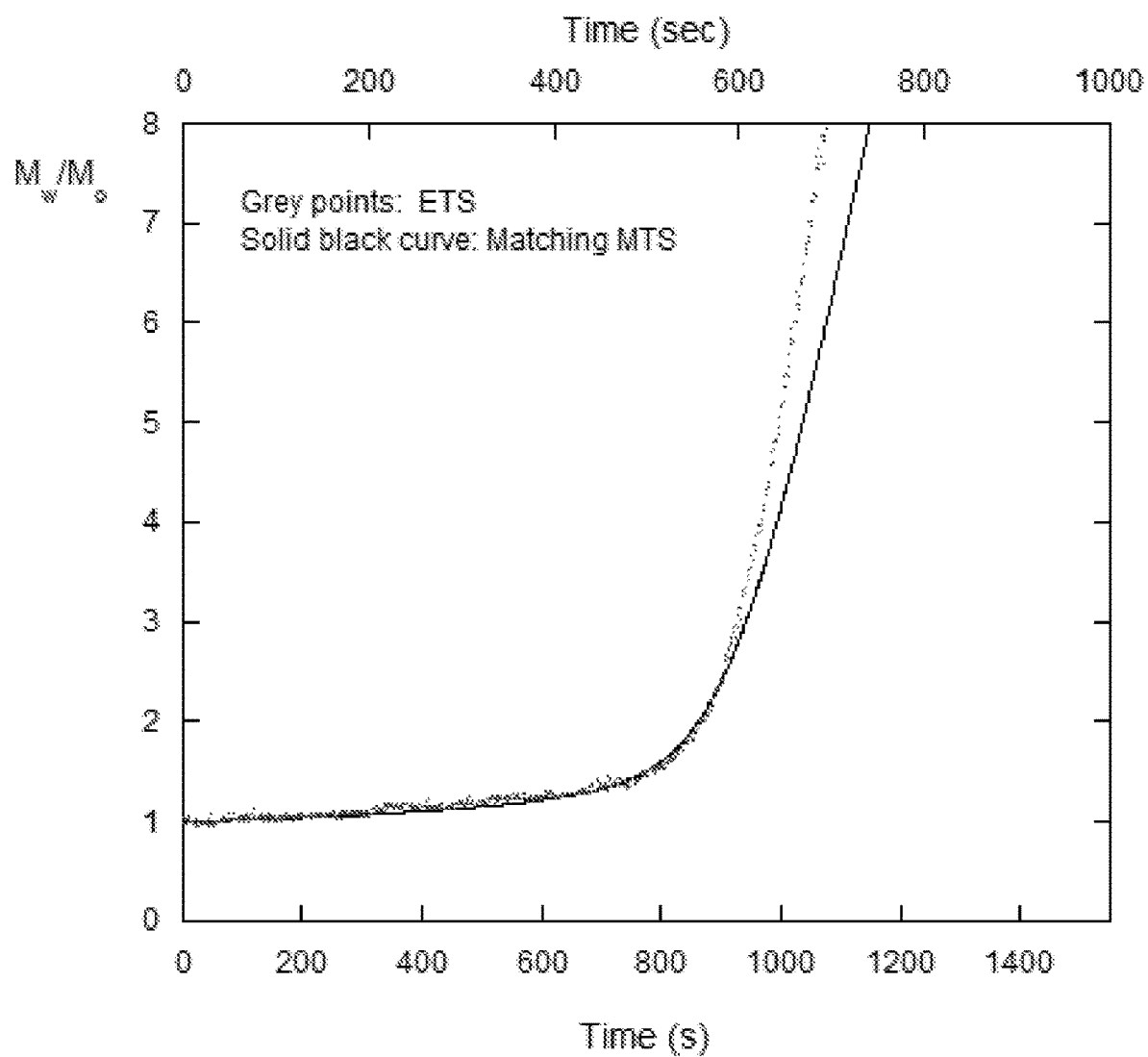
FIG. 11 is an illustration depicting real data ETS and corresponding MTS from the numerical solutions of equations 7-9 with specific sets of $k_{i,j}$, according to an example embodiment of the present disclosure.

The instructions, media for conveying such instructions, computing resources for executing them, and other structures for supporting such computing resources are means for providing the functions described in these disclosures. FIG. 7 depicts a simultaneous multiple light scattering SMSLS device and system that may be used in conjunction with the present technology. The SMSLS device provides for high throughput characterization of multiple samples using continuous total intensity light scattering. This has been achieved by fully parallel operation, whereby each sample cell has its own light source and detection, and independent access to multiple stressors and conditions, and there are no moving parts so that the precise alignment required for absolute light scattering measurements is obtained. The SMSLS hence provides the absolute scattering intensity (expressed as the Rayleigh Ration in units of 1/cm) at a fixed angle(s) versus time for each sample cell. A current, commercially available SMSLS unit, the APMT Argen, has 16 independent cells (Advanced Polymer Monitoring Technologies, Inc., New Orleans, La.).

As depicted in FIG. 7, SMSLS device 700 includes a plurality of SMSLS cells 705. Each SMSLS cell 705 is configured to receive light from a light source, such as a laser 710. The laser 710 is positioned to emit laser light into the cell 705. The laser light may pass through neutral density filters (not shown) to regulate the intensity of laser light entering the cell 705. In some embodiments, fiber optics 715 in the SMSLS cell transmits the laser light emitted into the cell to a photodetector 720. The photodetector 720 may be a charged couple device (CCD), a photomultiplier, a photodiode, or similar device. Each photodetector 720 may be coupled with a computing system 725, such as computing system 600 depicted in FIG. 6. The computing system 725 may be configured to carry out the methods and techniques of the present disclosure. According to at least one aspect of the present disclosure, device 700 is capable of acquiring continuous measurements of experimental time dependent light scattering signatures (ETS).

The computer system 725 may be further capable of outputting instructions to optimize or adjust at least one formulation condition of a biological polymer solution based on an identified final MTS or an identified biological polymer aggregation mechanism. The computer system 725 may also be capable of outputting instructions to alter the formulation conditions of the solution until a predetermined biological polymer aggregation mechanism is achieved. The output instructions may be in the form of machine readable code or other computer-readable or machine-readable instructions suitable to cause a device or robot to adjust, alter, or optimize the formulation conditions of a biological polymer solution. In other cases, the output instructions may be in the form of text or other written instructions suitable to allow a user to adjust, alter, or optimize the formulation conditions of a biological polymer solution. Accordingly, computer system 725 may be coupled with robotic device 730 that is configured to adjust, alter, or optimize the formulation conditions of a biological polymer solution based on an identified final MTS or an identified biological polymer aggregation mechanism, or so as to achieve a predetermined biological polymer aggregation mechanism in the biological polymer solution. In at least some instances, robotic device 730 may be coupled with one or more cells 705, as shown in FIG. 7, such that robotic device 730 is capable of adjusting, altering, or optimizing the formulation conditions of a biological polymer solution in one or more cells 705.

Each SMSLS cell 705 may be coupled with one or more temperature control devices capable of controlled or uncontrolled heating of the SMSLS cell 705. In some embodiments a peltier device is used in the temperature control configuration to also allow cooling of the SMSLS cell 705, or a resistance heating unit, such as a high resistance wire, etc. In some embodiments, in addition to the peltier device each SMSLS cell 705 can also be coupled to a fan to exhaust heat extracted from the SMSLS cell 705.

The SMSLS cells 705 can either be batch cells or flow cells. In a flow cell, fluid flows through the cell while laser light emitted into the cell flows through a portion of the flowing fluid stream. Peristaltic pumps can be utilized to pump different materials into a mixing manifold to mix different materials prior to flowing the materials through the flow cell. For example, peristaltic pump may pump a protein into the mixing manifold and an alternative peristaltic pump can pump buffer into the mixing manifold producing a mixed stream of protein and buffer exiting the mixing manifold and entering into the flow cell 705. One of ordinary skill in the art will appreciate that other pump types may be used in conjunction the flow cells and mixing manifolds. For example, in some embodiments a positive displacement pump may be used to pump materials into the mixing manifold. In a batch cell, the composition of material within the batch cell is prepared independently and individually introduced into each batch cell in a vessel such as an optical glass cuvette or other similar vessel. In some embodiments, the SMSLS cells may be batch cells, flow cells, or a combination of batch and flow cells.

In some embodiments, the SMSLS system can include individual cell controls configured to set up the samples within the individual cells. The individual cell controls can include software components including a user interface for receiving instructions from an operator regarding the setup and variables tested among the individual cells. In some embodiments, the individual cell controls can also include an interface to designate sampling statistics and intervals of interest. In some embodiments the individual cell controls can also control inputs into the cell for providing material to the cells.

In some embodiments, the stressor module(s) control the stressors associated with each individual cell. In some embodiments the stressors can include, but are not limited to, change in temperature, including freezing and thawing, application of shear forces, introduction of certain surfaces, such as metals, plastics, gas bubbles, glass, oils, specific ions, chelating or other chemical agents, ultrasound, light and other forms of radiation. The stressor module(s) allows for the temperature, stirring, stepper motor, and other stressors associated with each cell to be controlled individually for each cell. In some embodiments, the stressor module is a combination of software and hardware such as computer code for controlling a stepper motor, a processor for interpreting the computing code, the stepper motor hardware for creating a magnetic field about a cell, and a magnetic stirrer within the cell—collectively these all can be considered parts of a given stressor module. Other stressor modules include software, computing devices, and other instruments for introducing a stressor whether it is a form of energy, material, or any other stressor identified herein or known to those of ordinary skill in the art.

According to at least one aspect of the present disclosure, continuous light scattering measurements may be used to ascertain experimental time dependent light scattering signatures (ETS). Continuous measurements allow processes to be monitored that are otherwise inaccessible to other techniques, such as dynamic light scattering methods. Furthermore, continuous measurements allow for much finer aggregation mechanistic behavior to be observed and modeled. For example, some mechanistic processes occur too quickly to be resolved using dynamic light scattering methods. In contrast, the presently disclosed methods and techniques allow much faster processes to be monitored which, in turn, provides for a more powerful model approach to be utilized to determine many different mechanisms to be tested for a match.

Mechanistic Analysis without Determination of MTS and Set of $k_{i,j}$

Because further development and application of the present technology will lead to deeper classification and understanding of mechanistic classes there will be many cases where the full fitting procedure, with Ansatz and search, can be avoided. Namely, each mechanistic class produces ETS identifiable by features such as inflection points, asymptotes, positive and negative second derivatives, and so on, so that algorithms can be developed to recognize the mechanistic class from the ETS features, without the added steps of finding the set of $k_{i,j}$ producing the optimal fit.

FIGS. 8-11 present examples of real data ETS and corresponding MTS from the numerical solutions of equations 7-9 with specific sets of $k_{i,j}$. The MTS shown are not the optimized MTS from a consistent key variable search procedure, rather, they are from adjusting some key variables to obtain reasonable matches.

Phenomenological Compressed Exponential Fits to ETS

Figure 12:
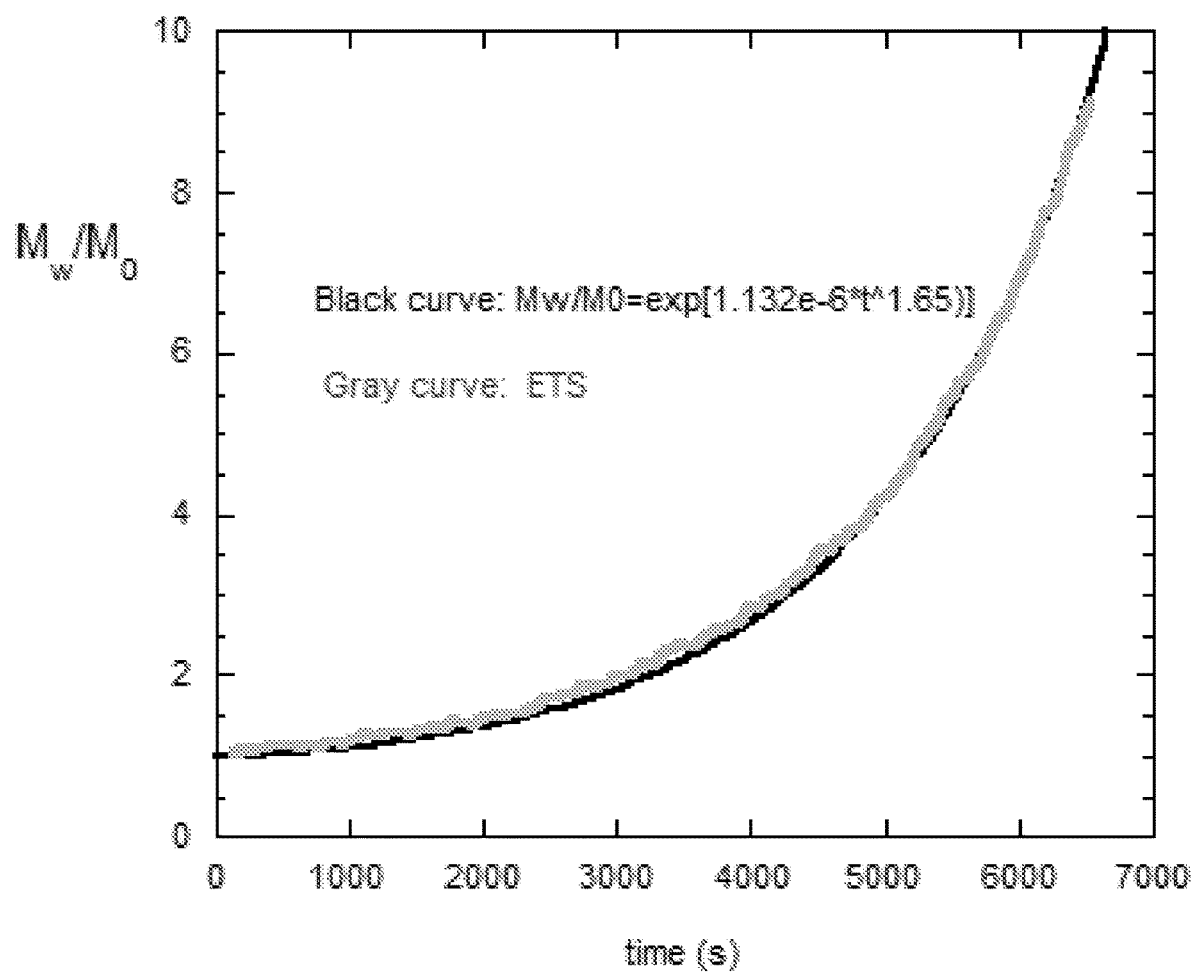
FIG. 12 is an illustration depicting a non-linear signature of an ETS fit according to a component exponential function, according to a an example embodiment of the present disclosure.

In general, the non-linear signatures of the ETS cannot be fit by ordinary functions, such as exponentials or polynomials. It is found, however, for some classes of ETS that the compressed exponential function of the form $$M_w(t)/M_0 = \exp[\gamma t^\beta] \tag{15}$$

where $\beta > 1$ provides an excellent fit. An example of such a close fit is shown in FIG. 12. For this fit $\beta = 1.65$.

Figure 13:
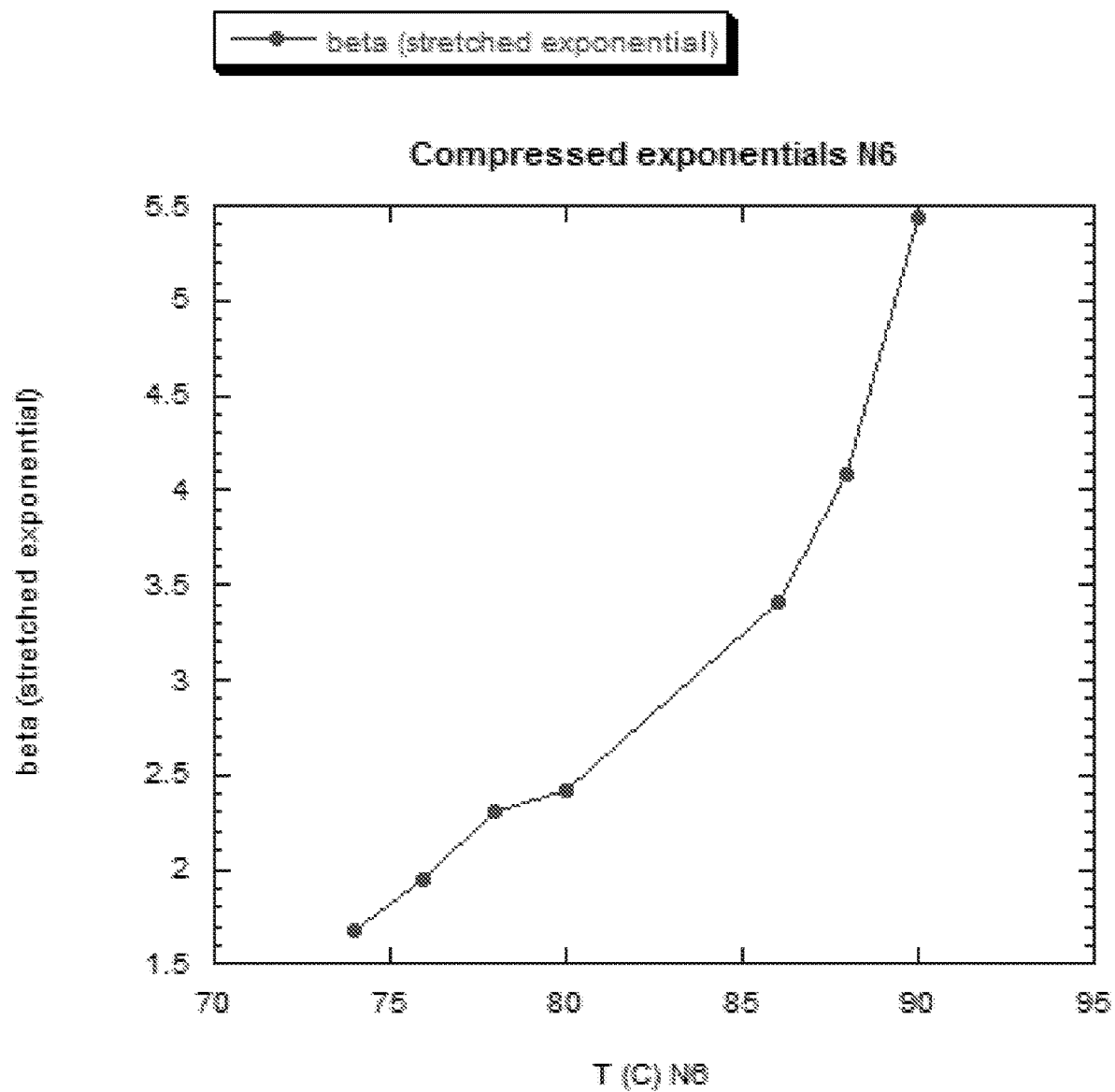
FIG. 13 is an illustration depicting how the stretching exponent $\beta$ increases with temperature for the same protein analyzed in FIG. 12 and under the same formulation conditions, according to an example embodiment of the present disclosure.

Furthermore, trends in $\beta$ can be found. FIG. 13 shows how the stretching exponent $\beta$ increases with temperature for the same protein under the same formulation conditions.

For the classes of ETS for which the compressed exponential yields a good fit the stretching factor $\beta$ can serve as a mechanism index in some applications of the present technology.

On the Superposability of Pairs of ETS

A notion that results directly from the model based approach of the present technology is that if there exists a proportionality constant between the time bases of non-linear ETS from two separate aggregation processes which yields an exact superposition of the two non-linear ETS then the underlying kinetic pathways for the two processes are of the same kind. This notion is further extended to cases where the superposition is not exact and a quantitative scale can be applied to the non-exact superposition to discern to what extent the mechanisms of aggregation in two different processes are similar.

This can be illustrated by considering that a broadly applicable means of representing continuous functions, such as the $M_w(t)$, $M_{w,agg}(t)$, $M_w(t)/M_0$ found during protein aggregation is by a function $f(t)$ with a power series expansion of time of the form $$f(t) = \sum_{i=0}^{\infty} a_i(\alpha t)^i \qquad (16)$$

where $\alpha$ defines the time scale on which the process occurs and any given set of $\alpha_i$, $\{a_i\}$ defines a specific mechanism; the $a_i$ are the 'mechanistic constants' related to all the underlying kinetic and mass balance equations and constants. In this $f(0)=a_0$. Now consider two processes #1 and #2, described by $f_1(t)$ and $f_2(t)$, respectively, so that $$f_1(t) = \sum_{i=0}^{\infty} a_{1,i}(\alpha_1 t)^i \qquad (17a)$$

$$f_2(t) = \sum_{i=0}^{\infty} a_{2,i}(\alpha_2 t)^i \qquad (17b)$$

Let $f_1(t)$ and $f_2(t)$ be scaled to each other by a constant factor such that $f_1(0)=f_2(0)$. If there exists a constant $\gamma$ such that $\alpha_2=\alpha_1\gamma$ which allows the scaled $f_1(t)$ and $f_2(t)$ to superpose exactly upon each other, then the two processes share the same set of mechanistic constants $\{a_i\}$. That is, the superposability of $f(t)$ for the two processes, via a proportionality constant in their time bases, proves that they share the same mechanism (that is, the same mechanistic constants).

It is noted that specific functional forms, such as $e^{\alpha t}$ or $\tan h(\alpha t)$ have pre-determined, exact mechanistic constants $\alpha_i$; e.g. for $e^{\alpha t}$.

$$a_i = \frac{1}{i!}.$$

This means that if a specific functional form is assignable to scaled $f_1(t)$ and $f_2(t)$—that is, varying only in $\alpha_1$ and $\alpha_2$—they are controlled by the same mechanism. An exception to this is when $f(t)$ is linear, since any two lines can always be made to superpose by scaling the y-intercept and adjusting the slope. Since many functional forms are well represented by a linear expression when $\alpha t \ll 1$—for example, $e^{\alpha t} \approx 1+\alpha t$ when $\alpha t \ll 1$—it is necessary that $f(t)$ be non-linear to apply the superposability criterion.

In practical applications, there is always experimental noise in $f(t)$ so that superposition of $f_1(t)$ and $f_2(t)$ will never be exact. Hence, it is necessary to have criteria for judging the degree of superposability of $f_1(t)$ and $f_2(t)$. The most straightforward measure of the goodness of superposability is the minimization of the reduced mean square difference between the functions, $\chi^2$. Data collected by light scattering are collected at discrete time intervals or frequencies such as, for example, 10 Hz. Then, time points can be tracked by an integer index $j$, so that $t_j$ is the value of time at the $j^{th}$ measurement. Then $$\chi^2 = \frac{1}{N} \sum_{j=1}^{N} [f_1(t_j) - f_2(t_j)]^2 \qquad (18)$$

After scaling $f_1(0)$ and $f_2(0)$ to each other, the value of $\gamma$ can be found that minimizes $\chi^2$. The value of $\gamma$ yielding the minimum $\chi^2$ can be termed the 'optimal time scaler'. Contributions to $\chi^2$ can occur both from random noise in the data and from actual differences in the mechanistic constants $\{a_{1,i}\}$, $\{a_{2,i}\}$ between $f_1(t)$ and $f_2(t)$. Of course, the most important source of difference is the latter, since one is seeking possible differences in mechanism. A good means of determining this is via the residual $f_1(t)-f_2(t)$. This function can be formed and plotted or otherwise analytically or numerically analyzed after the optimum value of $\gamma$ has been found. If the residual is random versus time, then the origin of $\chi^2$ is exclusively due to experimental noise. If there is also a non-random trend in the residual, then there are differences in mechanism due to differences between $\{a_{1,i}\}$, $\{a_{2,i}\}$.

$f_1(t)$ and $f_2(t)$, as mentioned, are related to a scattering quantity such as $M_w(t)$, $M_{w,agg}(t)$, $M_w(t)/M_0$, and others. It will frequently be the case that these quantities must be manipulated first in order to turn them into functions, such as $f_1(t)$ and $f_2(t)$. For example, in comparing ETS of different concentration solutions it might be necessary to subtract a different initial or final background and scale the magnitude of the quantity in order to cast it into the form of $f(t)$.

ETS can be expressed in several ways such as by $M_w(t)/M_0$, where $M_w(t)$ is the weight average of all scatterers in the scattering solution at any instant $t$, and $M_0$ is the value before stressors are applied, or by $M_{w,agg}(t)$, the weight average of the aggregate population, excluding unaggregated native proteins. In the case of unaggregated starting material, $M_0$ is the molar mass of the native protein.

Figure 14:
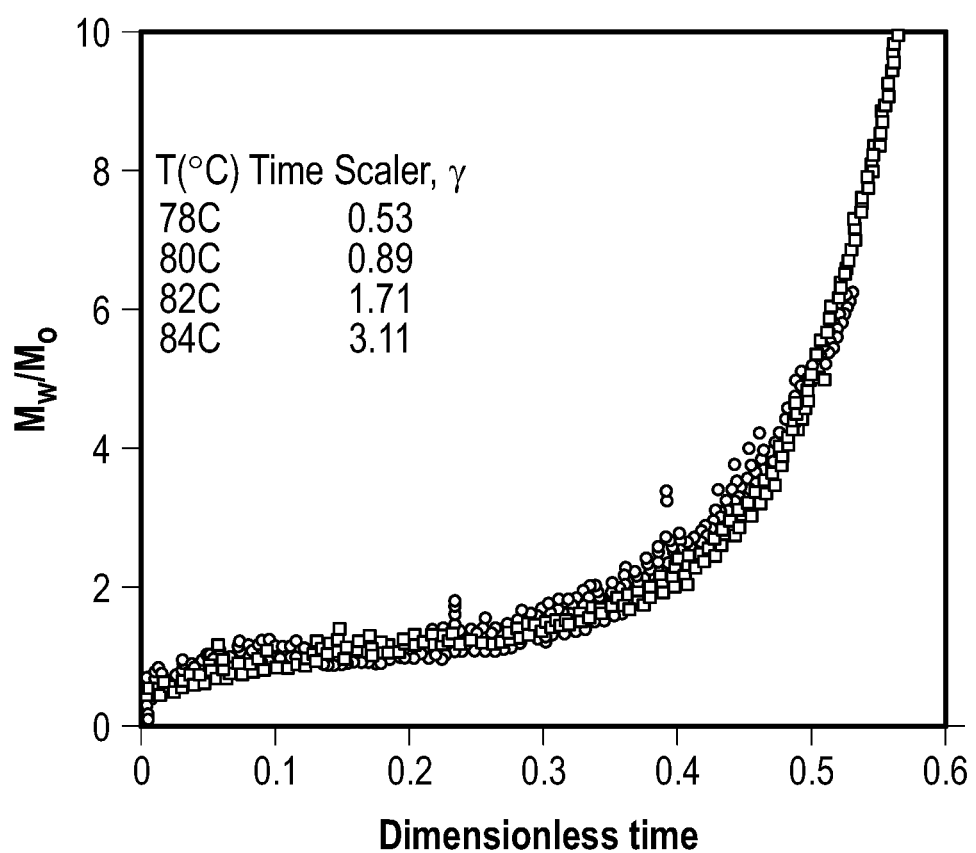
FIG. 14 is an illustration depicting four superposed $M_w(t)/M_0$ for a protein at four different temperatures, according to an example embodiment of the present disclosure.

An example of four superposed $M_w(t)/M_0$ for a protein at four different temperatures is shown in FIG. 14. The concentration of protein was 0.001 g/cm$^3$, the same concentration in all subsequent figures, unless otherwise noted. The inset to FIG. 14 shows the optimal time scaler $\gamma$, described above, by which the real time scale was multiplied in order to superpose all the curves on a single dimensionless time scale. As shown, the superpositions are fairly good. In fact they are good enough that the individual data sets overlap so much that they cannot be distinguished in FIG. 14. Hence, FIG. 15 contrasts the same data as in FIG. 14, except with the x-axis in real time, and the separate data sets are readily distinguishable from each other, since the aggregation processes occur on very different time scales.

In approaching the issue of quantifying the superposability between reduced time scale functions $f_1(t)$ and $\eta_2(t)$, the residual $R(t)$ between two functions $f_1(t)$ and $f_2(t)$ can be defined as $$R(t) = \frac{f_1(t) - f_2(t)}{f_1(t) + f_2(t)} \qquad (19a)$$

If $R(t)=0$ at all points then $f_1(t)$ and $f_2(t)$ are perfectly superposable and the underlying mechanisms are identical. When $f_1(t) \gg f_2(t)$, $R(t)$ approaches 1, and when $f_1(t) \ll f_2(t)$, $R(t)$ approaches $-1$. The values of $R=\pm 1$ are hence the limits of complete non-superposability for $f_1(t)$ and $f_2(t)$. Values of R between 0 and 1 hence represent intermediate superposability and it will become clearer with practice how to interpret R or other quantities that assess superposability, such as $\chi^2$ and other quantities.

Figure 16:
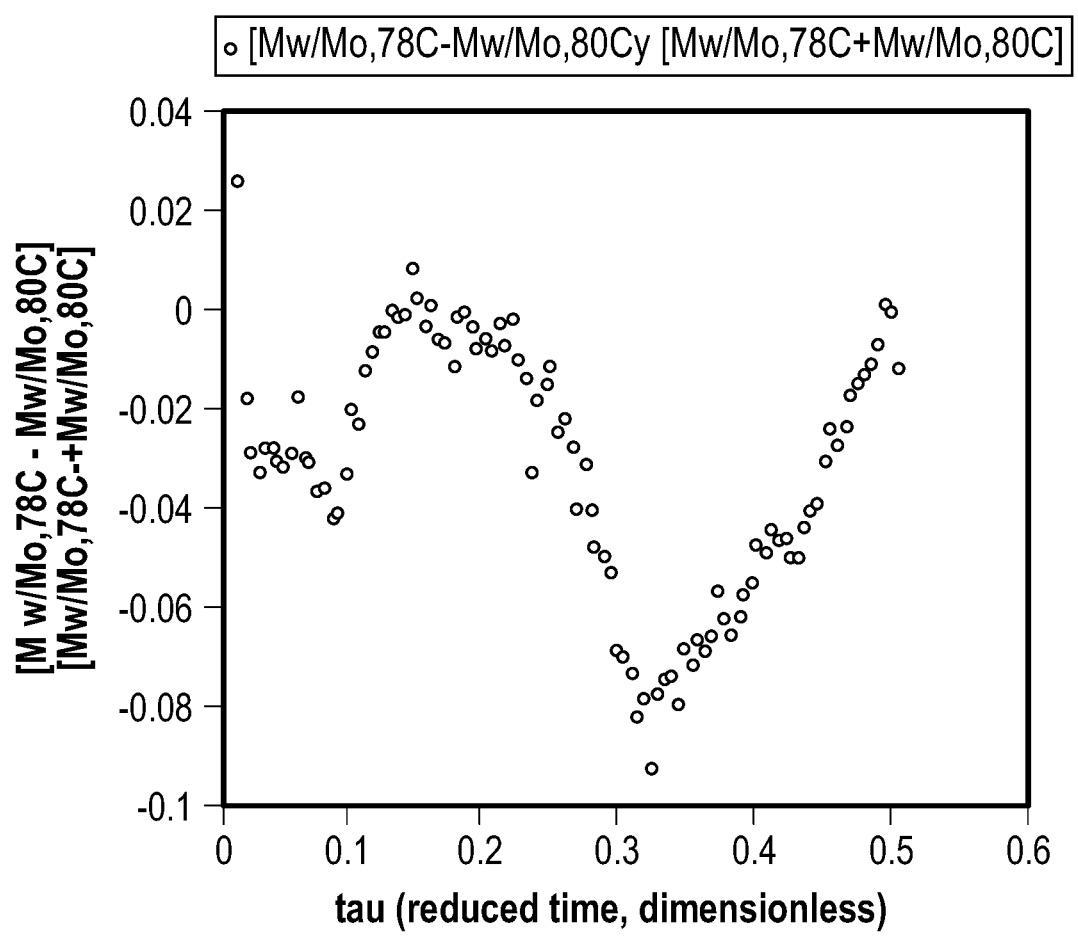
FIG. 16 is an illustration depicting residuals between 86° C. and 82° C., according to an example embodiment of the present disclosure.

The residuals between 86° C. and 82° C. are shown in FIG. 16. R(t) plotted in FIG. 16 according to equation 4a is $$R(t) = \frac{M_w(78° C., t)/M_0 - M_w(80° C., t)/M_o}{M_w(78° C., t)/M_0 + M_w(80° C., t)/M_o} \quad (19b)$$

Where $<M_w(t)/M_0>$ is the average between the $M_w(t)/M_0$ for the two temperatures. R represents the fractional difference between the two results at each instant of dimensionless time, which generally does not exceed 0.08. If the two signatures were completely superposable then R would be a random scatter of points about the origin. However, in FIG. 16, R is not completely random but has some structure, which indicates that superposability is not 100% and that there is some, albeit probably slight, difference in mechanistic constants between the two temperatures.

It is hence possible to establish a series of criteria for judging the degree of supeposability of any two conditions, or for any number of conditions. When it is desired to compare a series of conditions, such as the four different temperatures shown in FIG. 14, then data can be compared pairwise, as to residuals and other possible measures of superposability. This leads to N pairwise comparisons where $$N = \frac{N!}{(N-2)!2!} \quad (20)$$

With this type of approach it is also possible to invoke specific aggregation models and test how variations of the kinetic and mass balance constants affect the residuals, thus providing a means of tracing the origins of underlying shifts in mechanisms as conditions, and hence constants, change.

Figure 17:
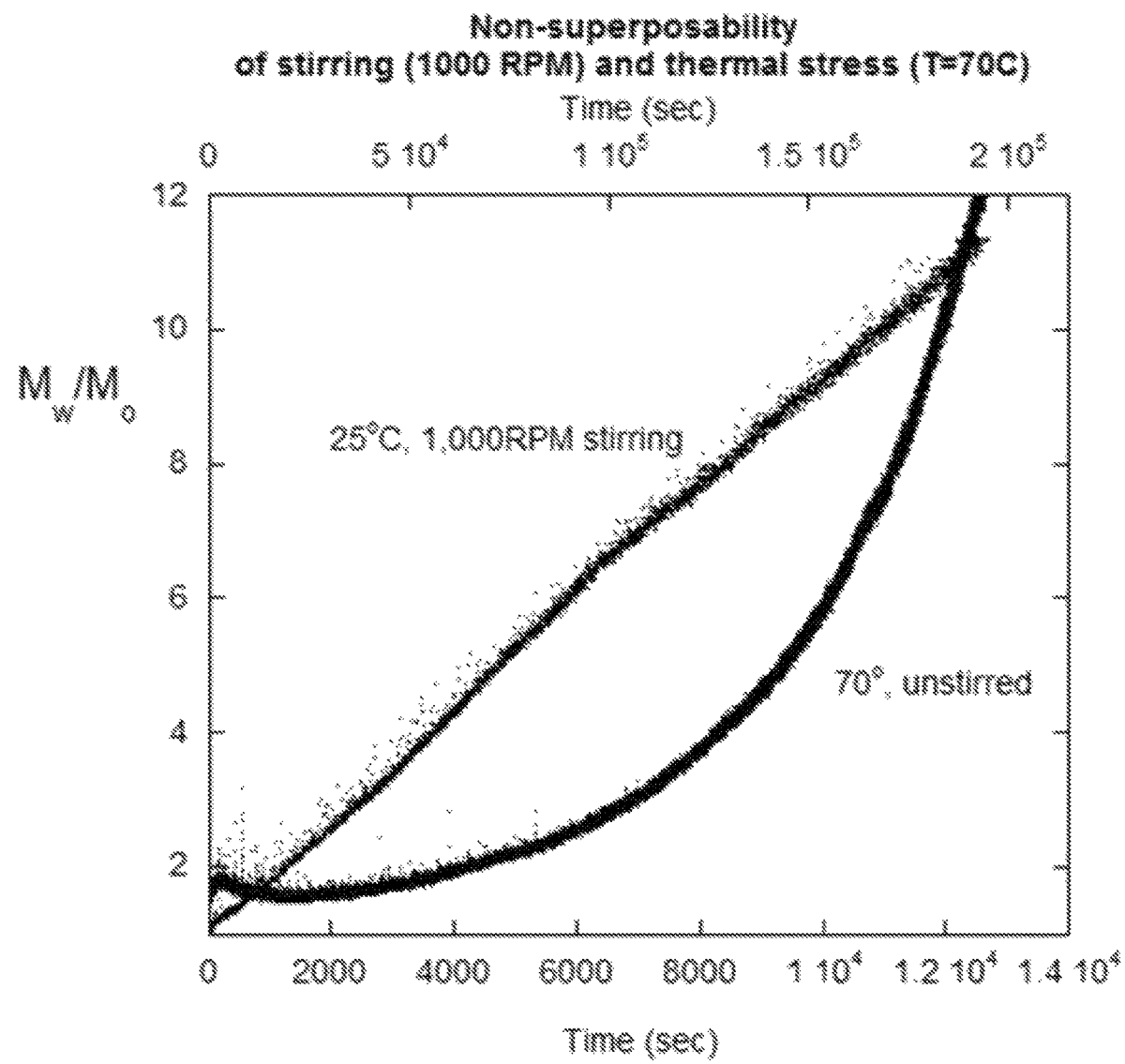
FIG. 17 is an illustration depicting a case of non-superposability, according to an example embodiment of the present disclosure.

A case of stark non-superposability can be seen in FIG. 17. In this case one aggregation process was induced by holding the protein solution at T=70° C. with no stirring. In the second process, the solution was stirred with a magnetically coupled teflon stir bar at 1,000 RPM while held at room temperature, which does not cause aggregation on any proximate time scale. In this case, instead of scaling to a dimensionless time, as in FIG. 14, two time scales are used to represent the superposability. The top time scale refers to the 70° C. sample and the lower time scale to the stirred sample.

Figure 18:
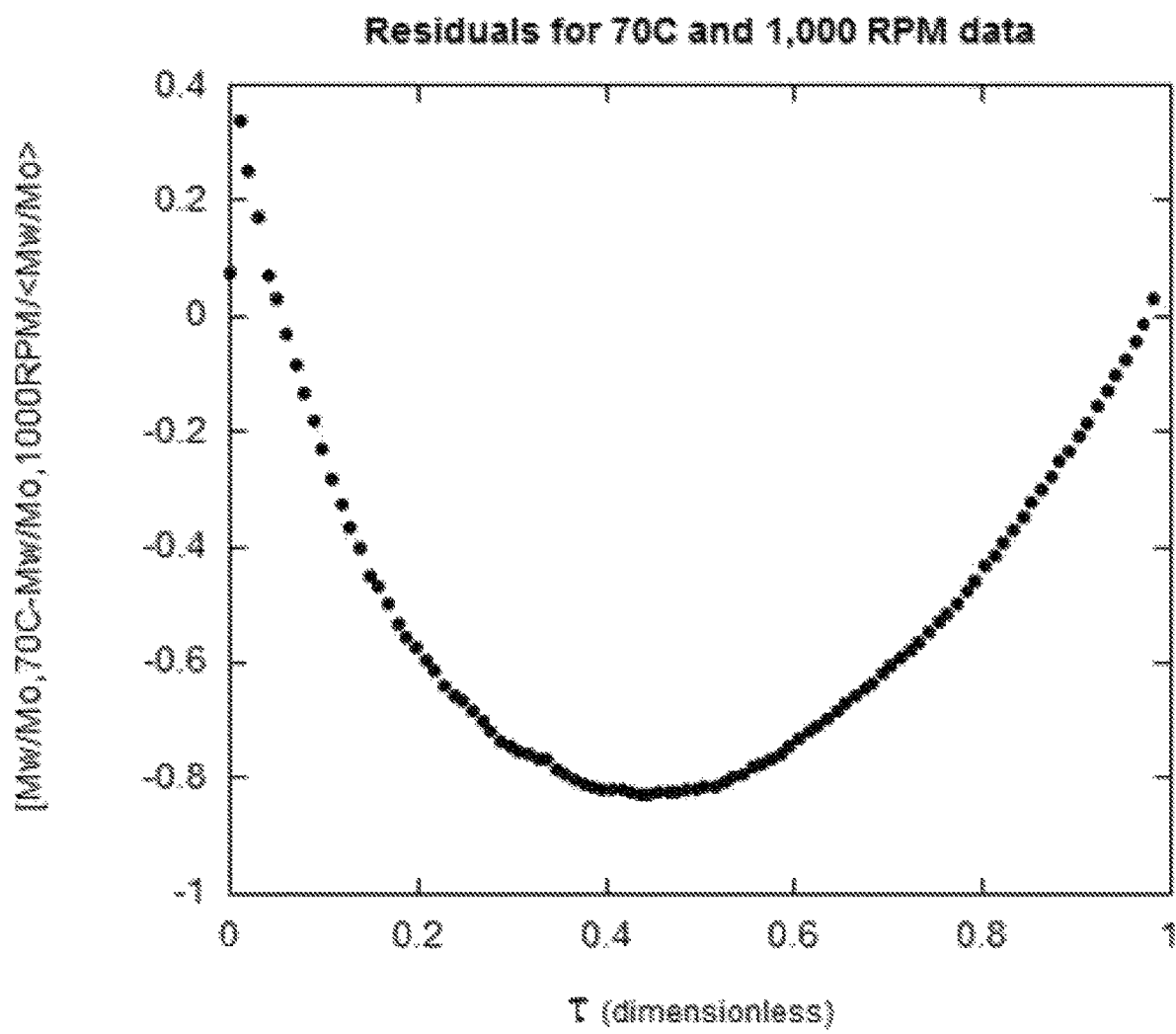
FIG. 18 is an illustration depicting the residuals for the stirring and heating data of FIG. 17, according to an example embodiment of the present disclosure.

FIG. 18 shows the residuals for the stirring and heating data of FIG. 17. While the non-superposability of the two processes can be readily observed in FIG. 17, the residuals for FIG. 18 indicate swings from R=0.4 to R=−0.8, which come close to the limit of ±1 for complete non-superposability. The disparity in the ETS between stirring and heating reveal that the aggregation mechanisms are quite different in the two cases.

OTHER EXAMPLES

Figure 19:
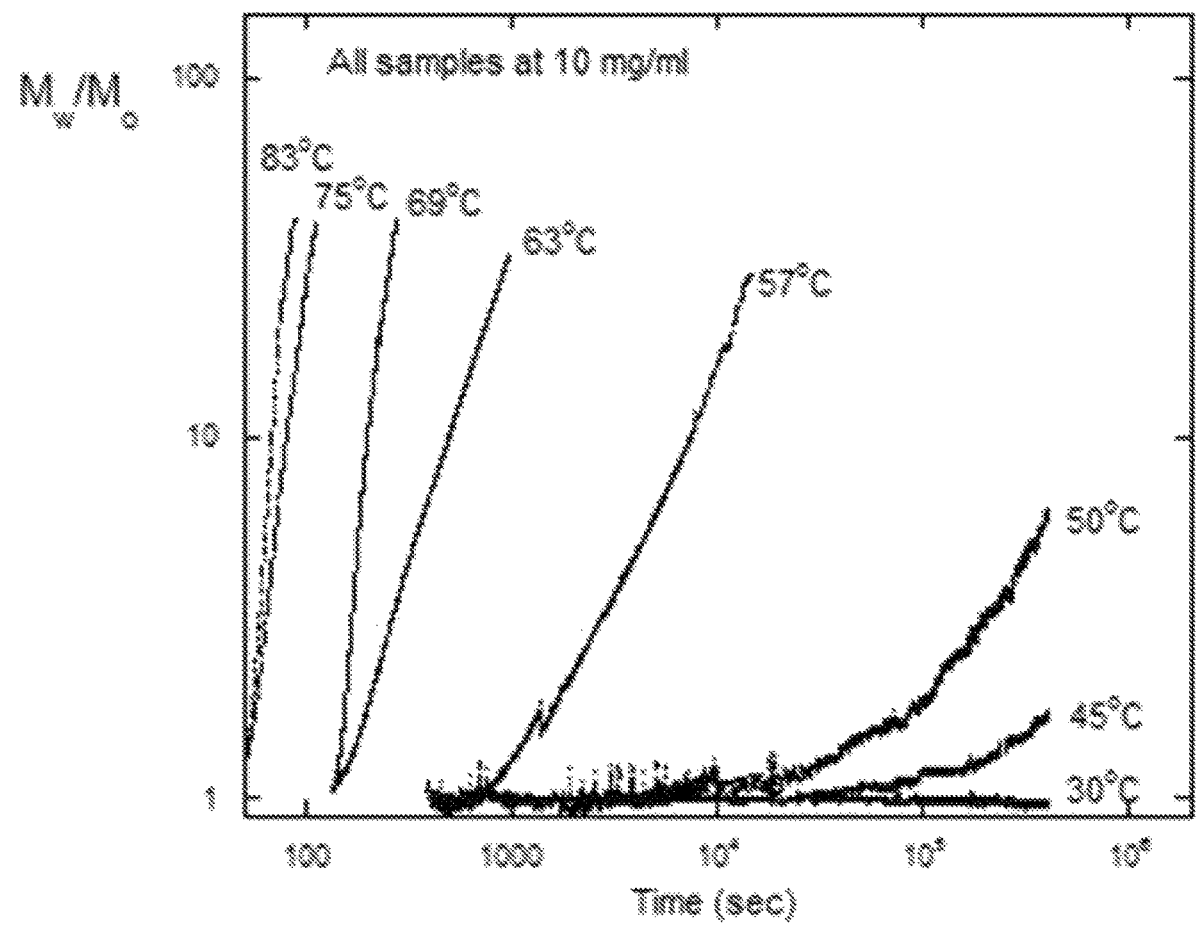
FIG. 19 is an illustration depicting $\log(M_w/M_0)$ versus $\log(time)$ for mAbB, a generic monoclonal antibody, at different temperatures, according to an example embodiment of the present disclosure.
Figure 20:
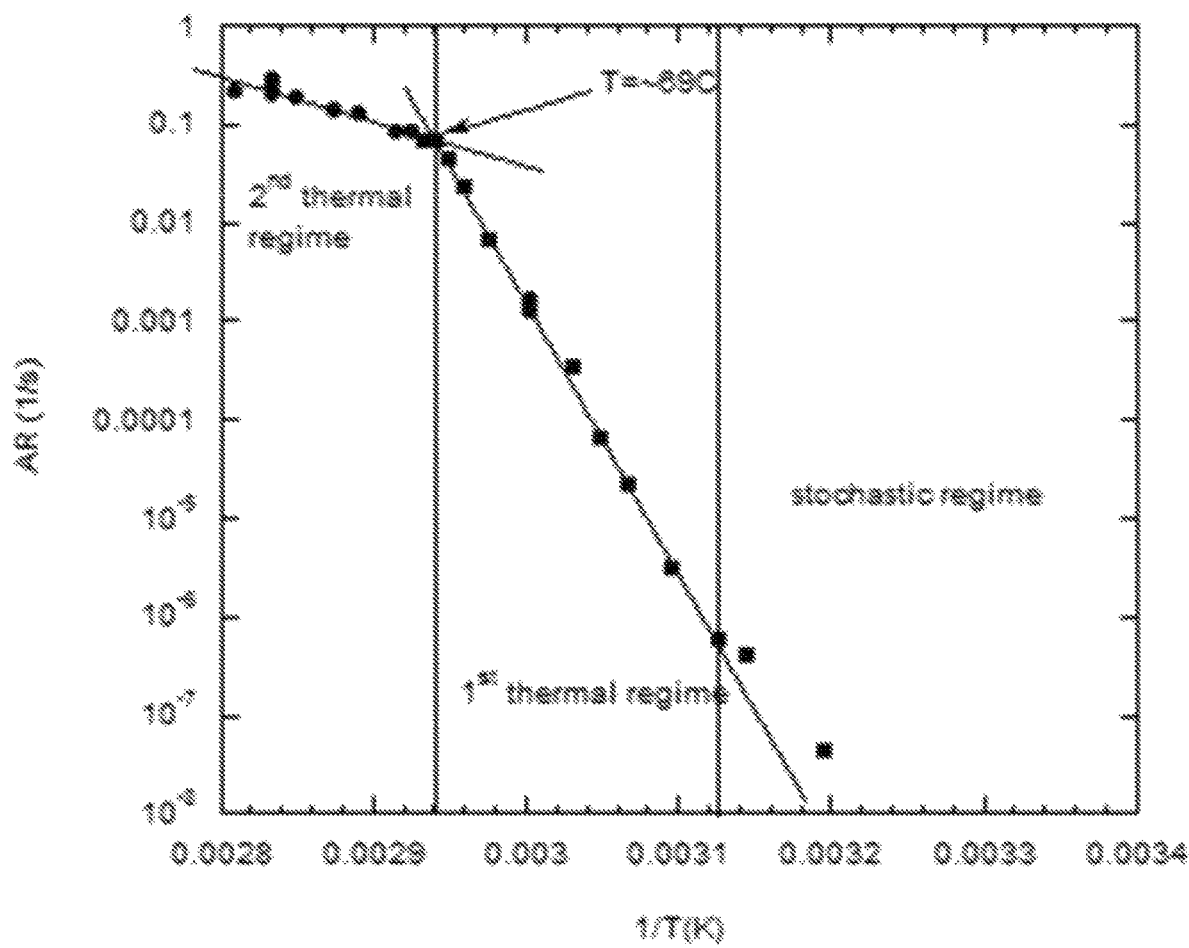
FIG. 20 is an illustration depicting the Arrhenius behavior for the same data presented in FIG. 19, according to an example embodiment of the present disclosure.

Consider the temperature dependence of a generic monoclonal antibody, mAbB, ETSs, as shown in FIG. 19, and Arrhenius behavior, as shown in FIG. 20. FIG. 19 shows $\log(M_w/M_0)$ versus log(time) for mAbB at different temperatures and FIG. 20 is the Arrhenius plot that results for the aggregation rate. The existence of the $1^{st}$ and $2^{nd}$ thermal regimes, as well as the break point between them, and the stochastic regime at the lowest temperature have been previously discussed. See M. F. Drenski et al., "Monitoring Protein Aggregation Kinetics with Simultaneous Multiple Sample Light Scattering (SMSLS)" Analytical Biochemistry, 437 (2013) 185-197, DOI: 10.1016/j.ab.2013.02.014.

Figure 15:
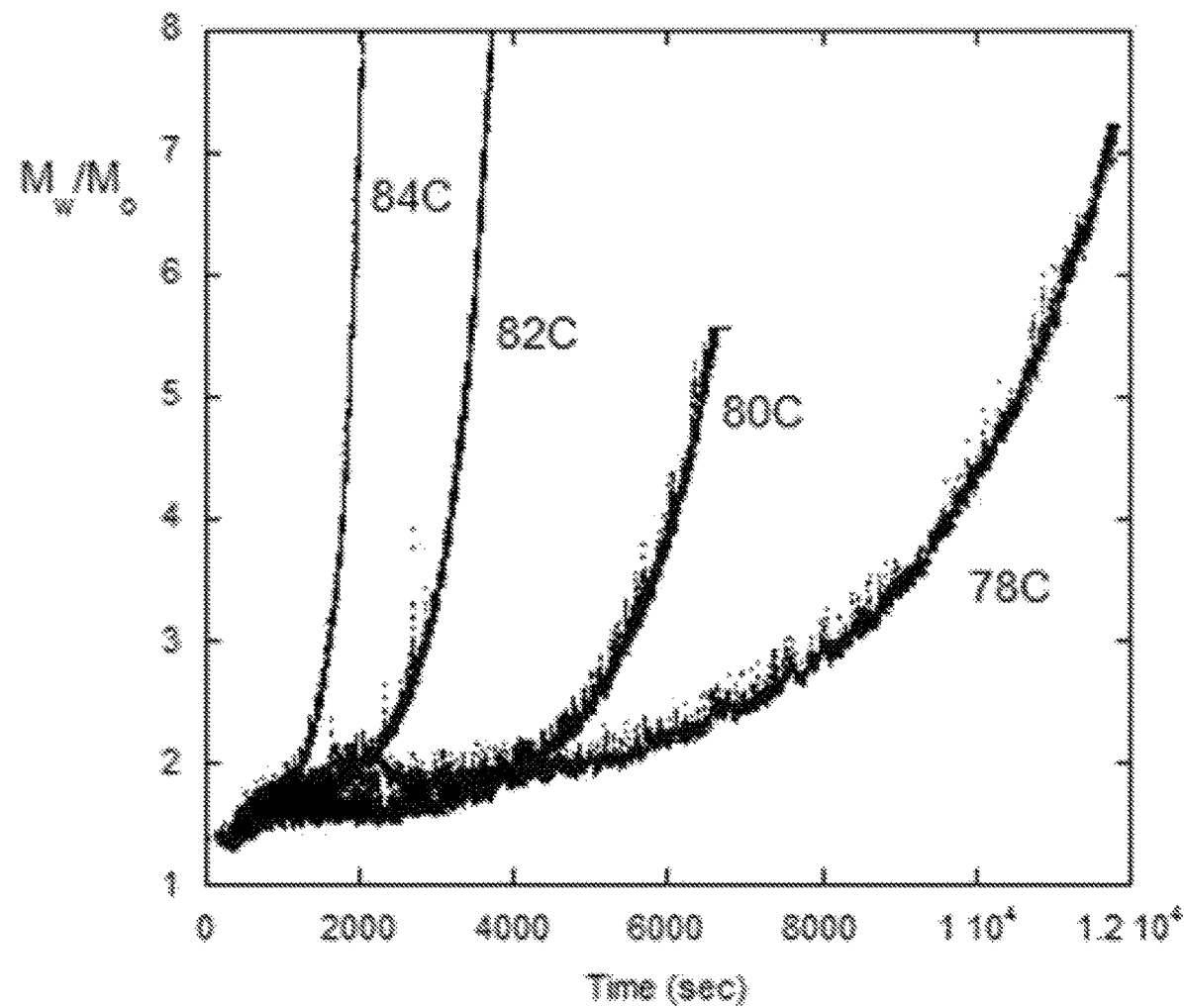
FIG. 15 is an illustration depicting the same data presented in FIG. 14, except that the x-axis in real time, according to an example embodiment of the present disclosure.
Figure 21:
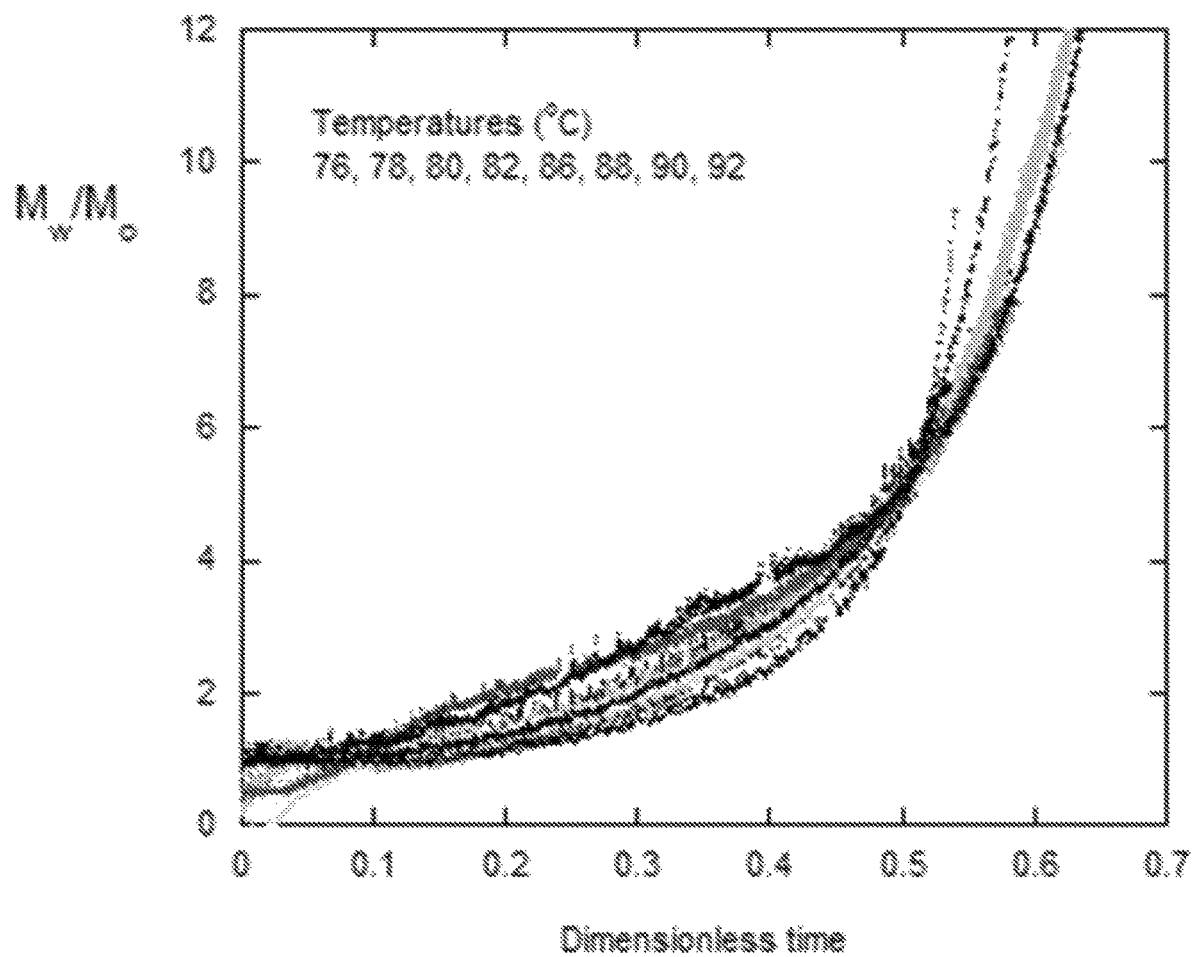
FIG. 21 is an illustration depicting the same system depicted in FIGS. 14 and 15 but under different formulation conditions of ionic strength and pH, according to an example embodiment of the present disclosure.

FIG. 21 is an example of the same protein as FIGS. 14 and 15, but under different formulation conditions of ionic strength and pH. The ETS for aggregation processes at eight different temperatures are shown. It is seen that they are somewhat close to each other but there is meaningful variation among them, and superposability does not approach perfect (R=0).

Figure 22:
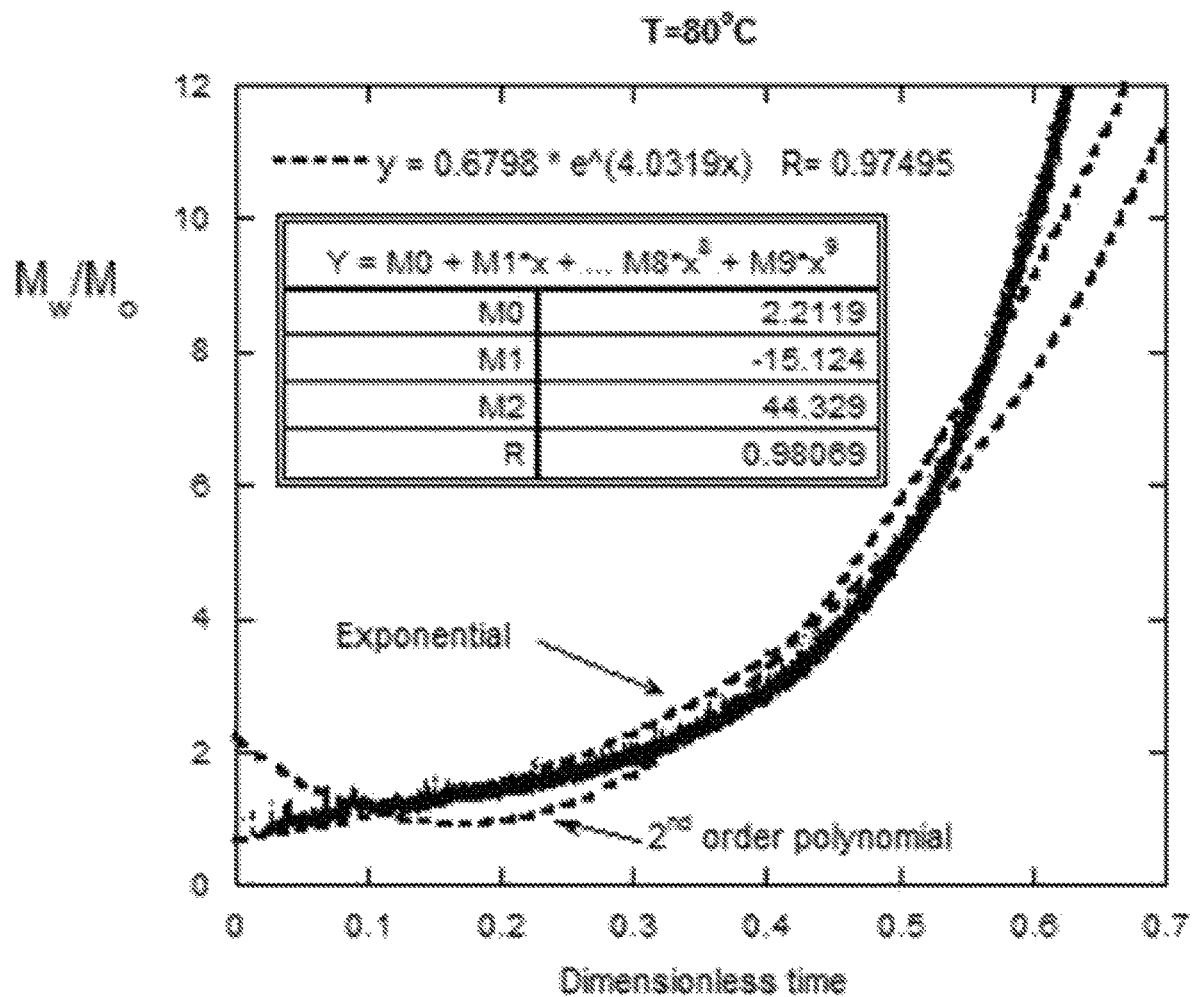
FIG. 22 is an illustration depicting an aggregation process at T=80° C., according to an example embodiment of the present disclosure.

FIG. 22 examines the case of the T=80° C. data. It shows that neither exponential nor second order quadratic fits capture the ETS. This is evidence of the underlying complexity of the various differential rate and mass balance equations and associated rate constants; that is, the ETS does not resemble these readily available analytical forms. If the ETS did fit to a form, such as an exponential, it would then be possible to superpose any other exponential process onto it.

Figure 23:
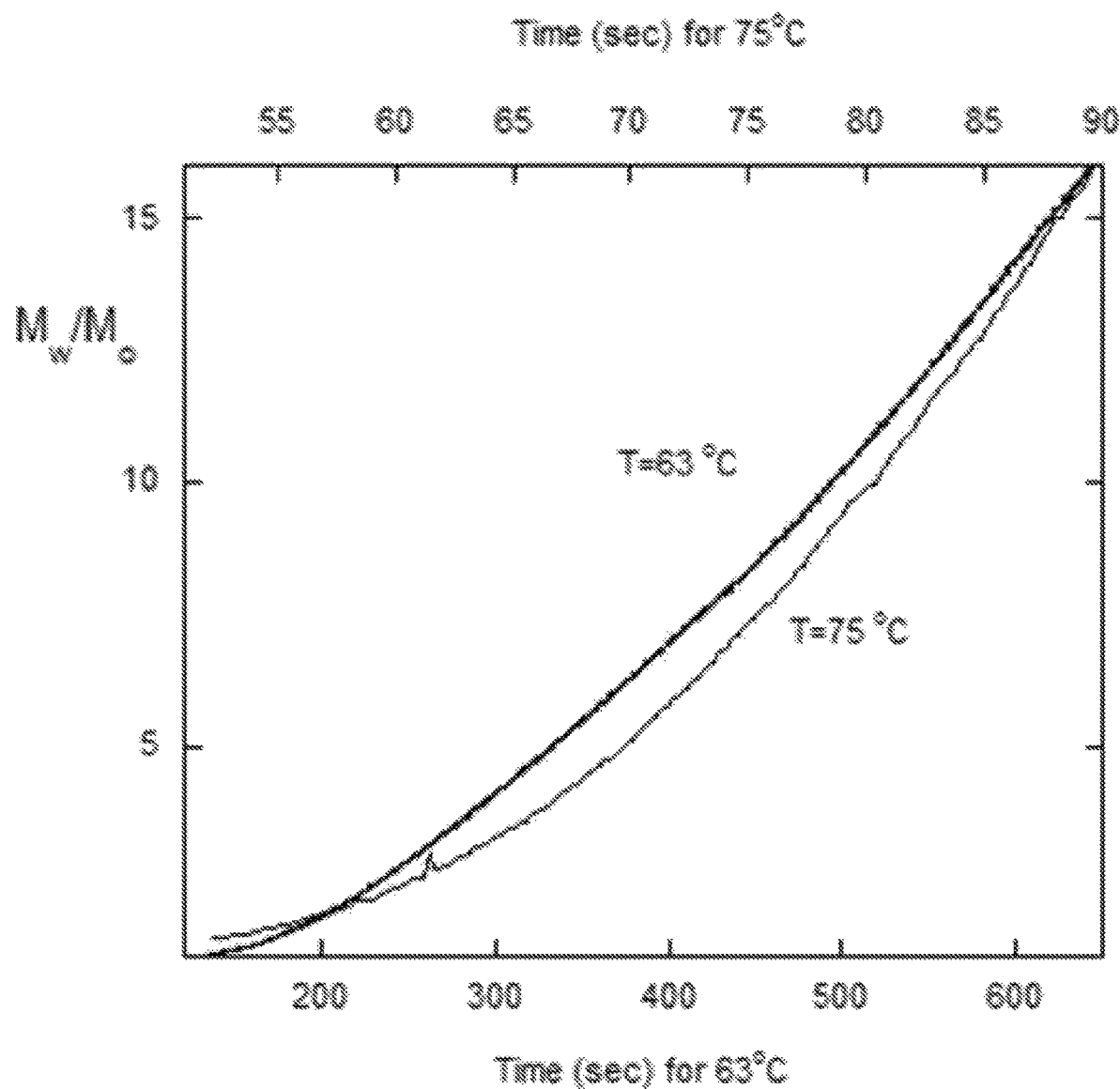
FIG. 23 is an illustration depicting transition temperature of approximately T~69° C. between thermal regimes for a protein aggregation process, according to an example embodiment of the present disclosure.

The transition temperature between thermal regimes for the protein whose aggregation process is shown in FIG. 23 is approximately T~69° C. The non-superposability between ETSs at T=63° C. and 75° C., deep in the $2^{nd}$ thermal regime seen in FIG. 23 supports the notion that the changeover between thermal regimes corresponds to different kinetic pathways.

Figure 24:
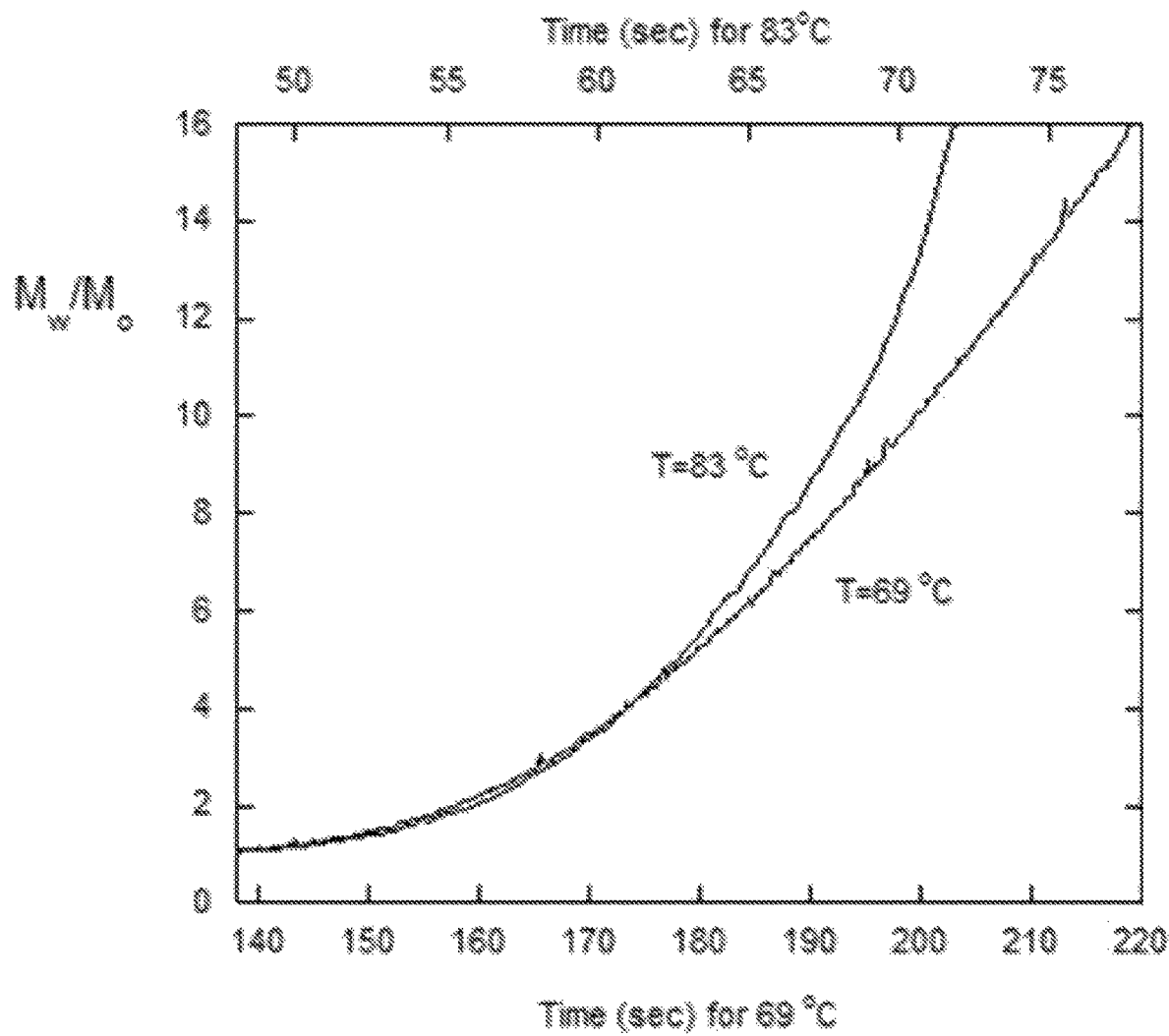
FIG. 24 is an illustration depicting a crossover between the two thermal regimes when the early portion of aggregation for T=69° C. and T=83° C. are superposed, according to an example embodiment of the present disclosure.

FIG. 24 indicates a crossover between the two thermal regimes when the early portion of aggregation for T=69° C. and T=83° C. are superposed. There is good superposability in the early non-linear zone, which is lost at higher times. A high level of superposability within the $2^{nd}$ thermal regime is seen between T=75° C. and 83° C. in FIG. 25. This can be considered a case of piecewise superposability, where there is superposability over a certain period of the process (roughly the first half period of time in FIG. 24), after which the ETS diverge (second half period of time in FIG. 24).

Figure 25:
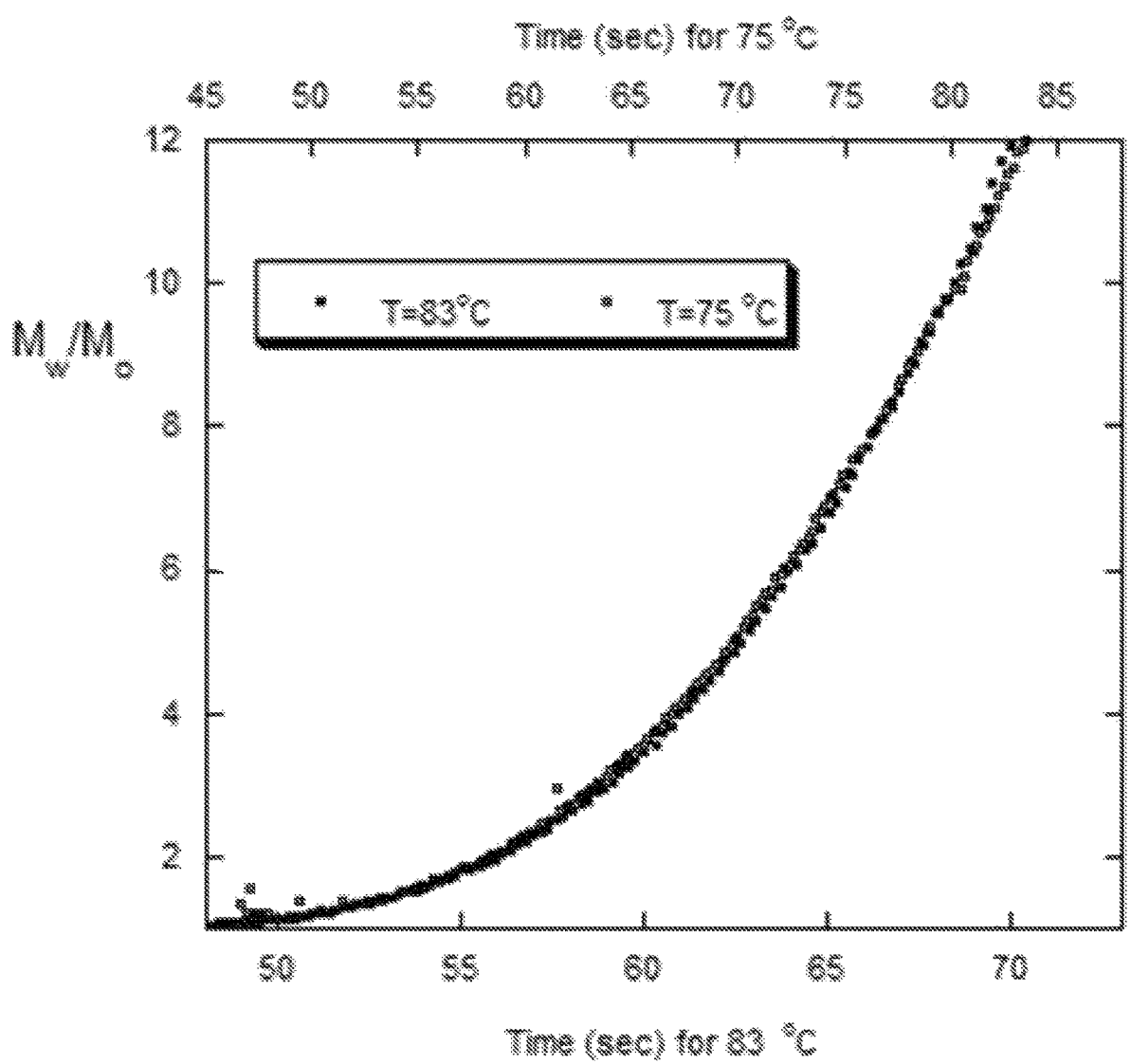
FIG. 25 is an illustration depicting a very high level of superposability for two processes within the $2^{nd}$ thermal zone of a protein, according to an example embodiment of the present disclosure.

FIG. 25 shows a very high level of superposability for two processes within the $2^{nd}$ thermal zone of this protein; T=75° C. (open squares) and T=83° C. (solid squares). The superposition is so close that the data from the two processes are indistinguishable, meaning that they share the same mechanism.

Figure 26:
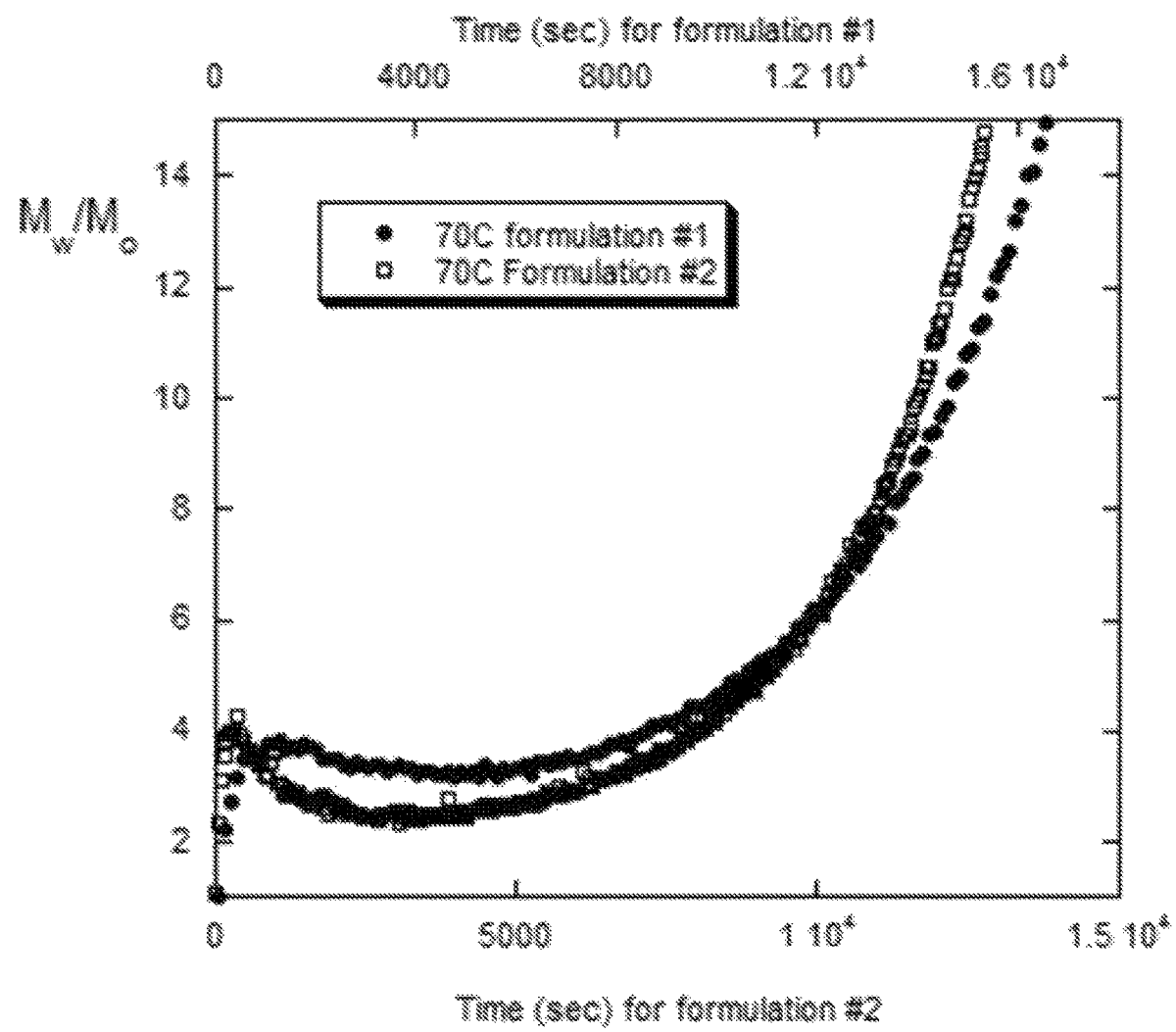
FIG. 26 is an illustration depicting an intermediate level of non-superposability in kindred processes for the same protein under two different formulation conditions, according to an example embodiment of the present disclosure.

An example of an intermediate level of non-superposability in kindred processes is shown in FIG. 26 for the same protein under two different formulation conditions. The temperature (T=70° C.), pH and ionic strength were the same, but the small molecule stabilizer for formulation #1 and formulation #2 was different. This shows one of the potential strengths of the technology for optimizing formulation conditions, discussed further below.

Figure 27:
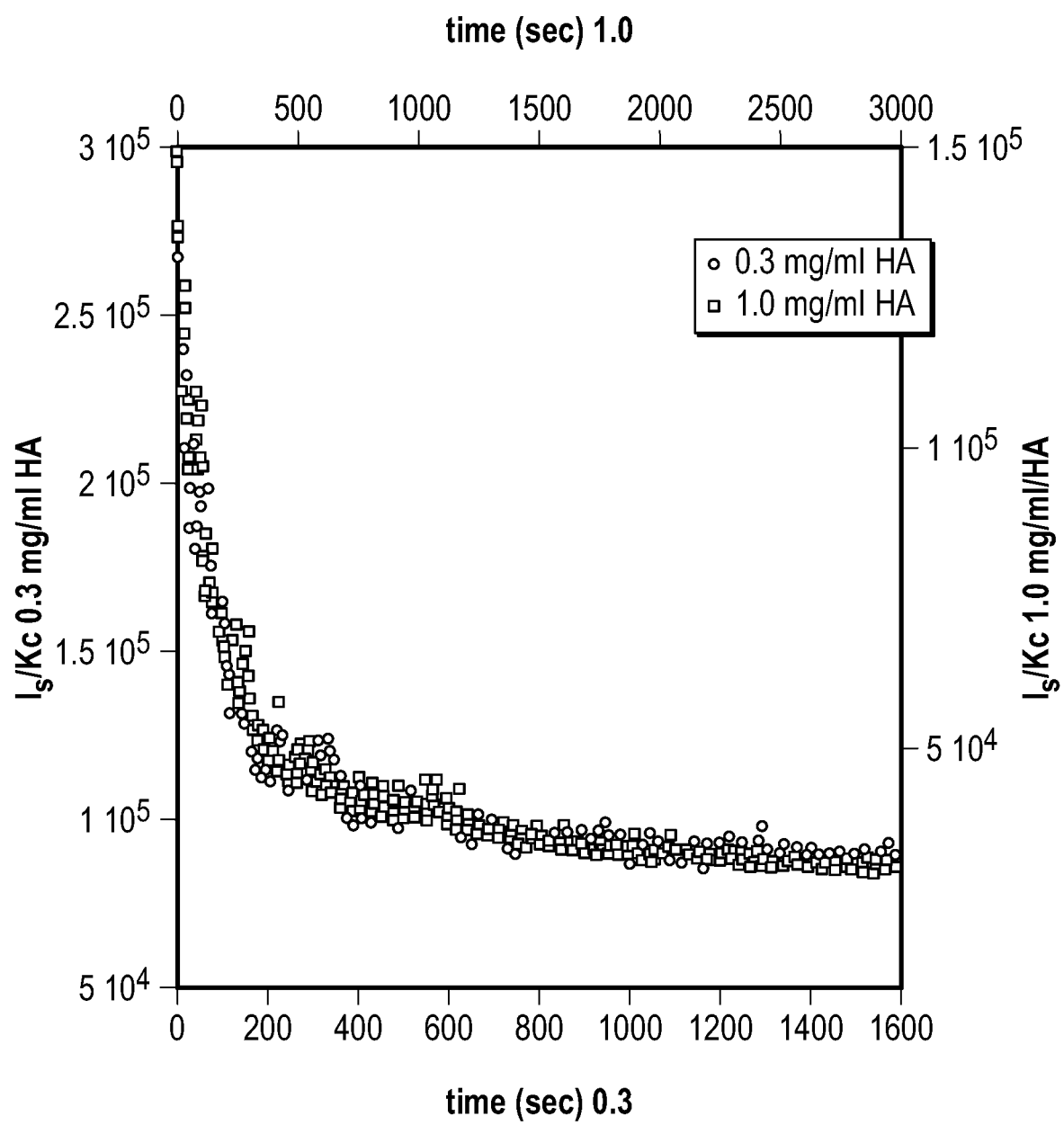
FIG. 27 is an illustration depicting data extracted for two simultaneous degradation reactions of sodium hyaluronate (HA) from *Streptococcus Zooepidemicus*, under the action of hyaluronidase from bovine testes in a buffer consisting of 0.15M NaCl and 0.1M sodium succinate at pH=5.31, according to an example embodiment of the present disclosure.

FIG. 27 shows data extracted for two simultaneous degradation reactions of sodium hyaluronate (HA) from *Streptococcus Zooepidemicus* (#H-9390, Sigma Aldrich, St. Louis), under the action of hyaluronidase from bovine testes (#H-3884, Sigma Aldrich), in a buffer consisting of 0.15M NaCl and 0.1M sodium succinate, at pH=5.31. See M. F. Drenski, W. F. Reed, "Simultaneous Multiple Sample Light Scattering for Characterization of Polymer Solutions", J. App. Polym. Sci., 92 (2004) 2724-2732. There were 40 units of enzyme per mL in each HA solution, the two solutions having concentration of HA was 0.3 mg/ml and 1.0 mg/ml, respectively, measured simultaneously by SMSLS.

The data were transformed to achieve the superposition shown in FIG. 27. The data is shown, as in the reference, as $I_s/Kc$, where $I_s$ is the absolute Rayleigh scattering ratio (in $cm^{-1}$), K is an optical constant, and c is the concentration of protein (g/cm$^3$). The superposition of the two ETS in the two processes in FIG. 27 is so close that it is difficult to distinguish the data points of one process from those of the other. This indicates an identical mechanism, which is expected in the use of an enzyme to degrade a biopolymer where only the concentration of the biopolymer changes.

FIG. 27 also illustrates two other features. First, the superposability here is for degradation of a polymer, not aggregation, extending the superposability concept to time dependent polymer processes in solution besides aggregation. Second, not only was the time scale shifted to find optimal time scaler $\gamma=1.875$ going from the 0.3 mg/ml to 1.0 mg/ml case, but also the scale of $M_w/M_0$ was shifted by a constant amount and scaled by a factor of 1.78 going from the 0.3 mg/ml to 1.0 mg/ml case. The scale factor accounts for the fact that the concentration is higher for the 1.0 mg/ml solution, and hence also the scattering, and the shift by a constant amount accounts for the higher final background scattering level in the 1.0 mg/ml case. This illustrates the case mentioned above where the scattering quantity, $I_s/Kc$ in this case, is scaled and/or shifted, in addition to scaling the time axis, as in all the previous examples. It is expected that extended superposition will be needed whenever processes involving different concentrations of protein are analyzed for superposition. There will also be cases in which extended superposition will be required even for solutions of the same concentration. A non-limiting example of this latter case is when proteins, macromolecules or colloids are charged, and the ionic strength is varied. In such cases increasing ionic strength decreases electrostatic shielding between particles, which lowers the second virial coefficient $A_2$, leading to an increase in scattering intensity for solutions at the same particle mass concentration. See W. F. Reed "Light Scattering Results on Polyelectrolyte Conformations, Diffusion and Interparticle Interactions and Correlations", ACS Ser. 548, *Macroion Characterization*, K. Schmitz, Editor, (1994) 297-314.

Defining Proximity of Aggregation Mechanism via Superposability Criteria

The above examples illustrate that there are varying degrees of superposability and non-superposability. Perfect superposability ($R(t)=0$ for all t) will rarely be achieved, if only because experimental noise will make it difficult, if not impossible, for real ETS to match at every point in time for two processes. Hence, as described, measures such as $R(t)$ and $\chi^2$, and others, can be used to determine the degree of superposability between processes. The average of $R(t)$, defined as $$\langle R(t) \rangle = \frac{\sum_{i=0}^{N} R(t_i)}{N} \quad (21)$$

can be useful because it can approach zero if the mechanisms are the same for any pair of processes, since over many data points random noise will largely cancel out. Here, $t_i$ is the $i^{th}$ measurement over N total measurements.

A broad way of representing proximity is to consider the set of mechanistic constants $\{a_i\}$ that control the ETS for any given process. These are a function of the set of all relevant conditions $\{c_i\}$, where $c_1, c_2, c_3 \ldots$ refer to temperature, stir rate, concentration of protein, pH, ionic strength, excipients, ultrasound, light, other radiation, and other stressors (that is $\{a_i\}=\{a_i\}(\{c_i\})$) where this latter is understood to mean the set of all mechanistic constants $\{a_i\}$ is a function of the set of all relevant conditions $\{c_i\}$. Then, the issue is how much a given $\{a_i\}$ will change when each condition is incremented by $dc_j$, and how the change in $\{a_i\}$ changes the ETS from the initial one corresponding to $\{a_i\}$ to the ETS corresponding to $\{a_i+da_i\}$. The change in each $a_i$, $da_i$ can be represented as $$da_i = \sum_{j=1}^{M} \frac{\partial a_i}{\partial c_j} dc_j \quad (22)$$

where the total differential of each mechanistic constant $a_i$ is the sum of the differential changes on $a_i$ due to a change $dc_j$ in condition j, where the sum is over all M conditions that affect $\{a_i\}$. While obtaining the detailed knowledge embodied in equation 18 is extremely difficult to obtain, the effects of changes in conditions, as reflected in the ETS can be quantized.

Figure 28:
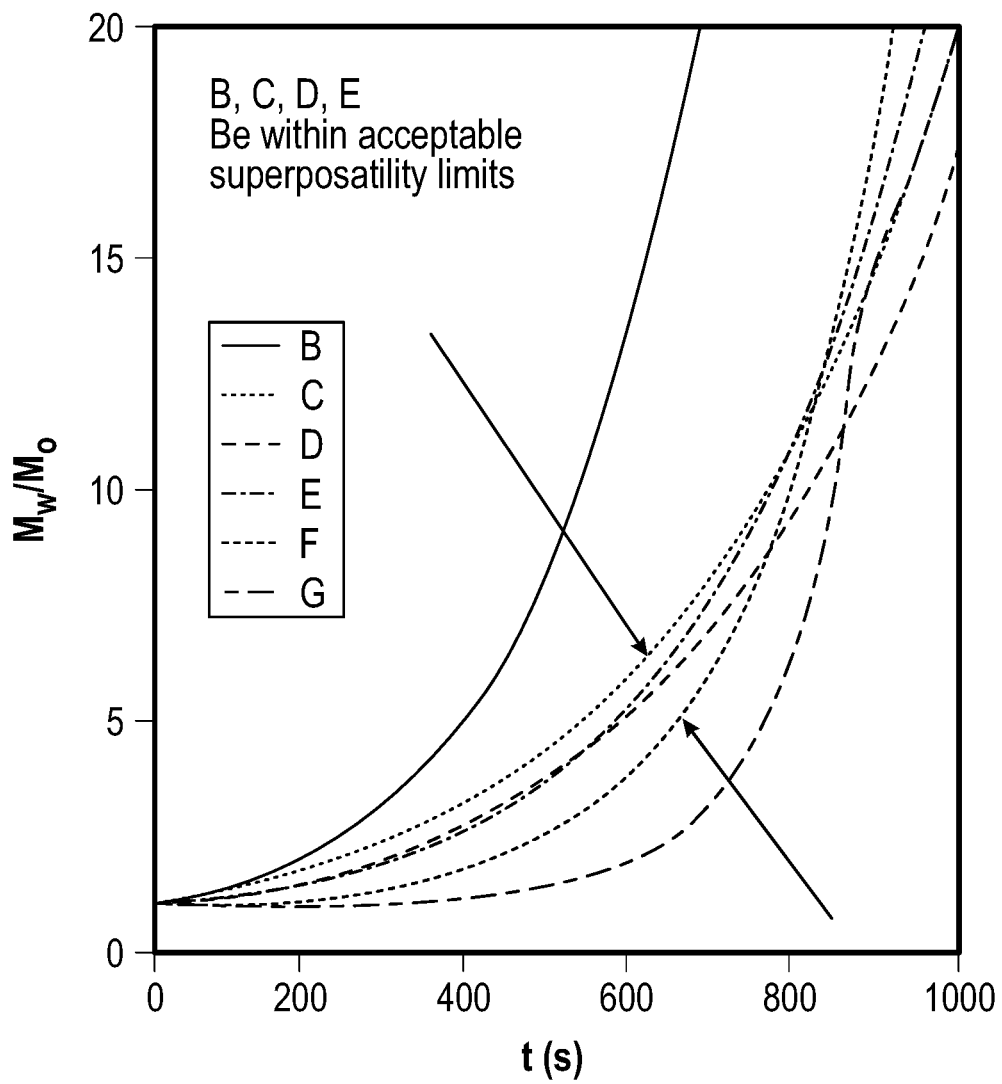
FIG. 28 is an illustration depicting a hypothetical case where conditions $\{c_i\}$ are varied and the corresponding ETS are measured, and corresponds to ETS B-E, according to an example embodiment of the present disclosure.

So, for example, FIG. 28 shows a hypothetical case where conditions $\{c_i\}$ are varied and the corresponding ETS are measured, and corresponds to ETS B-E. These conditions could include temperature, formulation pH, ionic strength, and excipient, protein concentration, stirring, other stressors, etc., or combinations thereof. Without knowing the exact effects described by equation 18, criteria can be established for what consitutes sufficiently proximate ETS so that all are considered mechanistically similar enough to be acceptable for any given purpose. For example, trajectory B might be the ETS for the optimum set of conditions for the stability and biological activity of a monoclonal antibody. Trajectories C,D,E may be proximate enough to B that all would represent a suitable formulation condition. This approach yields a means of assessing the robustness of a given formulation with respect to variations in $\{c_j\}$.

A particularly useful application would be where data such as in FIG. 28 are gathered for varying formulation conditions at an elevated temperature, and the robustness determined at that temperature, and then projecting, qualitatively, the robustness at lower temperatures where aggregation does not occur on an accessible time scale (for example, many months, over a year, etc.)

Figure 29:
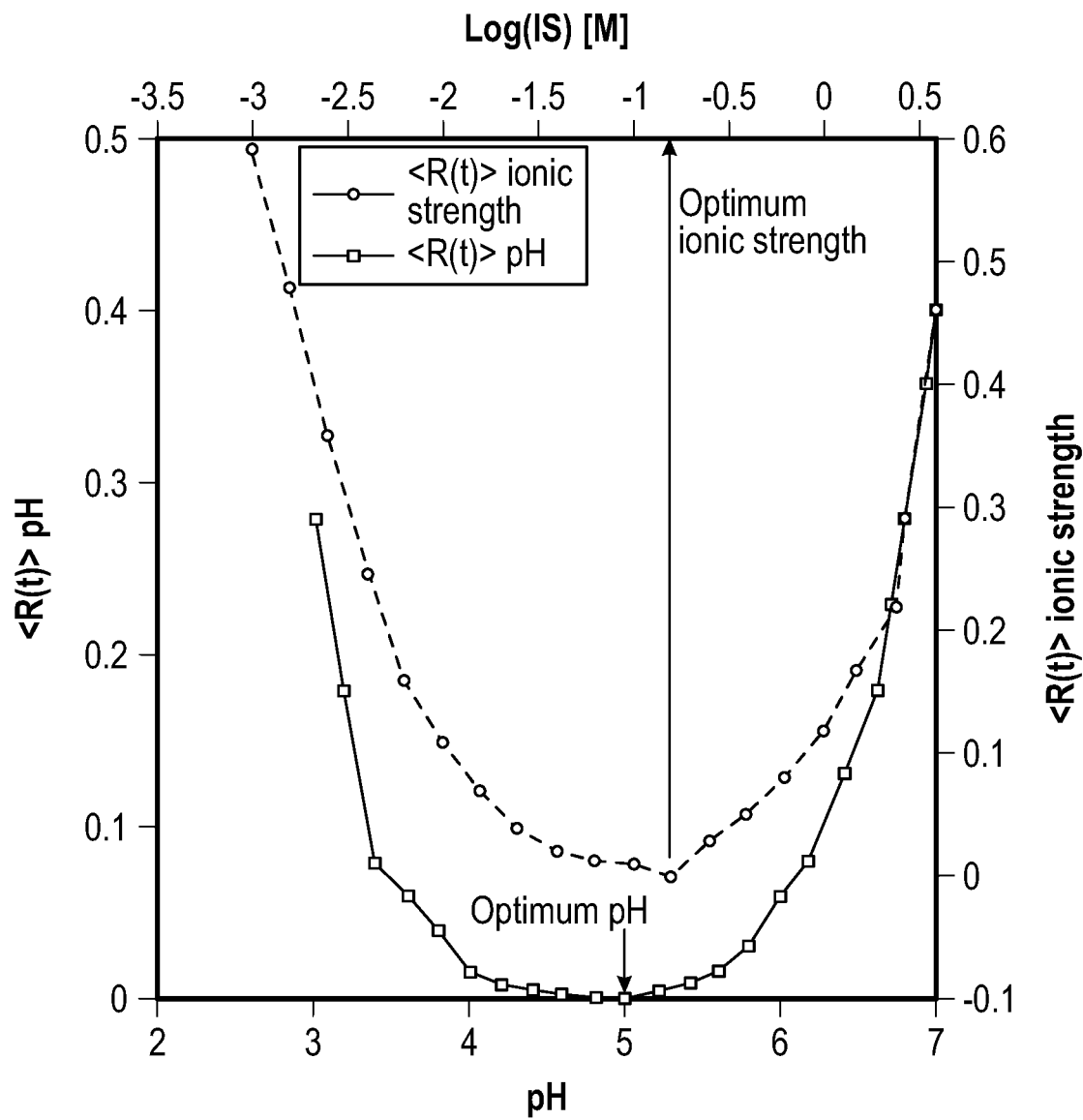
FIG. 29 is an illustration depicting a hypothetical case where the ETS for many different protein pH and ionic strength values for a certain protein at a given temperature were determined, according to an example embodiment of the present disclosure.

FIG. 29 is a hypothetical case where the ETS for many different protein pH and ionic strength values for a certain protein at a given temperature were determined and from this matrix the optimum pH and ionic strength were determined by which ETS yielded the slowest aggregation. The hypothetical curve then shows what $\langle R(t) \rangle$ according to equation 19 might look like when pH is kept at its optimum and ionic strength is varied, and then ionic strength is kept at its optimum and pH is varied. The entire data set would require a 3D representation and would resemble a paraboloid. The shallow portions around the optimum values shows the robustness of the formulation from deviations in these dimensions.

Other Uses for Superposability Analysis

While the use of superposability analysis may be pre-eminent for the development of biologic (protein-based) drugs, it can be applied to other processes. For example, degradation of polymers by acids, bases, heat, enzymes, etc. has been investigated previously and mechanistic interpretation attached to the ETS. See, for example, C. E. Reed, W. F. Reed, "Light Scattering Power of Randomly Cut Random Coils with Application to the Determination of Depolymerization Rates," J. Chemical Physics, 91 (1989) 7193-7199; W. F. Reed, et al., "Random Coil Scission Rates Determined by Time Dependent Total Intensity Light Scattering:

Hyaluronate Depolymerization by Hyaluronidase", Biopolymers, 30 (1990) 1073-1082; S. Ghosh, W. F. Reed "New Light Scattering Signatures from Polymers undergoing Depolymerization with Application to Proteoglycan Monomer Degradation" Biopolymers, 5 (1995) 435-450; W. F. Reed, "Time dependent light scattering from single and multiply stranded linear polymers undergoing random and endwise scission", J. Chemical Physics, 103 (1995) 7576-7584; L. H. Catalani et al., "Real-time Determination of Ultraviolet Degradation Kinetics of Polymers in Solution", Int'l. J. of Polymer Characterization and Analysis, 3 (1997) 231-247; and J. L. Ganter, W. F. Reed, "Real-time Monitoring of Enzymatic Hydrolysis of Galactomannans", Biopolymers, 59 (2001) 226-242. None of these investigations, however, sought the unified understanding of degradation mechanism by use of superposability. Hence, degradation studies, which are an important part of new materials development, including accelerated testing, can benefit from the superposability approach. This includes such biopolymers as polysaccharides, proteins, and polynucleic acids (e.g. DNA and RNA), and such synthetic polymers and copolymers as, but not limited to, polystyrene, polycarbonate, polyolefins, polyacrylamide, polysulfones, fluorinated polymers, polyvinyl alcohol, polyvinyl pyrrolidone, polyacrylates, polymethacrylates, polyethacrylates, etc.

Device for Measuring Superposability and Manipulating Protein Solutions in Realtime A device for measuring superposability includes of a light source, preferentially monochromatic, such as a laser or light emitting diode (LED), a sample in solution in a sample cell undergoing some time dependent process, a means of detecting the scattered light at one or more angles at any desired interval of time, a means of transmitting the scattered light intensity to a computing device, thus recording the ETS, and at least one other sample whose scattered light intensity is transmitted to a computing device, where the computing device can then determine the superposability between the two or more processes. The superposability between any pair of processes is then determined according to some criterion, or set of criteria, such as finding the optimal time scaler $\gamma$, the minimum $\chi^2$, etc. The light scattering and detection portion can involve currently available scattering intensity measuring devices such as those produced by Brookhaven Instruments Corp (BI-MwA, Holtsville, N.Y.), Wyatt Technology Corporation (Dawn, Santa Barbara, Calif.), Malvern Instruments (Lexington, Mass.), and others. All of these instruments are single sample devices, so that the two or more ETS gathered from the two or more aggregation processes must be gathered sequentially, and cannot be determined simultaneously.

A means of obtaining two or more ETS simultaneously from two or more aggregation processes is by the use of Simultaneous Multiple Sample Light Scattering as described by U.S. Pat. No. 6,618,144, the contents of which are incorporated by reference herein. An embodiment of SMSLS is available in the form of the Argen instrument from Advanced Polymer Monitoring Technologies, Inc. (New Orleans, La.). The two or more samples can be situated in non-flow batch cells, such as glass cuvettes containing, but not limited to, 10 microliters to 5 milliliters. The two or more samples can also be flowed through flow cells, where some type of pumping action is used, for example, but not limited to peristaltic pumps, syringe pumps, piston pumps, and centrifugal pumps.

Hence, an SMSLS instrument as illustrated in FIG. 18 can be connected to a computing device equipped with software capable of determining superposability, and simultaneously determine degree of superposability for many different processes. In some embodiments the illustrated computing device can be a device such as illustrated in FIG. 6. In some embodiment the computing device can be integrated into the SMSLS instrument. In some embodiments the computing device can be in communication with the SMSLS instrument. In some embodiments portions of the computing device can be integrated with the SMSLS instrument while other portions can be part of another computing device. In some embodiments the computing device can be a distributed computing device, or cloud hosted computing device.

The formulation of this approach has been made in terms of ETS that can be transformed into functions of the form $f(t)$, where the implication is that these are continuous functions. In reality, data for ETS are gathered at discrete intervals, but these can be made close enough that the experimental ETS are substantially continuous. Therefore, a sufficient number of data points can be gathered over the period of the process that the maximum amount of change in the ETS between any two points does not exceed some limit. As a non-limiting example, it could be specified that between two successive data points there should not be more than a maximum change of 1% of the ETS compared to its entire variation from t=0 until the end of measurement of the process. Thus, for example, a process lasting 1,000 seconds, and for which a change of 1% of the entire ETS occurs on the scale of 5 seconds, then at least two hundred points spaced by five seconds would need to be gathered to make this measurement substantially continuous. For a process lasting 10 days, where a change of 1% of the entire ETS occurs on the scale of 5 minutes, at least 2,880 points would need to be gathered over 10 days, each spaced 5 minutes apart. There is no requirement that sampling points be equally spaced in time, although this will often be the simplest method.

Further Uses of the Present Technology

While the previous section outlines some uses of the superposability principle which is a derivative of the central present technology, a non exhaustive list of uses is compiled next.

Optimizing Stability of Polymer and Colloid Solutions

Ideally, a perfectly stable polymer formulation, whether it contains a synthetic polymer, a biological polymer, a mixture of these, including any colloid particles, such as nanoparticles, will yield $M_w(t)=M_w(t=0)$, that is, $M_w(t)$ will not change in time. In reality it is difficult, if not impossible, to achieve such perfect stability for such solutions, especially under different thermal, mechanical, chemical, and radiation stressors. Hence, the goal will to make the solution as stable as possible against stressors. The advantage of the present technology is that it allows classes of mechanisms to be discerned from the ETS. Some classes are more stable than others. For example, a self-limiting aggregation to a low number, such as dimer or tetramer, is more stable than an unlimited aggregation that is cooperative, neutral, or even anti-cooperative. If unlimited aggregation cannot be avoided anti-cooperative aggregation is at least slower than cooperative and neutral aggregation.

Using the notion of mechanistic class the formulation conditions that provide the most stable class can be sought. For example, it is well known that varying pH, ionic strength (including differing effects according to ion type, such as $Na^+$, $Cl^-$, $Ca^{2+}$, $Cu^{2+}$, $Zn^{2+}$, $SO_4^-$, etc.), and added stabilizers (e.g. glucose, arginine, polysorbate, various surfactants, etc.) can have large effects on stability. Mechanistic classes can be determined from ETS for each formulation which can guide the development of the formulation by steering formulations towards the ones that belong to the most stable mechanistic class. Concentration of polymer can also affect aggregation rates, and possibly mechanisms.

Aiding the Discovery Phase of New Therapeutic Proteins

In developing new drug candidates researchers must select the most promising candidates from an often very wide assortment of different proteins from different mutagenic strains and sources. The mechanistic classification can provide a 'level playing field' for all the candidates; each can be tested under identical formulations and it can be determined which ones have the most desirable (stable) ETS. This can be repeated for the candidates under multiple formulation conditions to determine robustness in candidate selection. Use of high throughput screening devices, such as SMSLS, allow many candidates and conditions to be monitored at the same time.

Aiding in Development of Optimum Handling Procedures for Biologic Drugs

Figure 30:
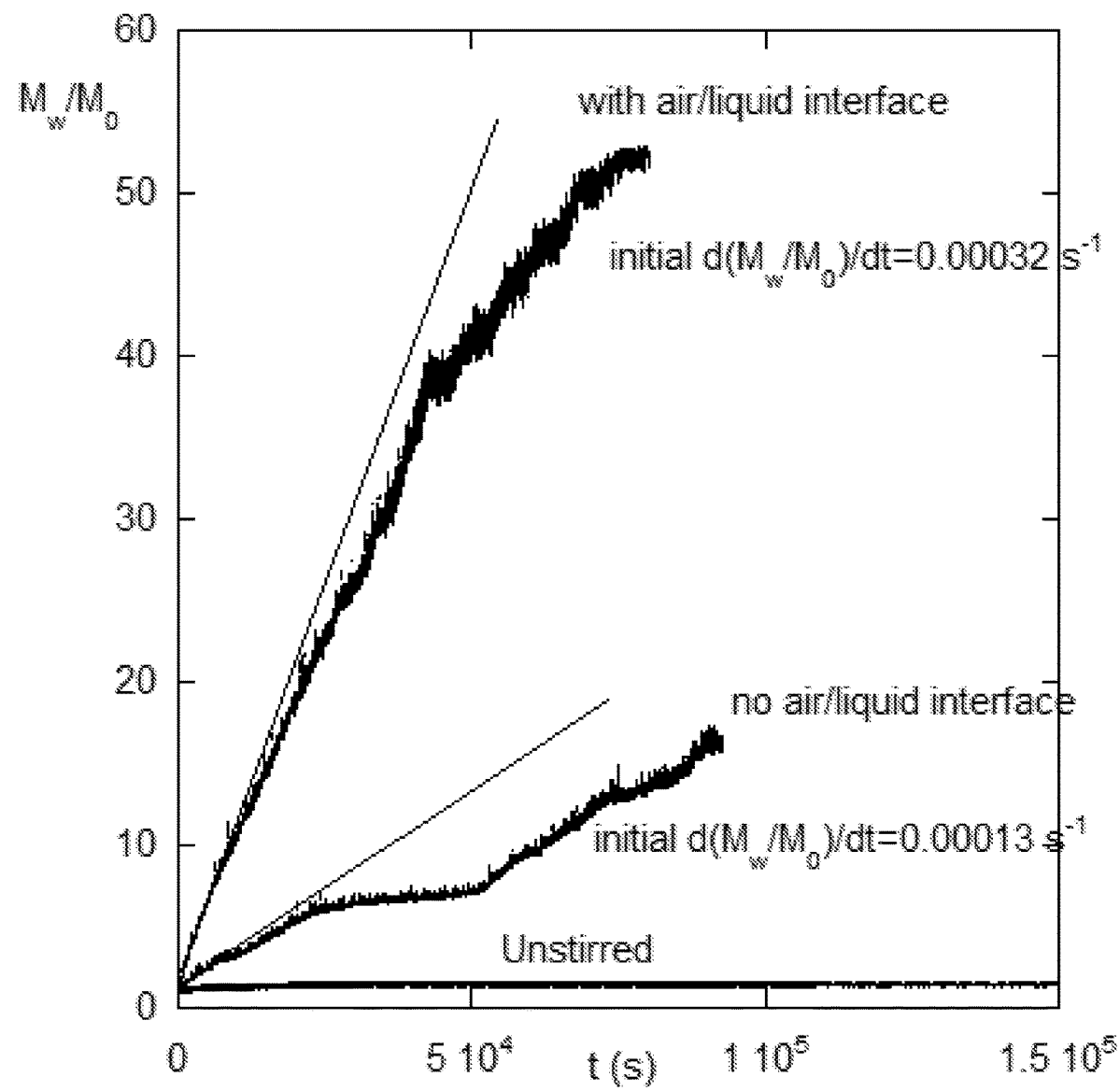
FIG. 30 is an illustration depicting aggregation of a protein caused by stirring, expressed as $M_w(t)/M_0$, according to an example embodiment of the present disclosure.

It is known that steps such as mixing, stirring, pumping, filtering, exposure to different materials, liquid/solid interfaces, liquid/gas interfaces, and loading of drug solutions into syringes and vials can cause instability. The mechanistic classes for instability can be identified via the ETS and the stressors adjusted or eliminated to reach an acceptable mechanistic class. An example of aggregation of a protein caused by stirring, expressed as $M_w(t)/M_0$ is shown in FIG. 30. Without any stirring the solution is stable over the two day monitoring period. With stirring without an air/liquid interface there is aggregation, but it is slower than aggregation when the stirring occurs with an air/liquid interface.

Aggregation Ballistics

An important issue is whether aggregation continues or stops once a stressor is removed. If aggregation stops when the stressor is removed this is clearly far more favorable than if aggregation continues once the stressor is removed. In the former case, a transient stressor, such as a mechanical stress during mixing, stirring, or pumping, or mechanical shock, such as a container falling or being impacted during shipping or storage, or a transient heating cycle during transportation or storage, would produce a finite amount of aggregates and then stop. This finite amount might fall within acceptable limits established by a regulatory agency or by the manufacturer. If aggregation continues, however, then it is much more probable that an unacceptable level of aggregation will accrue after the stressor is removed.

Figure 31:
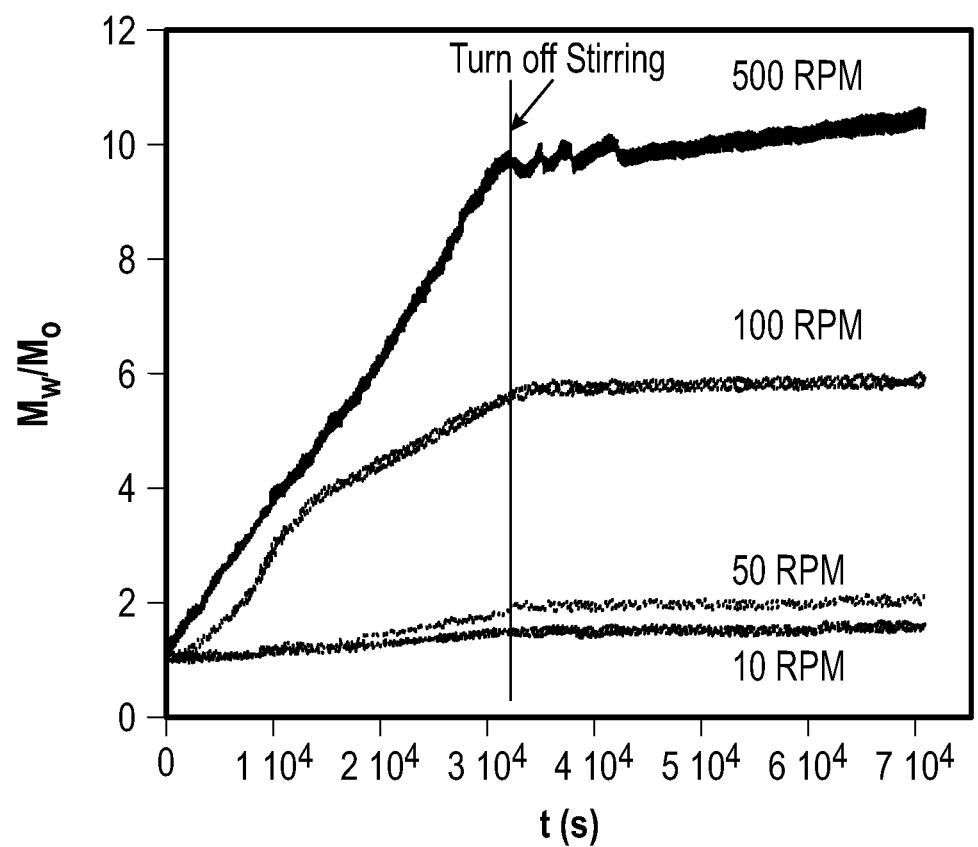
FIG. 31 is an illustration depicting the effect of removing stirring stress from an aggregating protein solution, according to an example embodiment of the present disclosure.

FIG. 31 shows how removing stirring stress from an aggregating protein solution immediately stops the aggregation.

Figure 32:
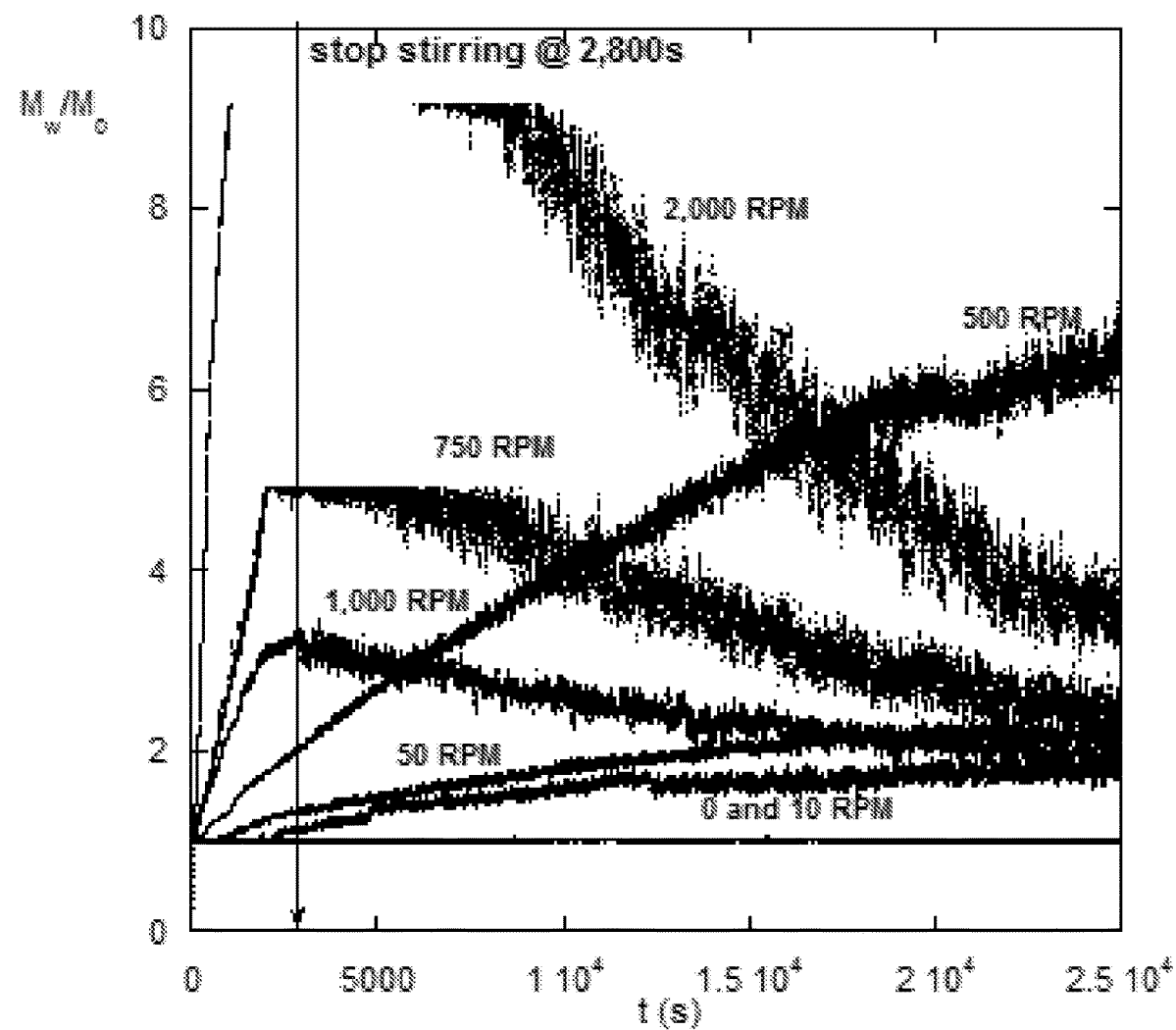
FIG. 32 is an illustration depicting behavior for a different protein under stirring, where aggregation continues after the stirring stressor is stopped, according to an example embodiment of the present disclosure.

FIG. 32 shows the behavior for a different protein under stirring, where aggregation continues after the stirring stressor is stopped. The aggregation continued upwards for 50 and 500 RPM stirring. The curves which show broadening and decrease (750, 1000 and 2000 RPM) represent precipitation events that occurred due to continued aggregation after the stirring stopped.

Aggregation 'Forensics'

If a therapeutic biologic drug is found to aggregate under clinical conditions and an analysis of the drug failure mechanism is required, the ETS can provide a mechanistic classification for the drug. It may become possible for regulatory agencies to disallow use of therapeutic drugs that fall into the most unstable mechanistic classifications, or to require that formulation conditions be found that puts them into an acceptably stable mechanistic class.

Biological Research

When a new protein is identified in an organism and is extracted, the ETS under various conditions may be related to its stability in vivo, the type of chaperones required for its folding and stability in vivo, and whether it might be a subject in vivo to enzymes called disaggregases, i.e. enzymes which exist naturally and which disaggregate aggregated proteins. See, for example, J. Shorter, "The mammalian disaggegase machinery: Hsp110 synergizes with Hsp0 and Hsp40 to catalyze protein disaggregation and reactivation in a cell-free system" https://www.nchi.nlm-.nih.gov/pubmed/22022600/ (National Institutes of Health)

Another capability with the computing system in FIG. 7 is to compute superposability in realtime. In this way, as the ETS are being gathered from two or more aggregation processes, the degree of superposability can be determined up to the most recent time point of measurement. The factorial expression in equation 11, for example, can be used to make the pairwise comparison among all the simultaneous processes in realtime. This realtime determination of superposability gives not only rapid, high throughput results, but it can also be used for controlling the aggregation. Namely, the condition of the protein solution can be changed in realtime, by means including, but not limited to, changing temperature, stirring, pH, ionic strength, adding excipients such as, but not limited to, sugars, polysaccharides, glutamic acid, arginine, surfactants such as polysorbates, and so on.

Since the goal of protein stability analysis is to achieve the least aggregation possible, the ideal ETS is a horizontal line versus time; i.e. no aggregation corresponds to light scattering intensity that does not change in time. Hence, the most ideal superposability of an aggregation process is one for which a horizontal line is achieved. While a given protein solution under specific conditions may start with a non-constant ETS, the goal would be to 'steer' the solution towards a constant ETS by manipulating the solution conditions, as described above. While these conditions may be changed manually by a human operator, it is possible to replace the human operator with an automated interface, that will make incremental or smooth changes to the various solution factors (pH, ionic strength, etc.) such as to make the solution's ETS approach a constant.

Figure 33:
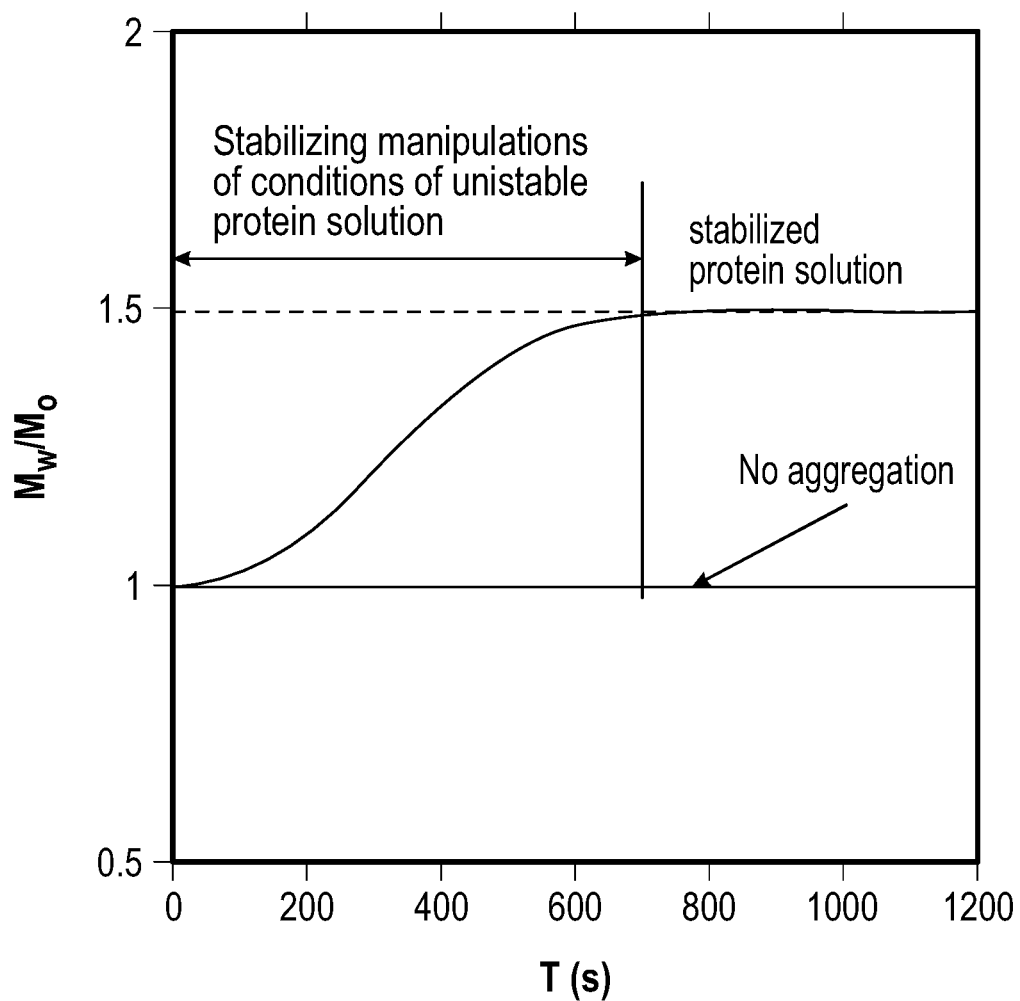
FIG. 33 is an illustration depicting an aggregation process for an initially unstable protein solution, according to an example embodiment of the present disclosure.

FIG. 33 is a non-limiting conceptual illustration of such a process for an initially unstable protein solution. The ideal case is of no aggregation, shown by the horizontal line of $M_w/M_0=1$. The actual ETS of the aggregation process is shown by the curve. During the period of t=0 to about 700 s, manipulations of the type described above (for example changing pH and/or ionic strength, adding sucrose and/or surfactants, and so on) are carried out, either manually or automatically, which bring the solution into stability, illustrated by the approach to a constant value of $M_w/M_0=1.5$. This case also illustrates the notions of piecewise superposability. The last 300 s can be superposed on the no aggregation line with extended superposability, by changing the $M_w/M_0$ scale from 1.5 to 1.

In terms of the scattering angle or angles used in the device, the widely known Zimm approximation can be considered $$\frac{Kc}{I_R} = \frac{1}{M_w}\left(1 + \frac{q^2 \langle S^2 \rangle_z}{3}\right) + 2A_2 c \tag{24}$$

where, for vertically polarized incident light $$K = \frac{4\pi^2 n^2 (dn/dc)^2}{N_A \lambda^4} \tag{25}$$

where n is the solvent index of refraction, λ is the vacuum wavelength of the incident light, dn/dc is the differential refractive index for the chemical species of interest (for example, protein, polymer, and so on) in the chosen solvent, and $N_A$ is Avogadro's number. The magnitude of the scattering vector q is $$q = \frac{4\pi n}{\lambda}\sin(\theta/2) \quad (26)$$

where θ is the angle of the photodetector in the scattering plane. $Kc/I_R$ in equation 19 can be treated as approximately equal to $M_w$ under two conditions. The first is where $$\frac{q^2\langle S^2\rangle_z}{3} \ll 1 \quad (27)$$

where $\langle S^2\rangle_z$ is the z-average mean square radius of gyration of the scatterer. The measurements in this document were made at θ=90°, although other angles are available, for example in the SMSLS products of APMT, Inc., or the single sample light scattering instrument from Wyatt Technologies. For the generic monoclonal antibody of FIGS. 14 and 15 and other figures, measurement of $A_2$ yielded an equivalent hard sphere diameter of d=9.0 nm. A separate dynamic light scattering measurements yielded a hydrodynamic diameter of $D_H$=9.1 nm. At θ=90° and for the λ=660 nm incident laser source, the error in $M_w$ is only $$\frac{\Delta M_w}{M_w} = \left(\frac{q^2\langle S^2\rangle_z}{3}\right) = .0022 \quad (28)$$

That is, the error in using θ=90° instead of extrapolating to θ=0° is only 0.22%. The values of M and d for this monoclonal antibody yield a protein density of 0.59 g/cm³. Using just θ=90° detection, globular proteins of this density could be measured up to $304M_0$ or $4.16\times10^7$ g/mol with only 10% error at that high end mass.

The second effect is from the virial coefficient $A_2$ in equation 25. The error in $M_w$ from neglect of this term is small when $$2A_2M_wc \ll 1 \quad (29)$$

where c is the protein concentration in the solution. For this generic monoclonal antibody $A_2$ was measured to be $A_2$=5.0×10⁻⁵ cm³-mol/g² and $M_w$=M=1.47×10⁵ g/mol of the native protein. Hence, for the 0.001 g/cm³ protein concentrations used in the data gathering, equation 30 amounts to $2A_2Mc$=0.0147. Therefore, the virial term contributes only 1.47% to the scattering (that is, it decreases the scattering by this amount and hence leads to a 1.47% underestimate of $M_w$).

$A_2$ is related to the equivalent hard sphere diameter d of a globular protein by $$A_2 = \frac{2\pi d^3 N_A}{3M^2} \quad (30)$$

Fluorescence Proteins usually contain tryptophan and tyrosine, which both produce fluorescence when excited by ultraviolet light in the range of 260 nm-290 nm. This fluorescence is very sensitive to the polar environment of these amino acids. When tryptophan and tyrosine shift from an apolar environment, for example, the interior of a native protein, to an aqueous environment, such as when protein unfolding exposes such amino acids to a polar environment, there is a measurable shift in fluorescence emission spectrum. The reverse is also true; when tryptophan and tyrosine shift from a polar environment to an apolar environment there is a measurable shift in the fluorescence emission spectrum. This latter process can occur when such amino acids are close to the surface of a native protein and then become immersed in a more apolar environment as proteins aggregate and surround these near-surface amino acids.

Figure 34:
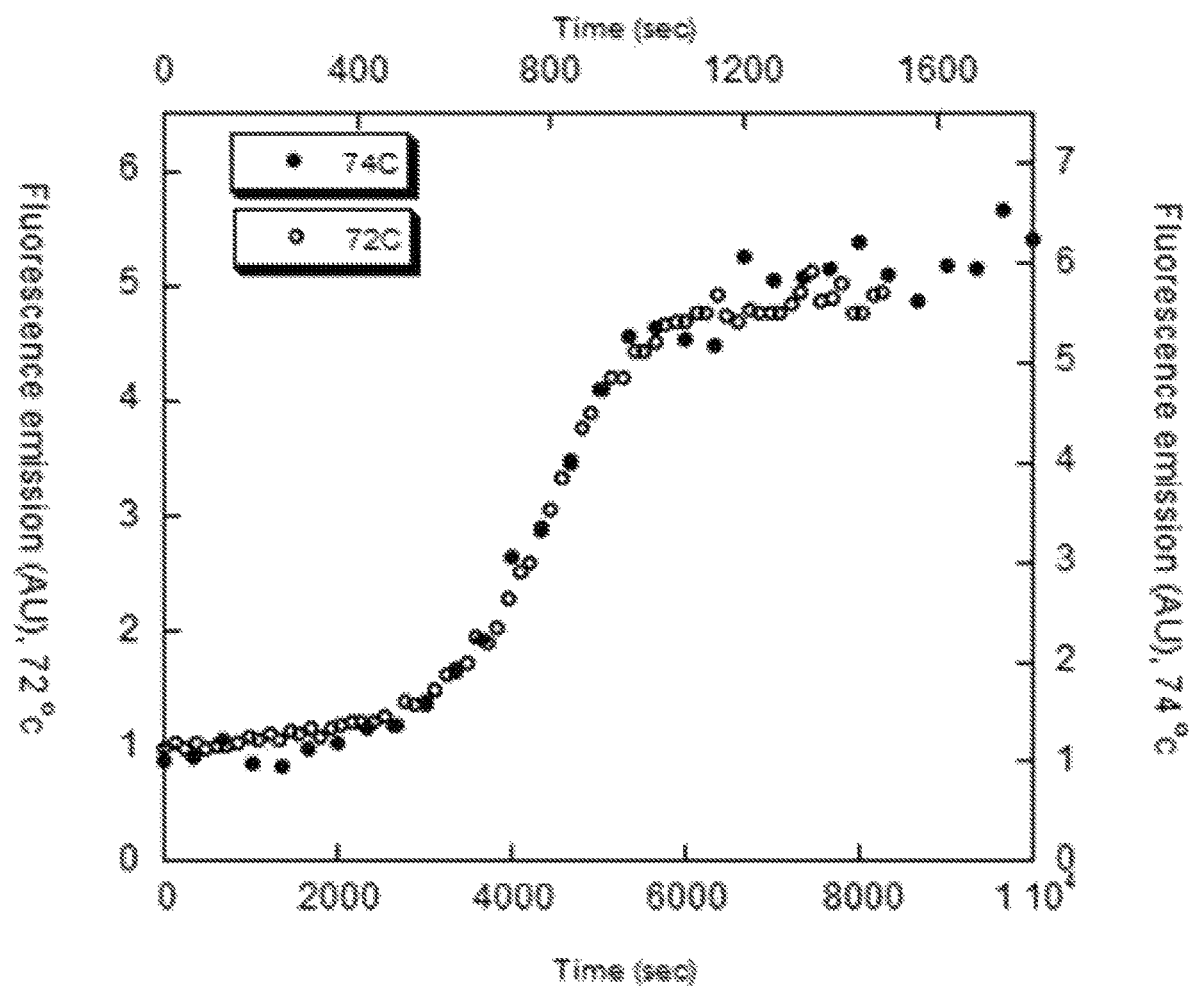
FIG. 34 is an illustration depicting fluorescence emission at 417 nm for the excitation of a generic monoclonal antibody at 72° C. and 74° C., according to an example embodiment of the present disclosure.

FIG. 34 shows fluorescence emission at 417 nm for the excitation of a generic monoclonal antibody at 72° C. and 74° C., with time scales adjusted by the optimum time scaler γ=5.56 in going from the time base of 74° C. to that of 72° C. Despite this large difference in time base, the superposition is so close it is difficult to discern the data between the two temperatures.

The increase in fluorescence emission is due to the temperature induced unfolding of the protein. The sigmoidal form of the time dependent fluorescence suggests a cooperative phenomenon. A reasonable conjecture as to the sigmoidal nature is that, considering the folding of a protein is an organized and cooperative event, the unfolding process may itself also be cooperative.

Figure 35:
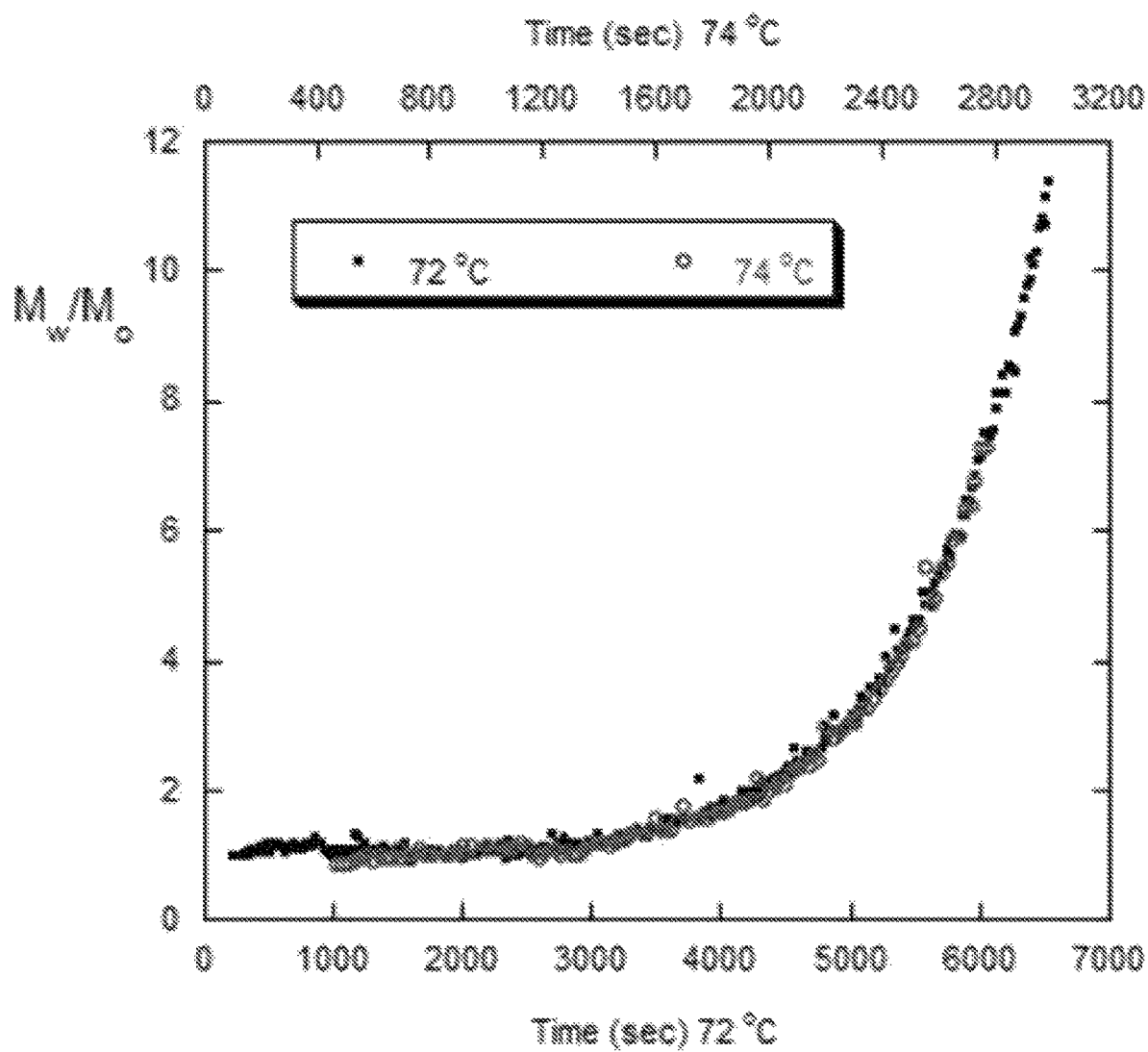
FIG. 35 is an illustration depicting ETS that corresponds to the same processes at 72° C. and 74° C. for the same monoclonal antibody, according to an example embodiment of the present disclosure.

FIG. 35 shows the ETS that correspond to the same processes at 72° C. and 74° C. for the same monoclonal antibody. These also superpose so well that it is difficult to discern the difference between the data points, despite the wide difference in time scale, for which γ=2.19, in contrast to γ=5.56 in the fluorescence superposition. The ETS show a sort of delay early in the process, which likely corresponds to the proteins being unable to aggregate until the unfolding has occurred, as seen by the sigmoidal fluorescence data in FIG. 34.

Figure 36:
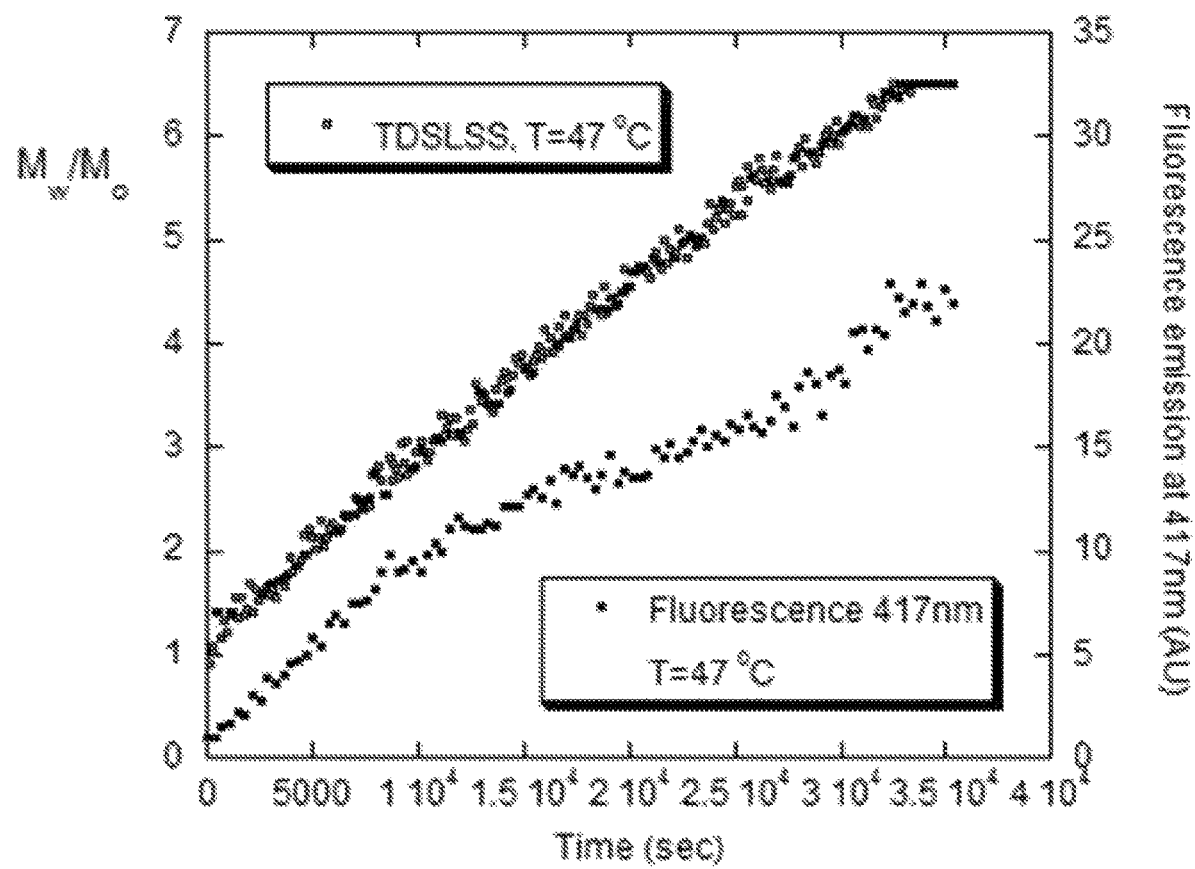
FIG. 36 is an illustration depicting the combined ETS and fluorescence emission at 417 nm for $\alpha$-chymotrypsinogen, according to an example embodiment of the present disclosure.

FIG. 36 shows combined ETS and fluorescence emission at 417 nm for α-chymotrypsinogen. This data display indicates that the fluorescence does not have a sigmoidal trend, unlike the monoclonal antibody fluorescence in FIG. 34, and, correspondingly there is no delay in the ETS. (The ETS and fluorescence data are not superposed on each other since they are dissimilar measurements that monitor different properties of the process). The non-sigmoidal nature of the α-chymotrypsinogen fluorescence data in FIG. 36 suggests that its unfolding is not cooperative. This is plausible since it is a much less massive protein (around 25,000 g/mole) than the monoclonal antibody (around 150,000 g/mole), and so would be expected to have a less complex secondary and tertiary structure.

Fluorescence Device

The instrumentation required for performing the fluorescence measurements includes, at minimum, a source of excitation in the range 260 nm-290 nm, and a source of detection in the range of 300 nm-430 nm. For single wavelength monitoring it is sufficient to excite with a lamp source such as deuterium or xenon, or an LED laser in the excitation range (for example, Thorlabs). Fluorescence emission can be detected using a detector which includes, at minimum, a cut-off filter whose lower cutoff wavelength is above the excitation wavelength, such as 310 nm, or a bandpass filter, which lets through a range of wavelengths in the emission band.

The fluorescence device must be capable of making substantially continuous measurements of the fluorescence emitted from a protein solution undergoing an aggregation process and delivering these to a computational device that can make the superposition analysis. In a further embodiment, a device that combines light scattering and fluorescence can be used to cross-correlate the behavior of these two detection modes; e.g. to establish if there is cooperativity in protein unfolding. An example of such a combined device, within the framework of SMSLS, has been discussed U.S. Publication No. 2015/0056710, the contents of which are incorporated by reference herein.

Fluorescence spectrometers, or fluorimeters, as are commercially available can also be used, provided they can make substantially continuous measurements of emitted fluorescence and deliver these to a computational device that can make the superposition analysis. Most of these fluorimeters have monochromators or gratings that yield the full fluorescence emission spectrum of samples. This permits more detailed analysis than single wavelength emission intensity monitoring in time. For example, it allows shifts in the entire spectra to be observed as the protein processes occur.

Signal Processing for Light Scattering Signals and Other Physical Quantities

Light scattering signals are characterized by positively skewed noise created by dust and particulate motion in the scattering volume. Advanced signal processing procedures accurately detect the baseline profile of time dependent light scattering curves for refined analysis. According to at least one aspect of the present disclosure, an Asymmetric Least Squares (AsLS) smoothing procedure designed to account for the asymmetry of positively skewed noise present in light scattering data may be implemented to smooth the ETS in order to facilitate matching of the ETS and MTS with greater precision. AsLS has been described in the form of baseline normalization in which signal peaks are skewed positively/negatively from a drifting baseline; (Eilers and Boelens. Baseline Correction with Asymmetric Least Squares Smoothing. October 2005). However, the use of AsLS for smoothing a signal of a physical quantity with positively/negatively skewed noise, according to the presently disclosed techniques, has not been previously disclosed.

For a noisy signal $f(t)$ with baseline $f^*(t)$, let $\hat{f}(t)$ provide an estimate of $f^*(t)$. Ideally $\hat{f}(t)=f^*(t)$. The smoothness parameter $\lambda>0$ represents a penalty for the roughness of $\hat{f}(t)$. The asymmetry parameter $1>p>0$ differentially penalizes positive/negative fluctuations of $\hat{f}(t)$ from $f(t)$. For balanced positive/negative noise $p=0.5$, $p=1$ for perfectly positive skewed noise (no negative noise), $p=0$ for perfectly negative noise. Define $\vec{w}=[w_1, w_2, \ldots, w_t]$ as a function of weights applied to the squared difference function of $f(t)$ and $\hat{f}(t)$; $d(t)=w_t*(f(t)-\hat{f}(t))^2$.

Figure 37:
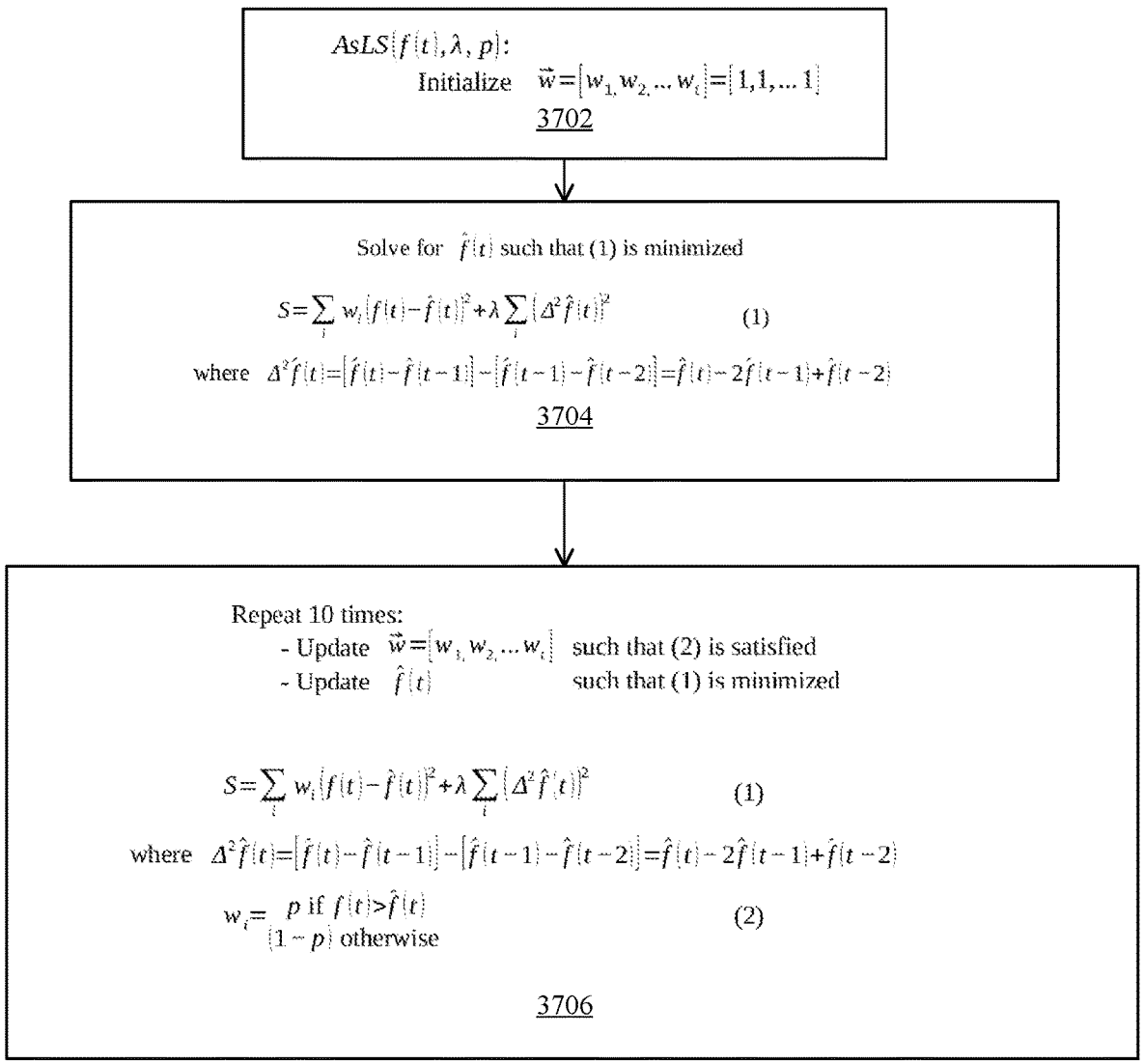
FIG. 37 is an illustration depicting a method for smoothing an ETS, according to an example embodiment of the present disclosure.

AsLS is an iterative procedure with no proven upper bound on the number of iterations required for convergence of $\hat{f}(t)=f^*(t)$. In practice, it has been shown that 10 iterations is adequate for convergence. The following procedure solves for $\hat{f}(t)$ which minimizes:

$$S=\Sigma_i w_i (f(t)-\hat{f}(t))^2 + \lambda \Sigma_i (\Delta^2 \hat{f}(t))^2 \quad (31)$$

where $\Delta^2 \hat{f}(t)=[\hat{f}(t)-\hat{f}(t-1)]-[\hat{f}(t-1)-\hat{f}(t-2)]=\hat{f}(t)-2\hat{f}(t-1)+\hat{f}(t-2)$ Then updates the weight vector according to:

$$w_i = \begin{matrix} p & \text{if } f(t) > \hat{f}(t) \\ (1-p) & \text{otherwise} \end{matrix} \quad (32)$$

as shown in FIG. 37. As depicted in FIG. 37, at 3702 AsLS($f(t)$, $\lambda$, p): Initialize $\vec{w}=w_1,w_2, \ldots w_t]=[1,1, \ldots 1]$. At 3704, $\hat{f}(t)$ is solved for such that the expression shown in (1) of FIG. 37 is minimized. At 3706, $\vec{w}=w_1,w_2, \ldots w_t$ is updated such that the expression shown in (2) of FIG. 37 is satisfied. $\hat{f}(t)$ is updated such that the expression shown in (1) of FIG. 37 is minimized. The procedure at block 3706 is repeated 10 times, as described in FIG. 37.

Figure 38:
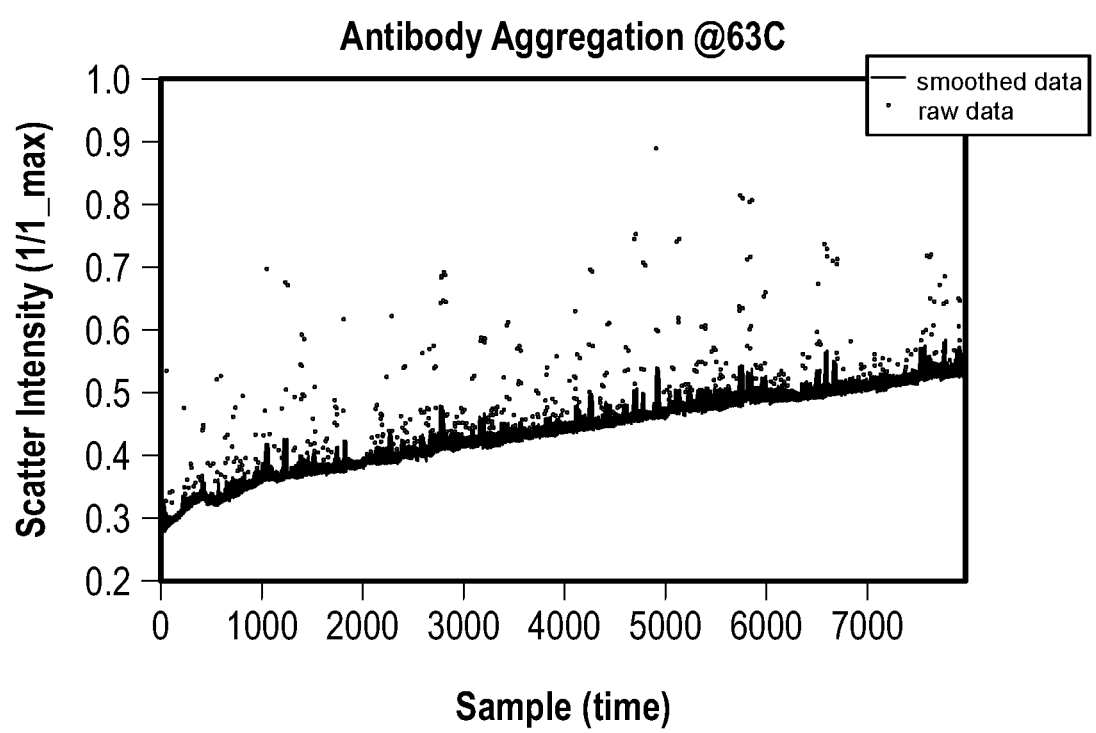
FIG. 38 is an illustration depicting the failure of a rolling average filter to accurately detect a baseline.
Figure 39:
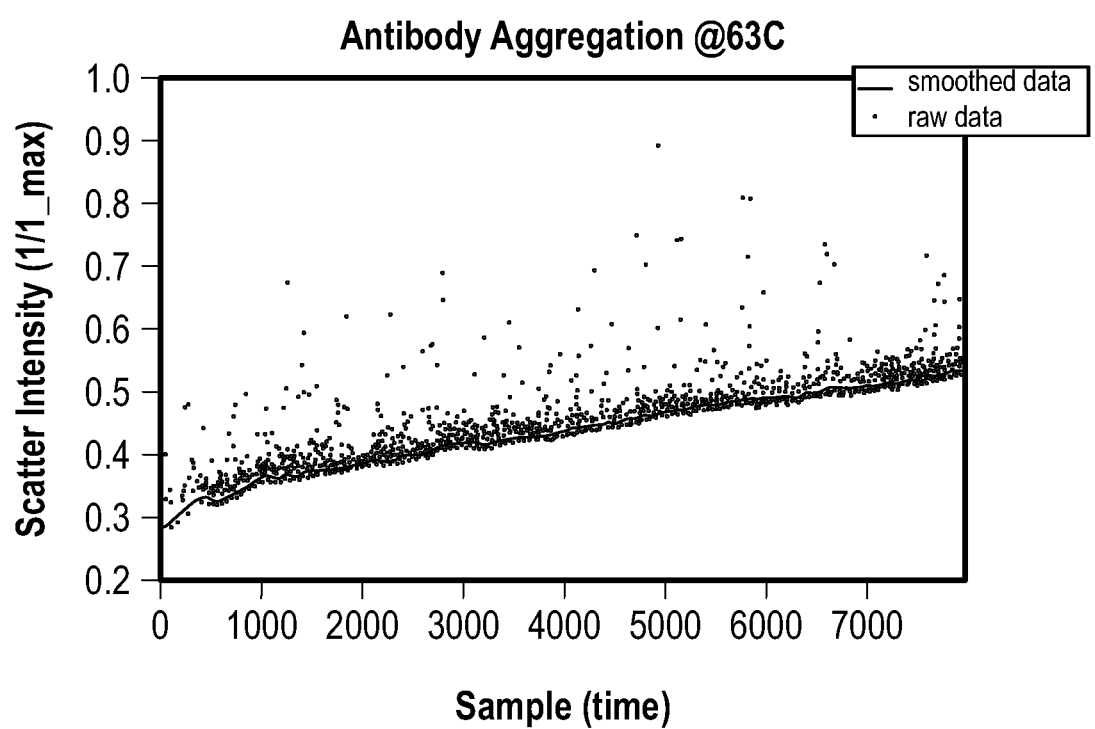
FIG. 39 is an illustration demonstrating that AsLS with proper parameter tuning effectively ignores these spikes and accurately detects the baseline signal, according to an example embodiment of the present disclosure.

FIG. 38 shows the failure of a rolling average filter to accurately detect a baseline. High frequency positive fluctuations from the baseline are indicative of noise caused by dust motion in the sample solution. Such signals do not represent a steep increase in the average molecular weight. The 9-point rolling mean overestimates the true baseline by fitting this noise. FIG. 39 demonstrates that AsLS with proper parameter tuning effectively ignores these spikes and accurately detects the baseline signal.

Figure 40:
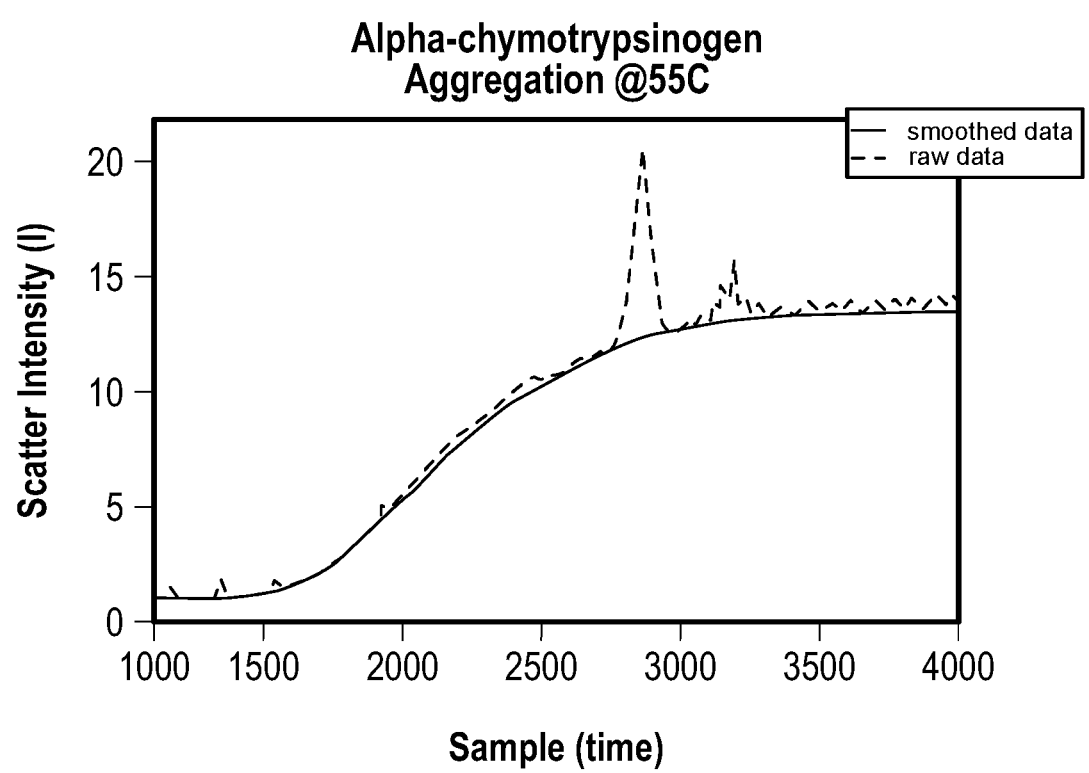
FIG. 40 is an illustration demonstrating that AsLS can filter low-frequency noise created by particulate motion as well as high frequency noise, according to an example embodiment of the present disclosure.
Figure 41:
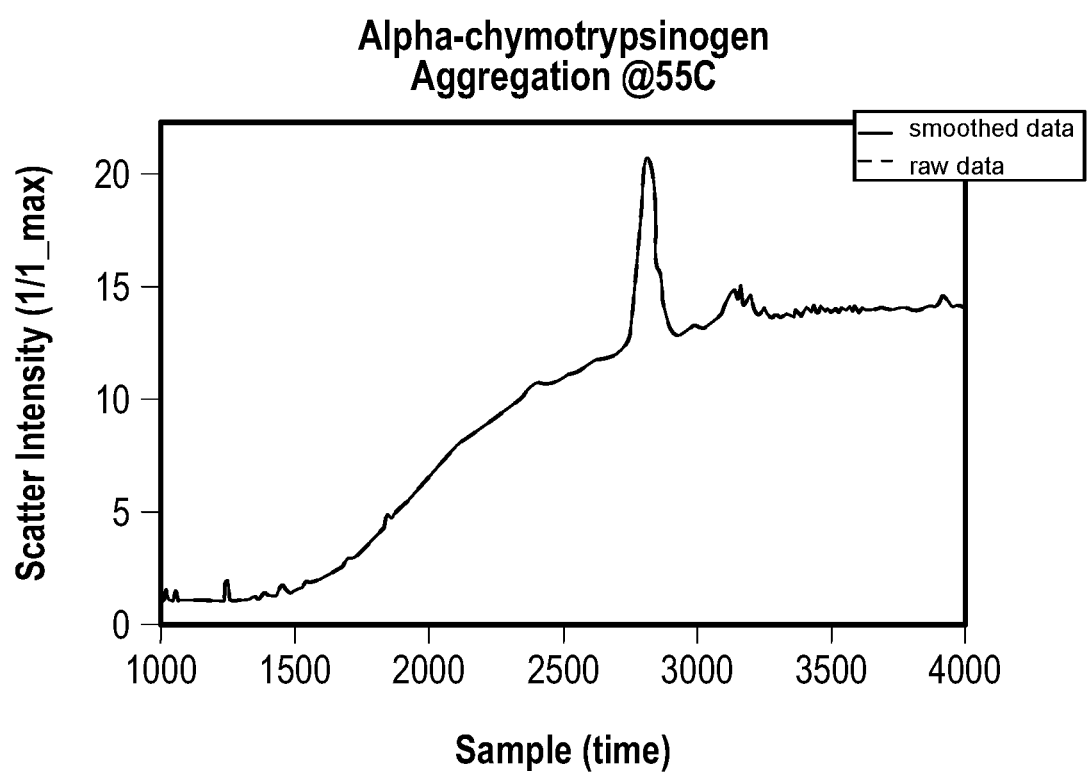
FIG. 41 is an illustration demonstrating that a Savitzk Golay filtering method succeeds at filtering high frequency fluctuations but fail to filter low-frequency events.

FIG. 40 shows that AsLS can filter low-frequency noise created by particulate motion as well as high frequency noise. The sharp deviation from and subsequent return to the sigmoidal baseline around t=2600 is indicative of the transitory movement of a large scattering particle into the scattering volume. This signal does not indicate a rapid increase and decrease in the average solution molecular mass. AsLS interpolates a curve true to the shape of the baseline with no parametric assumptions (i.e. fitting a sigmoidal function to the data). Other methods, such as Savitzky Golay filters, illustrated in FIG. 41, filter high frequency fluctuations but fail to filter low-frequency events.

Figure 42:
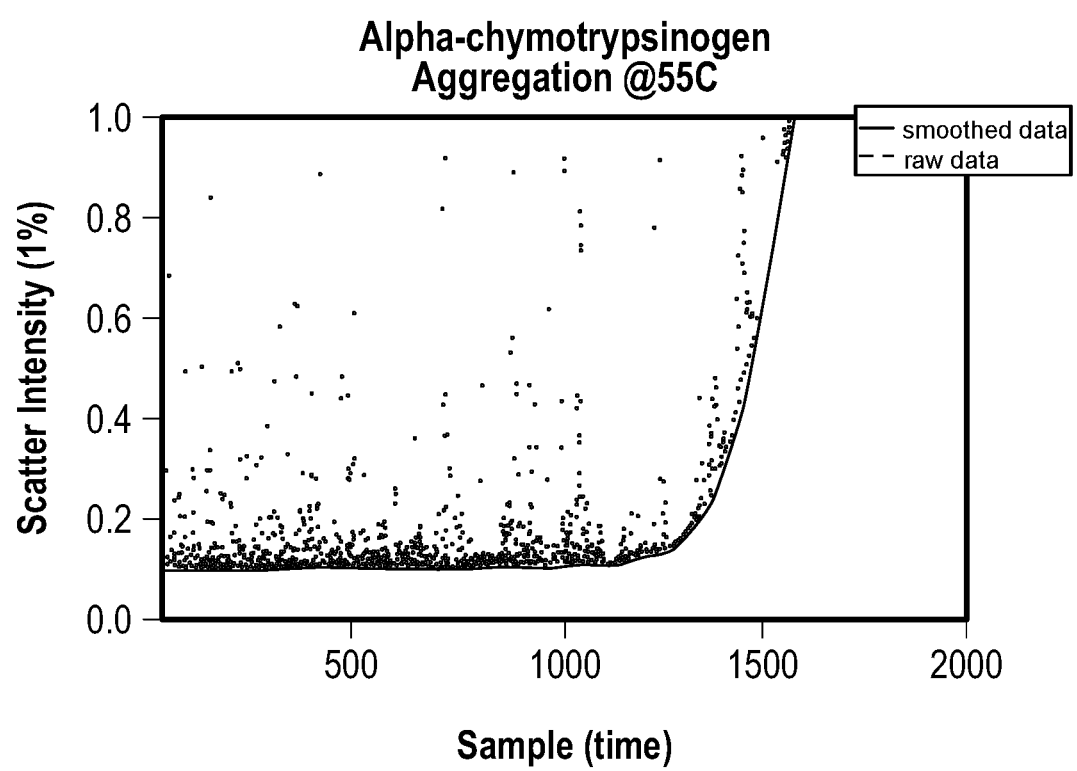
FIG. 42 is an illustration demonstrating that AsLS captures rapid changes in aggregation processes, according to an example embodiment of the present disclosure.

As shown in FIG. 42, AsLS captures rapid changes in aggregation processes. This nucleation dependent process is characterized by a lag period in which the scattering intensity remains constant and little aggregation occurs. After an aggregate nucleus forms, an autocatalytic cycle results in a rapid increase in aggregate mass (and scattering intensity).

In the present embodiment, the optimal input parameters $\lambda$, p are determined manually by visual inspection of the data and baseline curves. It is possible that the procedure can be automated using an ideal optimization metric, the mean squared error of $f^*(t)$ and $\hat{f}(t)$, relies on an unknown quantity, $f^*(t)$.

Superposition Analysis

It is surmised that if the non-linear kinetic profiles of two or more aggregation processes can be superposed onto each other by rescaling the time-domain, then those processes follow a similar mechanistic pathway. The superposition principle holds if, for two functions $f_1(t)$, $f_2(t)$, there exists constants $\tau$, $\theta$ that rescale and offset (respectively) the time-domain index of $f_2(t)$ such that the mean squared error (herein referred to as $X^2$) between the two functions is minimized to a value proportional to the level of noise in the sample. Let $F_2(t)$ represent the rescaled curve of $f_2(t)$. The optimal rescaling constants $\gamma^*$, $\tau^*$ can be computed by an iterative optimization procedure that computes and stores $$X^2 = \frac{1}{N_{real}} \sum_t (f_1(t) - F_2(t))^2$$

over a range of possible $\gamma$, $\tau$ values. The optimal parameters $\gamma^*$, $\tau^*$ are taken as those that yield the minimum value of $\chi^2$. The $N_{real}$ term represents the number of terms that yield a real number in the summation contained in $X^2$, to prevent $F_2(t)$ from simply scaling beyond the range of $f_2(t)$ and achieving a minimal error.

$$g(\gamma^*, \tau^*) = \min(X^2) = \min\left(\frac{1}{N_{real}}\sum_t (f_1(t) - F_2(t))^2\right) \approx 0 \qquad (33)$$

Figure 43:
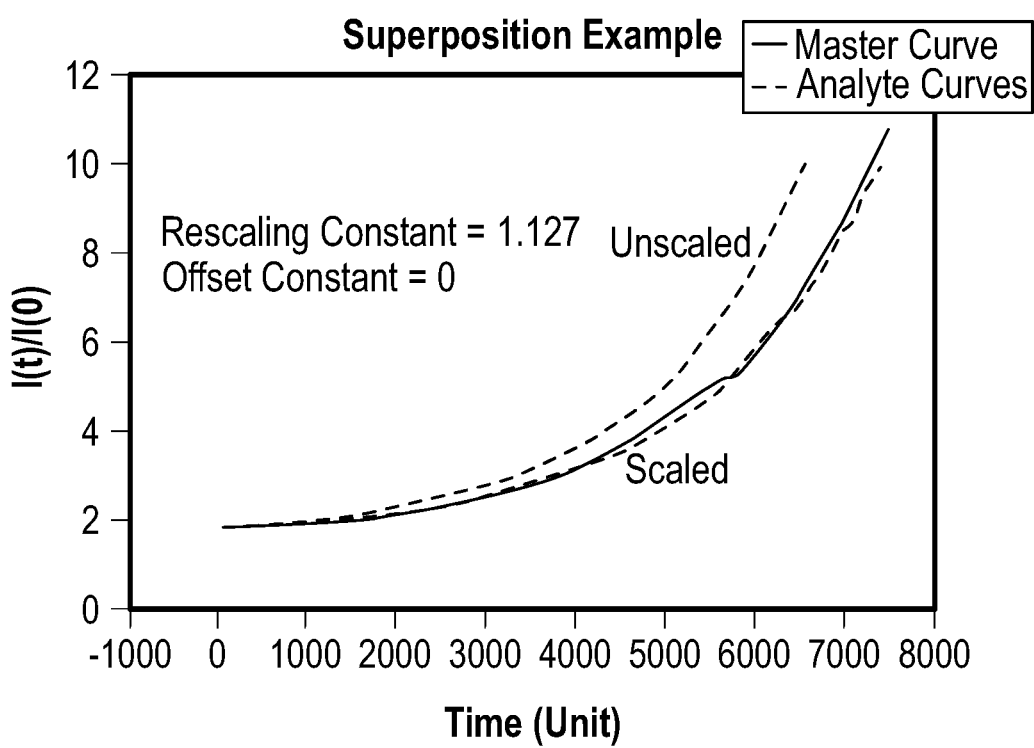
FIG. 43 is an illustration demonstrating a curve scaled to a master curve by a multiplicative constant of 1.127, according to an example embodiment of the present disclosure.
Figure 44:
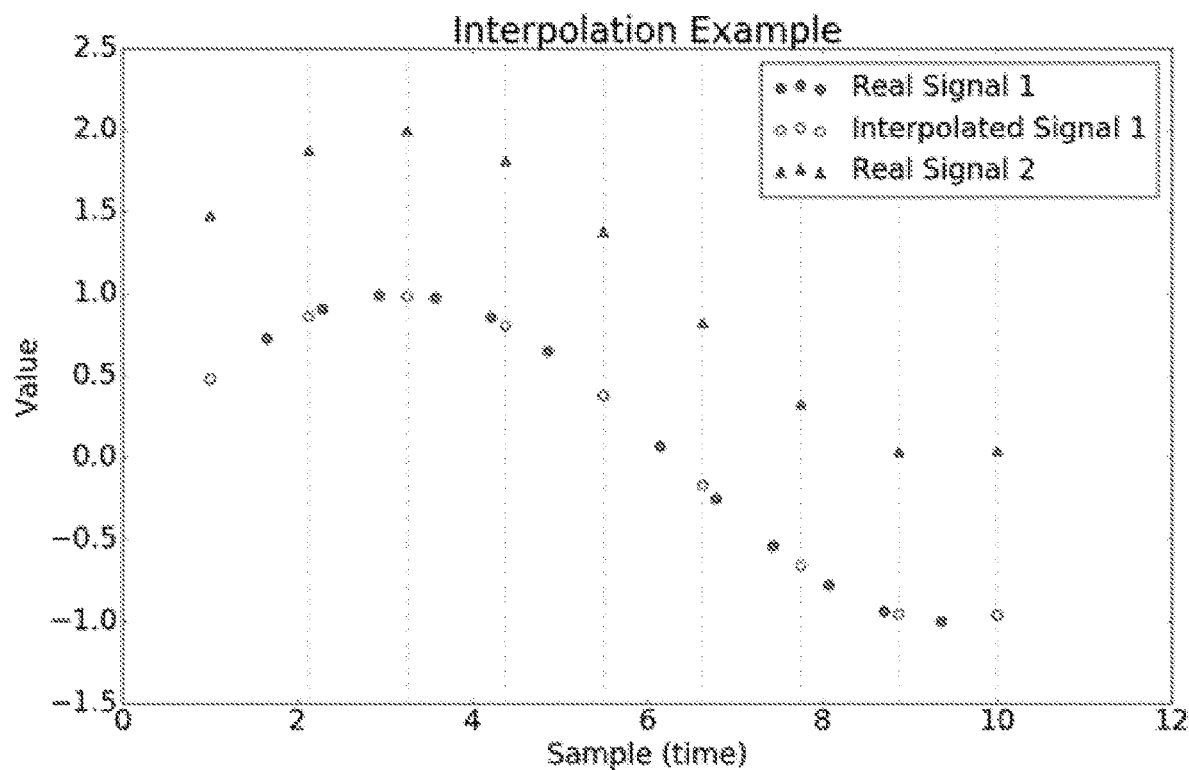
FIG. 44 is an illustration demonstrating the interpolation of signal 1 for comparison to signal 2 obtained at a different sampling rate, according to an example embodiment of the present disclosure.

FIG. 43 shows an curve (white) scaled to a master curve (black) by a multiplicative constant of 1.127. $X^2$ can only be calculated when the time-index of $f_1(t)$ and $F_2(t)$ are aligned. Assuming that both signals were sampled at the same rate, the unscaled analyte curve is aligned with the master curve. If the analyte is scaled by a non integer coefficent then the time-indexes of the curves are no longer aligned. The master curve must be resampled to align with $F_2(t)$. Resampling can be accomplished in one of several ways. Linear interpolation assumes a linear relationship between two known values $f_1(2)$ and $f_1(3)$ to calculate the expected value at $f_1(2.3)$ for example. This linearity assumption induces error into the analysis, but this is negligible for samples obtained at a high enough sampling frequency. An alternative method may include fitting a polynomial fit to a window of data surrounding an unknown point and interpolating based on this relationship. FIG. 44 above shows the interpolation of signal 1 for comparison to signal 2 obtained at a different sampling rate.

The presence of experimental noise in a non-ideal system ensures $\min(X^2) > 0$ even for perfectly superposable curves. It is necessary in practice to set a threshold value T that differentiates superposable curves from non-superposable. For noisy signals, a greater T will capture more superposable signatures, but increase the risk of returning false positives. If signals are too corrupted, superposition analysis is virtually impossible. Denoising procedures such as AsLS enhance the capabilities of superposition analysis to distinguish between aggregation mechanisms by allowing a stricter threshold.

Figure 45:
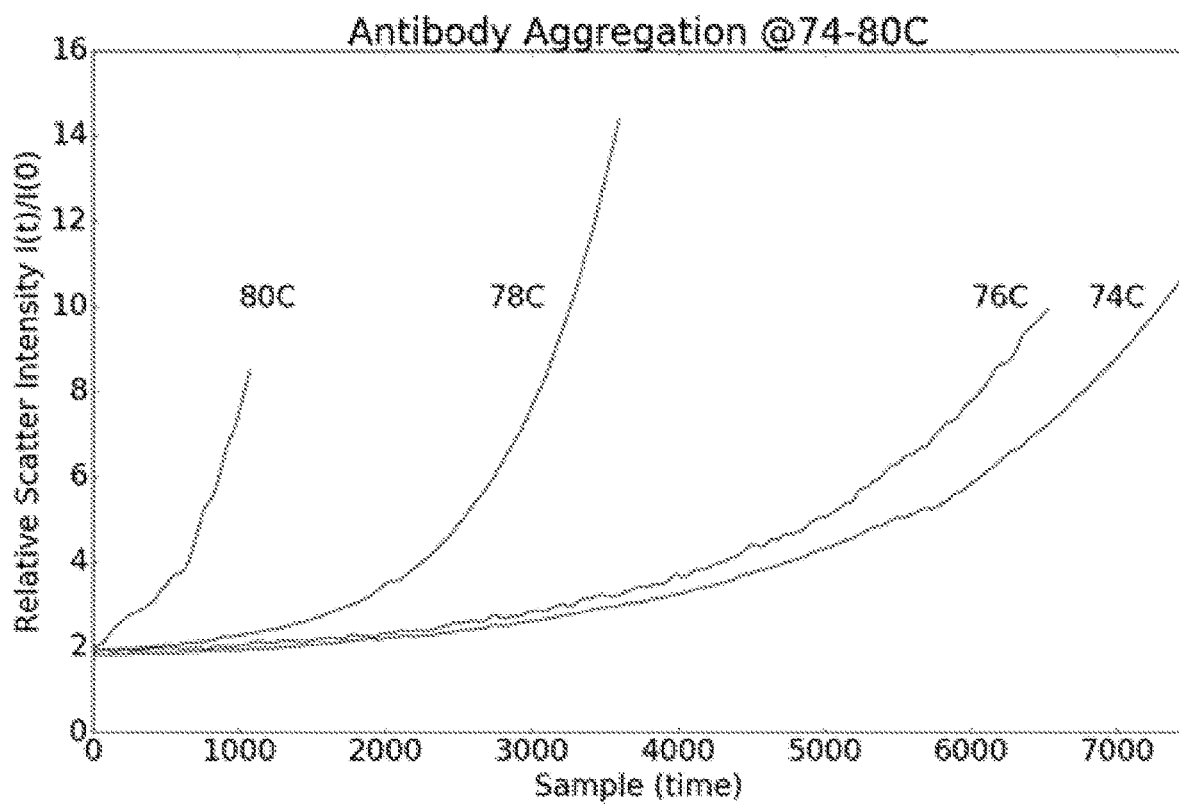
FIG. 45 is an illustration demonstrating the unscaled scattering intensity of aggregating antibodies under thermal stress, according to an example embodiment of the present disclosure.
Figure 46:
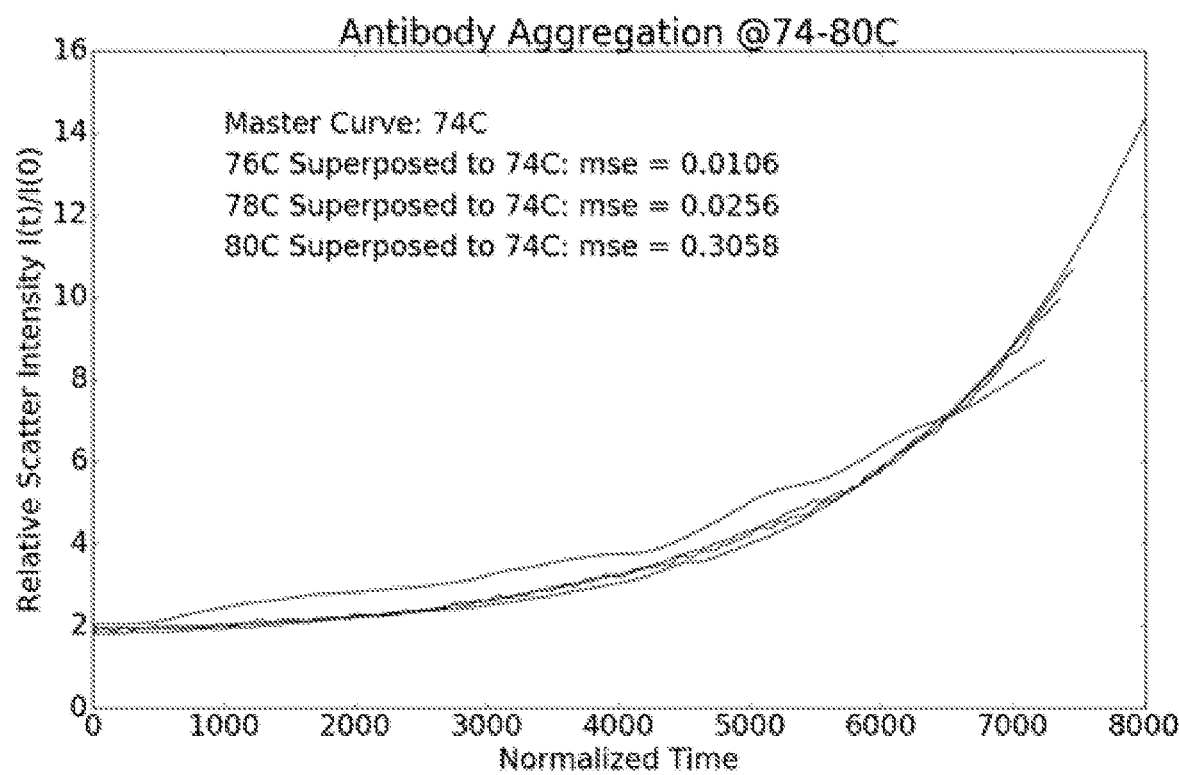
FIG. 46 is an illustration depicting unscaled and scaled curves superposed onto each other, according to an example embodiment of the present disclosure.

FIG. 45 shows the unscaled scattering intensity of aggregating antibodies under thermal stress and the scaled curves superposed onto each other as shown in FIG. 46. Curves have been smoothed with AsLS. The aggregation profiles at 74, 76, and 78 C superpose well onto each other, indicating similar mechanisms of aggregation. The 80 C profile does not fit perfectly onto the master curve, hinting at a shift in aggregation mechanisms between 78-80 C. It is possible that at this critical temperature, the structure of the protein is destabilized in a manner that enables alternative and accelerated pathways for aggregation.

There may exist computationally efficient versions of this optimization. A greedy approach takes the locally optimal solution for one of the parameters, i.e. $\gamma^*$, while holding the other, $\tau$, constant; then computing the optimal solution for $\tau^*$ given $\gamma^*$.

Additional Variation of the General Mechanistic Model

According to at least one aspect of the present disclosure, additional variations of the General Mechanistic Model are within the spirit and scope of the present disclosure. The generalized mechanistic model equations presented in equations 7-9 are not exhaustive and other mechanisms can exist. For example, in the case of stirring stress it is sometimes likely that the grinding contact between a revolving stir bar and the surface of the vessel containing the proteins mechanically damages the proteins and crushes them into aggregates each of which contain many proteins. In such a case there is no individual damage mechanism, such as in equation 7. An example of this is FIG. 31 where the aggregation stops once the stirring is turned off; i.e. the aggregates are produced purely from stirring, and once they cease to be produced by stirring no more aggregate activity occurs; i.e. aggregates formed by this mechanism do not aggregate with each other. Then $$\frac{dP_j}{dt} = w_j N \qquad (34)$$

where $w_j$ is the probability that when an aggregating forming event occurs due to stir crushing an aggregate with j proteins in it is produced. N is, as before, the number concentration of native proteins. The $w_j$ represents a probability function and can depend on stirring type or rate (e.g. RPM), nature of the stir geometry and contact details between stirring element and container surface, hydrodynamic stress field generated by stirring, temperature, and other factors, in addition to the type of biological polymer and the solution conditions.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

What is claimed is:

1. At least one non-transitory computer readable medium comprising instructions stored thereon, the instructions effective to cause a computing system to:
   receive an experimental time dependent light scattering signature (ETS), the ETS comprising experimental data related to an average molecular weight of biological polymer components in a solution over time;
   identify an Ansatz for evaluating the ETS, the Ansatz being an initial value for at least one key variable in a generalized mechanistic model (GMM); and
   adjust the at least one key variable in the GMM until a final model-based time dependent light scattering signature (MTS) is identified, the final MTS sufficiently matching the ETS;
   wherein the at least one key variable is a rate constant value in the GMM.

2. The at least one non-transitory computer readable medium of claim 1,
   wherein the final model-based time dependent light scattering signature identifies at least one biological polymer aggregation mechanism; and
   wherein the instructions are effective to further cause the computer system to output instructions to alter the formulation conditions of the solution until a predetermined biological polymer aggregation mechanism is achieved,
   wherein the formulation conditions comprises one selected from the group consisting of temperature, formulation pH, ionic strength, excipient type, excipient concentration, biological polymer concentration, stirring rate, and combinations thereof.

3. The at least one non-transitory computer readable medium of claim 1, wherein the GMM is based on a model of protein aggregation and the Ansatz is identified by selecting the Anstaz from a database of protein aggregation mechanisms that have been modeled and characterized.

4. The at least one non-transitory computer readable medium of claim 1, wherein the at least one key variable comprises one selected from the group consisting of $\alpha$, $k_{i,j}$, $k_{n,i}$, and combinations thereof.

5. The at least one non-transitory computer readable medium of claim 1, wherein the ETS comprises continuously measured experimental data; and wherein the instructions are effective to further cause a computer system to smooth the experimental data comprising the ETS, the smoothing of the experimental data comprising implementing an Asymmetric Least Squares (AsLS) smoothing procedure.

6. The at least one non-transitory computer readable medium of claim 1, wherein the final model-based time dependent light scattering signature identifies at least one biological polymer aggregation mechanism; wherein the Ansatz is selected from a database of model-based time dependent light scattering signatures, wherein the biological polymer aggregation mechanisms reflected in the model-based time dependent light scattering signatures have been characterized; and wherein the instructions are effective to further cause a computer system to output instructions to optimize or adjust at least one formulation condition for the biological polymer component solution based on the identified final MTS or the at least one biological polymer aggregation mechanism.

7. The at least one non-transitory computer readable medium of claim 1, wherein the final model-based time dependent light scattering signature identifies at least one biological polymer aggregation mechanism; wherein the at least one biological polymer aggregation mechanism is identified by superposing the ETS with a single parameter (single mechanism) transformation of the time axis between them; and wherein the biological polymer components comprises at least one protein.

8. A method comprising:
receiving an experimental time dependent light scattering signature which is made up of experimental data related to an average molecular weight of biological polymer components in a solution over time;
selecting a time dependent light scattering signature from a database of time dependent light scattering signatures, wherein the biological polymer aggregation mechanisms reflected in the time dependent light scattering signatures have been characterized;
determining if the experimental time dependent light scattering signature sufficiently matches selected time dependent light scattering signature, wherein a match indicates that the biological polymer aggregation mechanism reflected in the selected time dependent light scattering signature is the same biological polymer aggregation mechanism represented in the experimental time dependent light scattering signature.

9. The method of claim 8, wherein the selecting the time dependent light scattering signature from a database of time dependent light scattering signatures comprises identify an Ansatz for evaluating the experimental time dependent light scattering signature, the Ansatz identifying at least one key variable; the method further comprising adjusting the at least one key variable in the Ansatz until the experimental time dependent light scattering signature sufficiently matches selected time dependent light scattering signature.

10. The method of claim 8, wherein the biological polymer components comprises at least one protein and the initial time dependent light scattering signature is based on a model of protein aggregation.

11. The method of claim 9, wherein the key variable comprises one selected from the group consisting of $\alpha$, $k_{i,j}$, $k_{n,i}$, and combinations thereof.

12. The method of claim 8, wherein the experimental time dependent light scattering signature is made up of experimental data that is continuously measured; the method further comprising smoothing the data comprising the ETS, the smoothing comprising implementing an Asymmetric Least Squares (AsLS) smoothing procedure.

13. The method of claim 8, further comprising adjusting at least one formulation condition for a biological polymer solution based on the identified final time dependent light scattering signature or the at least one biological polymer aggregation mechanism; wherein the at least one formulation condition comprises one selected from the group consisting of temperature, formulation pH, ionic strength, excipient type, excipient concentration, biological polymer concentration, stirring rate, and combinations thereof.

14. The method of claim 8, wherein the time dependent light scattering signature is a model-based time dependent light scattering signature and the database comprises model-based time dependent light scattering signatures.

15. A system comprising:
an SMSLS device including:
at least one sample cell configured to receive a solution containing a biological polymer;
a measurement device, the measurement device being configured to continuously measure the solution; and
a computing system including:
at least one processing device;
at least one storage including instructions stored thereon, the instructions effective to cause the at least one processing device to:
receive an experimental data related to an average molecular weight of protein components in a solution over time from the measurement device, the experimental data making up an experimental time dependent light scattering signature;
identify an ansatz for evaluating the experimental time dependent light scattering signature, the Ansatz being a an initial set of key variables to introduce into a generalized mechanistic model (GMM) the Ansatz establishing an initial value for at least one key variable, wherein the at least one key variable is a rate constant value in the GMM; and
adjust the at least one key variable in the generalized mechanistic model until a final model-based time dependent light scattering signature is identified, the final model-based time dependent light scattering signature sufficiently matching the experimental time dependent light scattering signature.

16. The system of claim 15, wherein the final model-based time dependent light scattering signature identifies at least one biological polymer aggregation mechanism; wherein the instructions are effective to further cause a computer system to output instructions to optimize or adjust at least one formulation condition for a biological polymer solution based on the identified final model-based time dependent light scattering signature or the at least one biological polymer aggregation mechanism, the formulation conditions comprising one selected from the group consisting of temperature, formulation pH, ionic strength, excipient type, excipient concentration, biological polymer concentration, stirring rate, and combinations thereof.

17. The system of claim 15, wherein the biological polymer components comprises at least one protein; and wherein the Ansatz is identified by selecting the Anstaz from a database of protein aggregation mechanisms that have been modeled and characterized and the initial model-based time dependent light scattering signature is based on a model of protein aggregation.

18. The system of claim 15, wherein the at least one key variable comprises one selected from the group consisting of $\alpha$, $k_{i,j}$, $k_{n,i}$, and combinations thereof.

19. The system of claim 15, wherein the experimental time dependent light scattering signature which is made up of experimental data is continuously measured; and wherein the instructions are effective to further cause a computer system to smooth the experimental data comprising the ETS, the smooth the experimental data comprising implementing an Asymmetric Least Squares (AsLS) smoothing procedure.

20. The system of claim 15, wherein the initial model-based time dependent light scattering signature is based on a model of protein aggregation and the Ansatz is selected from a database of model-based time dependent light scattering signatures, wherein the protein aggregation mechanisms reflected in the model-based time dependent light scattering signatures have been characterized; and wherein the instructions are effective to further cause a computer system to output instructions to alter the formulation conditions of the solution until a predetermined biological polymer aggregation mechanism is identified, the formulation conditions comprising one selected from the group consisting of temperature, formulation pH, ionic strength, excipient, biological polymer concentration, stirring rate, and combinations thereof.

* * * * *